(12) United States Patent
Spits et al.

(10) Patent No.: US 9,822,339 B2
(45) Date of Patent: Nov. 21, 2017

(54) MEANS AND METHODS FOR INFLUENCING THE STABILITY OF ANTIBODY PRODUCING CELLS

(71) Applicants: ACADEMISCH MEDISCH CENTRUM BIJ DE UNIVERSITEIT VAN AMSTERDAM, Amsterdam (NL); AIMM THERAPEUTICS B.V., Amsterdam (NL)

(72) Inventors: Hergen Spits, Amsterdam Zuidoost (NL); Ferenc A. Scheeren, Amsterdam (NL); Tim Beaumont, Amsterdam Zuidoost (NL); Sean A. Diehl, Shelburne, VT (US)

(73) Assignees: ACADEMISCH MEDISCH CENTRUM BIJ DE UNIVERSITEIT VAN AMSTERDAM, Amsterdam (NL); AIMM THERAPEUTICS B.V., Amsterdam (NL)

(*) Notice: Subject to any disclaimer, the term of this patent is extended or adjusted under 35 U.S.C. 154(b) by 145 days.

(21) Appl. No.: 14/836,335

(22) Filed: Aug. 26, 2015

(65) Prior Publication Data
US 2016/0060598 A1 Mar. 3, 2016

Related U.S. Application Data

(62) Division of application No. 12/086,328, filed as application No. PCT/NL2006/000625 on Dec. 8, 2006, now Pat. No. 9,127,251.

(30) Foreign Application Priority Data

Dec. 9, 2005 (NL) .................. PCT/NL2005/000848
Dec. 6, 2006 (EP) ...................................... 06076211

(51) Int. Cl.
*A61K 38/00* (2006.01)
*C12N 15/63* (2006.01)
*C12N 5/18* (2006.01)
*C12N 5/0781* (2010.01)
*C07K 16/00* (2006.01)

(52) U.S. Cl.
CPC ............ *C12N 5/0635* (2013.01); *C07K 16/00* (2013.01); *C12N 2501/23* (2013.01); *C12N 2501/231* (2013.01); *C12N 2501/2321* (2013.01); *C12N 2501/52* (2013.01); *C12N 2501/60* (2013.01); *C12N 2502/99* (2013.01); *C12N 2510/02* (2013.01); *C12N 2510/04* (2013.01)

(58) Field of Classification Search
None
See application file for complete search history.

(56) References Cited

U.S. PATENT DOCUMENTS

| 4,997,764 | A | 3/1991 | Dalla Favera |
| 5,684,147 | A | 11/1997 | Agrawal et al. |
| 5,849,900 | A | 12/1998 | Moelling |
| 5,866,757 | A | 2/1999 | Reisner et al. |
| 6,001,558 | A | 12/1999 | Backus et al. |
| 7,378,276 | B2 | 5/2008 | Ettinger et al. |
| 7,964,406 | B2 | 6/2011 | Spits et al. |
| 8,247,228 | B2 | 8/2012 | Ettinger et al. |
| 8,318,487 | B2 | 11/2012 | Spits et al. |
| 8,389,281 | B2 | 3/2013 | Spits et al. |
| 2003/0099613 | A1 | 5/2003 | Berkhout et al. |
| 2003/0152559 | A1 | 8/2003 | Yang et al. |
| 2003/0158131 | A1 | 8/2003 | Aldovini et al. |
| 2005/0009180 | A1 | 1/2005 | Yang et al. |
| 2005/0238626 | A1 | 10/2005 | Yang et al. |
| 2008/0274991 | A1 | 11/2008 | Berkhout et al. |
| 2008/0293068 | A1 | 11/2008 | Tsien et al. |
| 2008/0305076 | A1 | 12/2008 | Ettinger |
| 2009/0093024 | A1 | 4/2009 | Bowers et al. |
| 2009/0217403 | A1 | 8/2009 | Spits |
| 2010/0093038 | A1 | 4/2010 | Spits |
| 2010/0113745 | A1 | 5/2010 | Spits et al. |
| 2010/0239593 | A1 | 9/2010 | Spits et al. |
| 2011/0020323 | A1 | 1/2011 | Beaumont et al. |
| 2012/0070446 | A1 | 3/2012 | Beaumont et al. |
| 2012/0151613 | A1 | 6/2012 | Wang et al. |
| 2012/0157662 | A1 | 6/2012 | Beaumont et al. |

FOREIGN PATENT DOCUMENTS

| EP | 1627563 A | 2/2006 |
| EP | 1997830 A1 | 12/2008 |
| GB | 2398783 A | 9/2004 |
| JP | 2007510666 | 4/2007 |
| JP | 2008539794 | 11/2008 |
| JP | 2010528601 | 8/2010 |
| WO | 1989008146 A1 | 9/1989 |
| WO | 1994008004 A1 | 4/1994 |
| WO | 1994017086 A1 | 8/1994 |
| WO | 1994027426 A1 | 12/1994 |
| WO | 1995006409 A1 | 3/1995 |
| WO | 1996001313 A1 | 1/1996 |
| WO | 1996018413 A1 | 6/1996 |
| WO | 2001018185 A1 | 3/2001 |
| WO | 2001020013 A3 | 9/2001 |

(Continued)

OTHER PUBLICATIONS

Barnett, et al., Determination of leucocyte antibody binding capacity (ABC): the need for standardization. Clin. Lab. Haem., 1998, vol. 20, pp. 155-164.

(Continued)

*Primary Examiner* — Michail Belyavskyi
(74) *Attorney, Agent, or Firm* — Gianna J. Arnold; Saul Ewing LLP

(57) ABSTRACT

The invention provides a method for influencing the stability of an antibody producing cell, comprising directly or indirectly influencing the amount of BCL6 and/or Blimp 1 expression product within said antibody producing cell. Stable antibody producing cells and cell lines are also provided, as well as methods for producing antibodies using such cells and/or cell lines.

10 Claims, 23 Drawing Sheets

(56) References Cited

FOREIGN PATENT DOCUMENTS

| | | |
|---|---|---|
| WO | 2003052083 A | 6/2003 |
| WO | 2003079757 A3 | 7/2003 |
| WO | 2003068819 A1 | 8/2003 |
| WO | 2003070193 A3 | 8/2003 |
| WO | 2003050262 A3 | 2/2004 |
| WO | 2004083249 A2 | 9/2004 |
| WO | 2005052139 A2 | 6/2005 |
| WO | 2005052164 A1 | 6/2005 |
| WO | 2005044306 A2 | 9/2005 |
| WO | 2005102383 A1 | 11/2005 |
| WO | 2005123923 A3 | 6/2006 |
| WO | 2006016808 A3 | 8/2006 |
| WO | 2006132524 A1 | 12/2006 |
| WO | 2007067032 A1 | 6/2007 |
| WO | 2007067046 A1 | 6/2007 |
| WO | 2007058527 A3 | 9/2007 |
| WO | 2008147196 A2 | 12/2008 |
| WO | 2011008093 A1 | 1/2011 |
| WO | 2011043643 A1 | 4/2011 |
| WO | 2011008092 A4 | 7/2011 |
| WO | 2012072814 A1 | 6/2012 |
| WO | 2013081463 A2 | 6/2013 |

OTHER PUBLICATIONS

Becker, et al., Generation of Human Antigen-Specific Monoclonal IgM Antibodies Using Vaccinated "Human Immune System" Mice, PLOS ONE, Oct. 4, 2010, vol. 5, No. 10.

Buckland, Blimp1, BCL6, and B-Cell Fate, Nature Reviews Immunology. Sep. 2002, pp. 629-629, vol. 2.

Morrison, et al.,Vectors and Approaches for the Eukaryotic Expression of Antibodies and Anitbody Fusion Proteins, Antibody Engineering, 2nd ed., Chapter 9, pp. 267-293.

Ryvbal'skiy N.G., Serova M.A., Igant'yeva G.A., Starcheus A.P. "Monoklonal'nyye antitela gibribomy" (translation: Monoclonal antibodies and hybridomas), Moskva, Vaskhnil, 1989, pp. 23-44.

Sayegh, et al., E-proteins directly regulate expression of activation-induced deaminase in mature B cells, nature immunology, vol. 4, No. 6, Jun. 2003, pp. 586-593.

Shapiro-Shelef, et al., Blimp-1 Is Required for the Formation of Immunoglobulin Secreting Plasma Cells and Pre-Plasma Memory B Cells, Immunity, Oct. 2003, pp. 607-620, vol. 19.

Diehl, Sean A., et al.; "STAT3-Mediated Up-Regulation of BLIMP1 is Coordinated with BCL6 Down-Regulation to Control Human Plasma Cell Differentiation;" The Journal of Immunology, 2008, vol. 180, pp. 4805-4815.

Christopherson, Karen S., et al.; "Ecdysteroid-dependent regulation of genes in mammalian cells by a *Drosophila* ecdysone receptor and chimeric transactivators;" Proc. Natl. Acad. Sci. USA, Jul. 1992, vol. 89, pp. 5314-6318.

Chipuk, Jerry E., et al.; "How do BCL-2 proteins induce mitochondrial outer membrane permeabilization?;" Cell Press, Trends in Cell Biology; vol. 18, No. 4, pp. 157-164.

Banchereau, Jacques, et al.; "Long-Term Human B Cell Lines Dependent on Interleukin-4 and Antibody to CD40;" Sciences, Jan. 4, 1991, vol. 251, No. 4989, pp. 70-72.

Adams, Jerry M., et al.; "Bcl-2 regulated apoptosis: mechanism and therapeutic potential;" Sciencedirect, Current Opinion in Immunology; 2007, vol. 19, pp. 488-496.

Close, Pauline M., et al.; "Zonal Distribution of Immunoglobulin-Synthesizing Cells Within the Germinal Centre: An In Situ Hybridization and Immunohistochemical Study;" Journal of Pathology, 1990, vol. 162, pp. 209-216.

Liu, Yong-Jun, et al.; "Germinal center development;" Immunological Reviews, 1997, vol. 156, pp. 111-126.

Kinsella, Todd M., et al.; "Episomal Vectors Rapidly and Stably Produce High-Titer Recombinant Retrovirus;" Human Gene Therapy, Aug. 1, 1996, vol. 7; pp. 1405-1413.

Ye, Bihui H., et al.; "The BCL-6 proto-oncogene controls germinal-centre formation and Th2-type inflammation;" Nature Publishing Group, Jun. 16, 1997, vol. 16, pp. 161-170.

Zamore, Phillip D., et al.; "RNAi: Double-Stranded RNA Directs the ATP-Dependent Cleavage of mRNA at 21 to 23 Nucleotide Internals;" Cell, Mar. 31, 2000, vol. 101, pp. 25-33.

Ettinger, Rachel, et al.; "IL-21 Induces Differentiation of Human Naive and Memory B Cells into Antibody-Secreting Plasma Cells;" The Journal of Immunololgoy, 2005, vol. 175, pp. 7867-7879.

Johnson, Syd, et al.; "A Direct Comparison of the Activities of Two Humanized Respiratory Syncytial Virus Monoclonal Antibodies: MEDI-493 and RSHZ19;" The Journal of Infectious Disease, 1999, vol. 180, pp. 35-40.

Smit, Laura A., et al.; "Expression of Activation-induced Cytidine Deaminase is Confined to B-Cell Non-Hodgkin's Lymphomas of Germinal-Center Phenotype;" Cancer Research, Jul. 15, 2003, vol. 63, pp. 3894-3898.

Jung, Daniel, et al.; "Inducible Expression of Bcl-XL Restricts Apoptosis Resistance to the Antibody Secretion Phase in Hybridoma Cultures;" 2002 Wiley Periodicals Inc., pp. 180-187.

Liu, Xinqi, et al.; "The Structure of a Bcl-xL/Bim Fragment Complex: Implications for Bim Function;" Immunity, Sep. 2003, vol. 19, pp. 341-352.

Ning, Zhi-Qiang, et al.; "Distinct mechanisms for rescue from apoptosis in Ramos human B cells by signaling through CD40 and interleukin-4 receptor: role for inhibition of an early response gene;" Eur. J. Immunol., 1996, vol. 26, pp. 2356-2363.

Tey, Beng, et al.; "Effect of Bcl-2 Overexpression on Cell Cycle and Antibody Productivity in Chemostat Cultures of Myeloma NS0 Cells;" Journal of Bioscience and Bioengineering, 2005, vol. 100, No. 3, pp. 303-310.

Yoo, Esther M., et al.; "Myeloma expression systems;" Journal of Immunological Methods, 2002, vol. 261, pp. 1-20.

Baron, Udo, et al.; "Tet-Repressor-Based System for Regulated Gene Expression in Eukaryotic Cells: Principles and Advances:" Methods in Enzymology, vol. 327, pp. 401-421.

Guzman, Luz-Maria, et al.; "Tight Regulation, Modulation, and High-Level Expression by Vectors Containing the Arabinose PBAD Promoter;" Journal of Bacteriology, Jul. 1995, pp. 4121-4130.

Muramatsu, Masamichi, et al.; "Specific Expression of Activation-induced Cytidine Deaminase (AID), a Novel Member of the RNA-editing Deaminase Family in Germinal Center B Cells;" The Journal of Biological Chemistry, Jun. 25, 1999, vol. 274, No. 26, pp. 18470-18476.

Kee, Barbara L.; "E and ID proteins branch out;" Nature Reviews Immunology, Mar. 2009, vol. 9, pp. 175-184.

Kuo, Tracy C., et al.; "Repression of BCL-6 is required for the formation of human memory B cells in vitro;" The Journal of Experimental Medicine, Apr. 16, 2007, vol. 204, No. 4, pp. 819-830.

Lokate, Angelique M.C., et al.; "Biomolecular Interaction Monitoring of Autoantibodies by Scanning Surface Plasmon Resonance Microarray Imaging;" J. Am. Chem. Soc., 2007, vol. 129, pp. 14013-14018.

Malisan, Florence, et al.; "Interleukin-10 Induces Immunoglobulin G Isotype Switch Recombination in Human CD40-Activated Naive B Lymphocytes;" The Journal of Experimental Medicine, Mar. 1996, vol. 183, pp. 937-947.

Maurer, Ulrich, et al.; "Glycogen Synthase Kinase-3 Regulates Mitochondrial Outer Membrane Permeabilization and Apoptosis by Destabilization of MCL-1;" Molecular Cell, Mar. 17, 2006, vol. 21, pp. 749-760.

Ichikawa, H. Travis, et al.; "Structural Phylogenetic Analysis of Activation-Induced Deaminase Function;" The Journal of Immunology, 2006, vol. 177, pp. 355-361.

Peled, Jonathan U., et al.; "The Biochemistry of Somatic Hypermutation;" Annu. Rev. Immunol, 2008, vol. 26, pp. 481-511.

Gossen, Manfred, et al.; "Tight control of gene expression in mammalian cells by tetracycline-responsive promoters;" Proc. Natl. Acad. Sci. USA, Jun. 1992, vol. 89, pp. 5547-5551.

Rousset, Francaise, et al.; "Interleukin 10 is a potent growth and differentiation factor for activated human B lymphocytes;" Proc. Natl. Acad. Sci. USA, Mar. 1992, vol. 89, pp. 1890-1893.

(56) References Cited

OTHER PUBLICATIONS

Dadgostar, Hajir, et al.; "Cooperation of multiple signaling pathways in CD40-regulated gene expression in B lymphocytes;" PNAS, Feb. 5, 2002, vol. 99, No. 3, pp. 1497-1502.
Sidwell, Robert W., et al.; "Respiratory syncytial virus infections: Recent prospects for control;" Sciencedirect, Antiviral Research, 2006, vol. 71, pp. 379-390.
Spits, Hergen, et al.; "Id2 and Id3 Inhibit Development of CD34 Stem Cells into Predendritic Cell (Pre-DC)2 but Not into Pre-DC1: Evidence for a Lymphoid Origin of Pre-DC2;" J. Exp. Med., Dec. 18, 2000, vol. 192, No. 12, pp. 1775-1783.
Thompson, William W., et al.; "Mortality Associated With Influenza and Respiratory Syncytial Virus in the United States;" American Medical Association, Jan. 8, 2003, vol. 289, No. 2, pp. 179-186.
Hall, Caroline Breese, et al.; "The Burden of Respiratory Syncytial Virus Infection in Young Children;" The New England Journal of Medicine, Feb. 5, 2009, vol. 360, pp. 588-598.
Good, Kim L., et al.; "Kinetics of Human B Cell Behavior and Amplification of Proliferative Responses following Stimulation with IL-21;" The Journal of Immunology, 2006, vol. 177, pp. 5236-5247.
Ettinger, Rachel, et al.; "IL-21 is a Pivotal Cytokine in the Induction of TCell-Dependent B Cell Activation, Differentiation and IG Secretion;" GARN 2005 Novel Therapeutic Targets and Strategies, Section 107.
Shvarts, et al., A senescence rescue screen identifies BCL6 as an inhibitor of anti-proliferative p19ARF-p53 signaling, Genes and Development, vol. 16, No. 2, Mar. 15, 2002, pp. 681-686.
Tosata, et al., Identification of Interleukin-6 as an Autocrine Growth Factor for Epstein-Barr Virus-Immortalized B Cells, Journal of Virology, Jun. 1990, vol. 64, No. 6, pp. 3033-3041.
Ahmad, et al., Mechanism of SMRT Corepressor Recruitment by the BCL6 BTB Domain, Molecular Cell, Dec. 2003, vol. 12, pp. 1551-1564.
Liu, et al., The Structure of a Bcl-xL/Bim Fragment Complex: Implications for Bim Function, Immunity, Sep. 2003, vol. 19, pp. 341-352.
Petros, et al., Rationale for Bcl-xL/Bad Peptide Complex Formation From Structure, Mutageneis, and Biophysical Studies, Protein Science, 2000, vol. 9, pp. 2528-2534, Cambridge University Press, USA.
Manion, et al., Bcl-xL Mutations Suppress Cellular Sensitivity to Antimycin A, The Journal of Biological Chemistry, 2004, vol. 279, No. 3, pp. 2159-2165.
Kriangkum, et al., Impaired class switch recombination (CSR) in Waldenstrom macroglobulinemia (WM) despite apparently normal CSR machinery, Blood, Apr. 1, 2006, vol. 107, pp. 2920-2927.
Eppeldegui, et al., Infection of Human B Cells with Epstein-Barr Virus Results in the Expression of Somatic Hypermutation-Inducing Molecules and in the Accrual of Oncogene Mutations, Molecular Immunology, Feb. 1, 2007, vol. 44, No. 5, Pergamon, GB.
Gil, et al., Somatic Mutations and Activation-Induced Cytidine Deaminase (AID) Expression in Established Rheumatoid Factor-Producing Lymphoblastoid Cell Line, Molecular Immunology, Jan. 1, 2007, vol. 44, No. 4, pp. 494-505, Pergamon, GB.
Koff, Vaccine, vol. 30 (2012), pp. 4310-4315.
Lee, et al., Regulation of the Germinal Center Gene Program by interferon (IFN) Regulatory Factor 8/IFN Consensus Sequence-Binding Protein, Journal of Experimental Medicine, Jan. 2006, vol. 203, No. 1, pp. 63-72.
Muramatsu, et al., Class Switch Recombination and Hypermutation Require Activation-Induced Cytidine Deaminase (AID), a Potential RNA Editing Enzyme, Cell, Sep. 1, 2000, vol. 102, No. 5, pp. 553-563.
Roughan, et al., The Intersection of Epstein-Barr Virus with the Germinal Center, Journal of Virology, Apr. 15, 2009, vol. 83, No. 8, pp. 3968-3976. The American Society of Microbiology, US.

Schaft, et al., Peptide fine specificity of anti-glycoprotein 100 CTL is preserved following transfer of engineered TCRαβ genes into primary human T lymphocytes, The Journal of Immunology, 2003, 170, pp. 2186-2194.
Tan, et al., Zinc-finger Protein-Targeted Gene Fegulation, Genomewide Single-Gene Specificity, Proceedings of the National Academy of Sciences of the United States of America, Oct. 14, 2003, vol. 100, No. 21, pp. 11997-12002.
Toyama, et al., Memory B Cells Without Somatic Hypermutation Are Generated From Bcl6-Deficient B Cells, Immunity, Sep. 1, 2002, vol. 17, No. 3, pp. 329-339, Cell Press, US.
Vanregenmortel, Arch. Virol., vol. 157 (2012), pp. 1-20.
Knodel, et al., Abstract, Blimp-1 over-expression abrogates IL-4 and CD40-mediated suppression of terminal B cell differentiation but arrests isotype switching. European Journal of Immunology, 2001, vol. 31, No. 7, pp. 1972-1980.
Mathas, et al., Abstract, Intrinsic inhibition of transcription factor E2A by HLH proteins ABF-1 and Id2 mediates reprogramming of neplastic B cells in Hodgkin lymphoma. Nature Immunology, Feb. 2006, vol. 7, No. 2, pp. 207-215.
Mehta, et al., IL-21 induces the apoptosis of resting and activated primary B cells. Journal of Immunology, Apr. 15, 2003, vol. 170, No. 8, pp. 4111-4118. The Williams and Wilkins Co., Baltimore, MD, US.
Das, et al., Viral evolution as a tool to improve the tetracycline-regulated gene expression system. The Journal of Biological Chemistry, Apr. 30, 2004, vol. 279, No. 18, pp. 18776-18782.
Gimeno, et al., Monitoring the effect of gene silencing by RNA interference in human CD34+ cells injected into newborn RAG2<-1>/gamma/c<-1>mice: functional inactivation of p53 in developing T cells. Blood, Dec. 15, 2004, vol. 104, No. 13, pp. 3886-3893, US.
Goldman, et al., Enhanced human cell engraftment in mice deficient in RAG2 and the common cytokine receptor gamma chain. British Journal of Haematology, Nov. 1998, vol. 103, No. 2, pp. 335-342, Oxford, GB.
Gossen, et al., Abstract, Transcriptional Activation by Tetracyclines in Mammalian Cells. Science, Jun. 23, 1995, vol. 268, pp. 1766-1769, American Association for the Advancement of Science, US.
Kang, et al., Long-term expression of a T-cell receptor beta-chain gene in mice reconstituted with retrovirus-infected hematopoietic stem cells. Proc. Natl Acad. Sci., Dec. 1990, vol. 87, pp. 9803-9807, National Academy of Science, Washington, DC, US.
Knott, et al., Tetracycline dependent Gene Reguiation: Combinations of Transregulators Yield of a Variety of Expression Windows, Biotechniques, 2002, vol. 32, No. 4, pp. 796-806, Informa Life Sciences Publishing, Westborough, MA, US.
Kobayashi, et al., Abstract: Prevention of acute liver failure in rats with reversibly immortalized human hepatocytes, Science, Feb. 18, 2000, vol. 287, No. 5456, pp. 1258-1262, Washington, DC, US.
Krueger, et al., Single-chain Tet Transregulators. Nucleic Acids Research, Jun. 15, 2003, vol. 31, No. 12, pp. 3050-3056, Oxford University Press, Surrey, GB.
Kyba, et al., Enhanced hematopoietic differentiation of embryonic stem cells conditionally expressing Stat5. PNAS, 2003, vol. 100, pp. 1-12.
Mulloy, et al., Maintaining the self-renewal and differentiation potential of human CD34 + hematopoietic cells using a single genetic element. Blood, Dec. 15, 2003, vol. 102, No. 13, pp. 4369-4376.
PCT International Search Report, PCT/NL2005/000581, dated Jul. 4, 2006.
Ozaki, et al., Regulation of B cell differentiation and plasma cell generation by IL-21, a novel inducer of Blimp-1 and Bcl-6. Journal of Immunology, Nov. 1, 2004, vol. 173, No. 9, pp. 5361-5371.
Schvarts, et al., A senescence rescue screen identifies BCL6 as an inhibitor of anti-proliferative p19ARF-p53 signaling. Genes and Development, Mar. 15, 2002, vol. 16, No. 6, pp. 681-686.
Shaffer, et al., Blimp-1 orchestrates plasma cell differentiation by extinguishing the mature B cell gene expression program. Immunity, Jul. 2002, vol. 17, No. 1, pp. 51-62.
Shen Chun-Pyn, et al., B-cell-specific DNA binding by an E47 homodimer. Molecular and Cellular Biology, 1995, vol. 15, No. 8, pp. 4518-4524.

(56) References Cited

OTHER PUBLICATIONS

Traggiai, et al., Abstract: An efficient method to make human monoclonal antibodies from memory B cells: potent neutralization of SARS conoranavirus. Nature Medicine, Aug. 2004, vol. 10. No. 8, pp. 871-875.

Yamochi, et al., Adenovirus-mediated high expression of BCL-6 CV-1 cells induces apoptotic cell death accompanied by down-regulation of BCL-2 and BCL-XL. Oncogene, Jan. 14, 1999, vol. 18, No. 2, pp. 487-494.

Alajez, et al., Therapeutic potential of a tumor-specific, MHC-unrestricted T-cell receptor expressed on effector cells of the innate and the adaptive immune system through bone marrow transduction and immune reconstitution. Blood, Jun. 15, 2005, vol. 105, No. 12, pp. 4583-4589.

Chlewicki, et al., High-affinity, Peptide-specific T Cell Receptors can be Generated by Mutations in CDR1, CDR2 or CDR3, J. Mol. Biol, 2005, vol. 346, pp. 223-239.

Clay, et al., Efficient Transfer of a Tumor Antigen-Reactive TCR to Human Peripheral Blood Lymphocytes Confers Anti-Tumor Reactivity. Journal of Immunology, 1999, vol. 163, pp. 507-513. The Williams and Wilkins Co., Baltimore, MD, US.

Clay, et al, Potential Use of T Cell Receptor Genese to Modify Hematopoietic Stem Cells for the Gene Therapy of Cancer. Pathology Oncology Research, 1999, vol. 5, No. 1, pp. 3-15, Budapest, Hungary.

Das, et al., Abstract. A Conditionally Replicating Virus as a Novel Approach Toward an HIV Vaccine. Methods in Enzymology, 2004, vol. 388, pp. 359-379. Academic Press, San Diego, CA, US.

PCT International Search Report, PCT/NL2005/000739, dated Nov. 29, 2006.

PCT International Search Report, PCT/NL2005/000848, dated Jul. 10, 2006.

PCT International Search Report, PCT/NL2006/000277, dated Sep. 1, 2006.

PCT International Search Report, PCT/NL2006/000575, dated Jul. 27, 2007.

Petrie, et al., T Cell Receptor Gene Recombination Patterns and Mechanisms: Cell Death, Rescue, and T Cell Production. J. Exp. Med., 1995, vol. 182, pp. 121-127.

Salucci, et al., Tight control of gene expressions by a helper-dependent adenovirus vector carrying the rtTA2s-M2 tetracycline transactivator and repressor systems. Gene Therapy, 2002, vol. 9, pp. 1415-1421, Macmillam Press Ltd., Basingstoke, GB.

Schuringa, et al., Constitutive activation of STAT5A promotes human hematopoietic stem cell self-renewal and erythroid differentiation. Journal of Experimental Medicine, Sep. 6, 2004, vol. 200, No. 5, pp. 623-635.

Schuringa, et al., Enforced activation of STAT5A Facilitates the Generation of Embryonic Stem-Derived Hematopoietic Stem Cells That Contribute to Hematopoietic In Vivo. Stem Cells, 2004, vol. 22, pp. 1191-1204.

Stier, et al., Notch 1 activation increases hematopoietic stem cell self-renewal in vivo and favors lymphoid over myeoid lineage outcome. Blood, Apr. 1, 2002, vol. 99, No. 7, pp. 2369-2378.

Traggiai, et al., Abstract: Development of a human adaptive immune system in cord blood cell-transplanted mice. Science, Apr. 2, 2004, vol. 304, No. 5667, pp. 104-107, Washington, DC, US.

Urlinger, et al., Exploring the sequence space for the tetracycline-dependent transcriptional activators, novel mutations yield expanded range and sensitivity. Proceedings of the National Academy of Sciences of USA, Jul. 5, 2000, vol. 97, No. 14, pp. 7963-7968, National Academy of Science, Washington, DC, US.

Vickers, et al., Efficient reduction of target RNAs by small interfering RNA and RNase H dependent antisense agents. The Journal of Biological Chemistry, 2003, vol. 278, pp. 7108-7118.

Weijer, et al., Intrathymic and extrathymic development of human plasmacytoid dendritic cell precursors in vivo. Blood, 2002, vol. 99, pp. 2752-2759.

Yang, et al., Generation of Functional antigen-specific T Cells in defined genetic backgrounds by retrovirus-mediated expression of TCR-cDNAs in hematopoietic precursor cells. Proceedings of the National Academy of Sciences of USA, Apr. 30, 2002, vol. 99, No. 9, pp. 6204-6209, National Academy of Science, Washington, DC, US.

Yang, et al., Long-term in vivo provision of antigen-specific T cell immunity by programming of hematopoietic stem cells. Proceedings of the National Academy of Sciences of USA, Mar. 22, 2005, vol. 102, pp. 4518-4523, National Academy of Science, Washington, DC, US.

Zhou, et al., Improved single-chain transactivators of the Tet-On gene expression system. Biotechnology. 2007, vol. 7, p. 6.

Zhou, et al., Modification of the Tet-On regulatory system prevents the conditional-live HIV-1 variant from losing doxycycline-control. Retrovirology, 2006, vol. 3, p. 82.

Zhou, et al., Optimization of the Tet-On system fro regulated gene expression through viral evolution. Gene Therapy, Oct. 2006, vol. 13, No. 19, pp. 1382-1390.

Zhou, et al., The genetic stability of a conditional live HIB-1 variant can be improved by mutations in the Tet-On regulatory system that restrain evolution. The Journal of Biological Chemistry, Jun. 23, 2006, vol. 281, No. 25, pp. 17084-17091.

Office Action for U.S. Appl. No. 10/097,542, dated Feb. 9, 2009.
Office Action for U.S. Appl. No. 11/665,510, dated Mar. 11, 2009.
PCT International Search Report, PCT/NL2006/000625, dated Apr. 10, 2007.

Eaton, et al., Gene Therapy, 2002, vol. 9, pp. 527-535.
Park, Hong-Jai, et al., Insights into the Role of Follicular Helper T Cells in Autoimmunity, Immune Network, vol. 14, No. 1 pp. 21-29, Feb. 2014.

Shaffer, A.L., et al., Lymphoid Malignancies: The Dark Side of B-Cell Differentiation, Nature Reviews, Immunology, vol. 2, pp. 1-13, Dec. 2002.

Notice of opposition to a European Patent for EP Patent No. 1974017 printed Aug. 7, 2014.

Facts and arguments for European Patent for EP Patent No. 1974017 printed Aug. 7, 2014, contains lists of citations.

Communication of a notice of opposition for EP Patent No. 1974017 dated Aug. 12, 2014.

Scheeren et al. STAT5 regulates the self-renewal capacity and differentiation of human memory B cells and controls Bcl-6 expression. Nature Immunology, 2005, pp. 303-313, vol. 6.

Boise et al., bcl-x, a bcl-2-Related Gene That Functions as a Dominant Regulator of Apoptotic Cell Death, Cell, Aug. 27, 1983, pp. 597-608, vol. 74.

Grillot et al., bcl-x Exhibits Regulated Expression During B Cell Development and Activation and Modulates Lymphocyte Survival in Transgenic Mice, The Journal of Experimental Medicine, Feb. 1996, pp. 381-391, vol. 183.

Zhang et al., Up-Regulation of Bcl-XL Expression Protects CD40-Activated Human B Cells from Fas-Mediated Apoptosis. Cellular Immunology, 1996, pp. 149-154, vol. 173.

Solvason et al., Transgene Expression of bcl-xL Permits Anti-immunoglobulin (Ig)-induced Proliferation in xid B Cells, J. Exp. Med., 1998, pp. 1081-1091, vol. 187.

Charbonneau et al., Prolongation of murine hybridoma cell survival in stationary batch culture by Bcl-xL expression, Cytotechnology, 2000, pp. 131-139, vol. 34.

Jung et al., Inducible Expression of Bcl-XL Restricts Apoptosis Resistance to the Antibody Secretion Phase in Hybridoma Cultures, Biotechnology and Bioengineering, pp. 180-187, vol. 79.

Turner et al., Blimp-1, a Novel Zinc Finger-Containing Protein That Can Drive the Maturation of B Lymphocytes into Immunoglobulin-Secreting Cells, Cell, Apr. 22, 1994, pp. 297-306, vol. 77.

Lin et al., Blimp-1-Dependent Repression of Pax-5 Is Required for Differentiation of B Cells to Immunoglobulin M-Secreting Plasma Cells, Molecular and Cellular Biology, Jul. 2002, pp. 4771-4780, vol. 22, No. 13.

Sciammas et al., Modular Nature of Blimp-1 in the Regulation of Gene Expression during B Cell Maturation, The Journal of Immunology, 2004, pp. 5427-5440, vol. 172.

(56) References Cited

OTHER PUBLICATIONS

Abstract of Ettinger presentation at GARN 2005, Sep. 15-18, Vienna, Austria.
Shapiro-Shelef et al., Blimp-1 Is Required for the Formation of Immunoglobulin Secreting Plasma Cells and Pre-Plasma Memory B Cells, Immunity, Oct. 2003, pp. 607-620, vol. 19.
Reljic et al., Suppression of Signal Transducer and Activator of Transcription 3-dependent B Lymphocyte Terminal Differentiation by BCL-6, J. Exp. Med., Dec. 18, 2000, pp. 1841-1847, vol. 192, The Rockefeller University Press.
Dimitrov, Jordan, et al., Thermodynamic stability contributes to immunoglobulin specificity, Trends in Biochemical Sciences, vol. 39, No. 5, May 1, 2014, pp. 221-226.
Klein, Florian, et al., Somatic Mutations of the Immunoglobulin Framework are Generally Required for Broad and Potent HIV-1 Neutralization, Cell, vol. 153, No. 1, Mar. 28, 2013, pp. 126-138.
Kwakkenbos, Mark, et al., Genetic manipulation of B cells for the isolation of rare therapeutic antibodies from the human repertoire, Methods, Academic Press, vol. 65, No. 1, Jan. 1, 2014, pp. 38-43.
McConnell, Audrey, et al., An intergrated approach to extreme thermostabilization and affinity maturation of an antibody, Protein Engineering Design and Protection, vol. 26, No. 2, Feb. 1, 2013, pp. 151-164.
Wang, Feng, et al., Somatic hypermutation maintains antibody thermodynamic stability during affinity maturation, Proceedings of the National Academy of Sciences, vol. 110, No. 11, Mar. 12, 2013, pp. 4261-4266.

Long-term growth of BCL-XL and BCL6-transduced B cells

IL-21 increased proliferation of B cells transduced with BCL-XL, BCL6, or BCL-XL+BCL6 double transduced cells.

Long-term cultures are EBV−

Doubling time of BCL-XL, BCL6, and BCL-XL-BCL6 double transduced cells.

MEANS AND METHODS FOR INFLUENCING THE STABILITY OF ANTIBODY PRODUCING CELLS

CROSS-REFERENCE TO RELATED APPLICATIONS

This application claims priority to U.S. application Ser. No. 12/086,328, filed on Dec. 7, 2009; to PCT/NL2006/000625, filed on Dec. 8, 2006, and to PCT/NL2005/000848 filed on Dec. 9, 2005, the contents of each of which are incorporated in its respective entirety.

SUMMARY OF THE INVENTION

The following presents a simplified summary in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

The present invention provides a method for influencing the stability of an antibody producing cell, comprising directly or indirectly influencing the amount of BCL6 and/or Blimp 1 expression product within the antibody producing cell. Stable antibody producing cells and cell lines are also provided, as well as methods for producing antibodies using such cells and/or cell lines.

It is an object of the present invention to provide a method for influencing the stability of an antibody producing cell, the method comprising: directly or indirectly influencing BCL6 and/or Blimp-1 expression product amount(s) within the antibody producing cell.

It is a further object of the present invention to provide such a method, wherein the replicative life span of the antibody producing cell is increased in comparison to the antibody producing cell not so directly or indirectly influenced.

It is a further object of the present invention to provide such a method, wherein BCL6 and Blimp-1 are co-expressed in the antibody producing cell.

It is a further object of the present invention to provide such a method, wherein influencing the antibody producing cell comprises: providing the antibody producing cell with a compound capable of directly or indirectly enhancing BCL6 expression; and/or culturing the antibody producing cell together with a compound capable of directly or indirectly enhancing BCL6 expression.

It is a further object of the present invention to provide such a method, wherein influencing the antibody producing cell comprises providing the antibody producing cell with a nucleic acid sequence encoding BCL6 or a functional part, derivative and/or analogue thereof able to influence the amount of BCL6 and/or Blimp-1 expression product.

It is a further object of the present invention to provide such a method, wherein the compound comprises STAT5 or a functional part, derivative and/or analogue thereof capable of directly or indirectly enhancing BCL6 expression.

It is a further object of the present invention to provide such a method, wherein influencing the antibody producing cell comprises: providing the antibody producing cell with a compound capable of directly or indirectly influencing Blimp-1 expression; and/or culturing the antibody producing cell together with a compound capable of directly or indirectly influencing Blimp-1 expression.

It is a further object of the present invention to provide such a method, wherein the compound comprises: STAT3 or a functional part, derivative and/or analogue thereof capable of directly or indirectly influencing Blimp-1 expression, and/or a compound capable of directly or indirectly activating STAT3 and/or a compound capable of directly or indirectly enhancing expression of STAT3.

It is a further object of the present invention to provide such a method, wherein the compound comprises IL-21, IL-2, IL-6, IL-7, IL-10, IL-15, IL-27, a SOCS protein, one of the E-proteins E47, E12, E2-2 or HEB, a mutated Janus kinase and/or a nucleic acid sequence encoding STAT3 or a functional part, derivative and/or analogue thereof capable of directly or indirectly influencing Blimp-1 expression.

It is a further object of the present invention to provide such a method, further comprising providing the antibody producing cell with an additional immortalizing agent.

It is a further object of the present invention to provide such a method, wherein the immortalizing agent comprises a transforming agent.

It is a further object of the present invention to provide such a method, wherein the immortalizing agent comprises Epstein-Barr virus.

It is a further object of the present invention to provide such a method, wherein the antibody producing cell is cultured together with IL-21 before the antibody producing cell is provided with a compound capable of directly or indirectly enhancing BCL6 expression, a nucleic acid sequence encoding BCL6 or a functional part, derivative and/or analogue thereof, and/or a nucleic acid sequence encoding STAT5 or a functional part, derivative and/or analogue thereof capable of directly or indirectly enhancing BCL6 expression.

It is a further object of the present invention to provide such a method, wherein the antibody producing cell is cultured together with IL-21 and provided with Epstein-Barr virus.

It is a further object of the present invention to provide such a method, further comprising: directly or indirectly increasing Bcl-xL expression product amount within the antibody producing cell.

It is a further object of the present invention to provide such a method, wherein increasing the amount of Bcl-xL expression product within the antibody producing cell comprises: providing the antibody producing cell with a nucleic acid sequence encoding Bcl-xL or a functional part, derivative and/or analogue thereof able to increase the amount of Bcl-xL expression product within the antibody producing cell.

It is a further object of the present invention to provide such a method, wherein increasing the amount of Bcl-xL expression product within the antibody producing cell comprises: providing the antibody producing cell with a compound capable of directly or indirectly enhancing Bcl-xL expression, APRIL, BAFF, CD40, BCR stimulation, cytokines, growth factors, downstream effectors, JNK and/or AKT (PKB).

It is a further object of the present invention to provide a method for producing an antibody producing cell that is stable for at least one week, the method comprising: providing a B cell; increasing an expression level of Blimp-1 in the B cell; and increasing and/or maintaining a BCL6 expression level in the B cell.

It is a further object of the present invention to provide such a method, wherein the BCL6 expression level in the cell is brought to, and/or maintained at, essentially the same level or at a higher level as compared to a plasmablast.

It is a further object of the present invention to provide such a method, comprising: providing the B cell with a compound capable of directly or indirectly enhancing Blimp-1 expression and/or culturing the memory B cell together with a compound capable of directly or indirectly enhancing Blimp-1 expression; and providing the B cell with a compound capable of directly or indirectly enhancing BCL6 expression, and/or culturing the B cell together with a compound capable of directly or indirectly enhancing BCL6 expression.

It is a further object of the present invention to provide such a method, wherein the compound is capable of directly or indirectly enhancing Blimp-1 expression comprises IL-21, IL-2, IL-6, 11-7, IL-10, IL-15, IL-27, a SOCS protein, E-protein E47, E12, E2-2 or HEB, a mutated Janus kinase and/or a nucleic acid sequence encoding STAT3 or a functional part, derivative and/or analogue thereof capable of directly or indirectly enhancing Blimp-1 expression.

It is a further object of the present invention to provide such a method, wherein the compound is capable of directly or indirectly enhancing BCL6 expression comprises: a nucleic acid sequence encoding BCL6 or a functional part, derivative and/or analogue thereof capable of directly or indirectly enhancing Blimp-1 expression, and/or a nucleic acid sequence encoding STAT5 or a functional part, derivative and/or analogue thereof capable of directly or indirectly enhancing Blimp-1 expression, and/or a compound capable of directly or indirectly activating STAT5, and/or a compound capable of directly or indirectly enhancing expression of STAT5.

It is a further object of the present invention to provide such a method, further comprising increasing an expression level of Bcl-xL in the cell.

It is a further object of the present invention to provide such a method, comprising providing the B cell with a compound capable of directly or indirectly enhancing Bcl-xL expression.

It is a further object of the present invention to provide such a method, wherein the compound capable of directly or indirectly enhancing Bcl-xL expression comprises a nucleic acid encoding Bcl-xL or a functional part, derivative and/or analogue thereof capable of directly or indirectly enhancing Bcl-xL expression.

It is a further object of the present invention to provide such a method, wherein the compound capable of directly or indirectly enhancing Bcl-xL expression comprises APRIL, BAFF, CD40, BCR stimulation, cytokines, growth factors, downstream effectors, JNK and AKT (PKB).

It is a further object of the present invention to provide such a method, wherein expression of nucleic acid sequence encoding BCL6, STAT5, STAT3, Bcl-xL or a functional part, derivative and/or analogue of BCL6, STAT5 and/or STAT3 and/or Bcl-xL is regulated by an activator and/or repressor that is inducible by an exogenous corn pound.

It is a further object of the present invention to provide such a method, comprising: providing a B cell; providing the B cell with BCL6 and/or STAT5, or a functional part, derivative and/or analogue thereof; providing the B cell with Epstein Barr Virus; and culturing the B cell.

It is a further object of the present invention to provide such a method, comprising: testing a plurality of B cells for a specificity for a given antigen; selecting at least one B cell with a specificity for the given antigen; providing the selected B cell with exogenous BCL6 and/or STAT5, or a functional part, derivative and/or analogue thereof; selecting a B cell comprising exogenous BCL6 and/or STAT5, or a functional part, derivative and/or analogue thereof; and providing the selected B cell with Epstein Barr Virus.

It is a further object of the present invention to provide such a method, wherein the B cell is cultured together with IL-21.

It is a further object of the present invention to provide such a method, wherein the B cell is cultured together with IL-21 before BCL6 and/or STAT5, or a functional part, derivative and/or analogue thereof, is introduced into the B cell.

It is a further object of the present invention to provide such a method, further comprising the B cell with Bcl-xL or a functional part, derivative and/or analogue thereof.

It is a further object of the present invention to provide such a method, wherein an antibody producing cell is cultured that is stable for at least six months.

It is a further object of the present invention to provide such a method, wherein the antibody producing cell is capable of producing antibodies against an antigen of interest.

It is a further object of the present invention to provide such a method, wherein the antibody producing cell has been obtained from an individual, which individual had been previously exposed to the antigen of interest.

It is a further object of the present invention to provide such a method, further comprising expressing a gene of the B cell encoding the Ig heavy chain and/or Ig light chain in a second cell.

It is a further object of the present invention to provide an isolated antibody producing cell that is stable for at least nine weeks.

It is a further object of the present invention to provide an isolated antibody producing cell, comprising a compound that is capable of directly or indirectly influencing expression of BCL6.

It is a further object of the present invention to provide an isolated antibody producing cell, comprising an exogenous nucleic acid sequence encoding BCL6 or a functional part, derivative and/or analogue thereof, and/or an exogenous nucleic acid sequence encoding STAT5 or a functional part, derivative and/or analogue thereof and optionally an exogenous nucleic acid sequence encoding Bcl-xL or a functional part, derivative and/or analogue thereof.

It is a further object of the present invention to provide an isolated antibody producing cell comprising a compound that is capable of directly or indirectly influencing expression of Blimp-1.

It is a further object of the present invention to provide an isolated antibody producing cell comprising an exogenous nucleic acid sequence encoding STAT3 or a functional part, derivative and/or analogue thereof.

It is a further object of the present invention to provide an isolated antibody producing cell, wherein expression of nucleic acid sequence encoding BCL6, STAT5, STAT3, Bcl-xL or a functional part, derivative and/or analogue of BCL6, STAT5 and/or STAT3 and/or Bcl-xL is regulated by an activator and/or repressor that is inducible by an exogenous compound.

It is a further object of the present invention to provide an isolated antibody producing cell comprising: an immortalizing agent; and a compound that is capable of directly or indirectly influencing the amount of BCL6 expression product in the antibody producing cell and/or a compound that is capable of directly or indirectly influencing the amount of Blimp-1 expression product in the antibody producing cell and/or a compound which is capable of directly or indirectly influencing the amount of Bcl-xL expression product in the antibody producing cell.

It is a further object of the present invention to provide an isolated antibody producing cell, comprising Epstein Barr virus and exogenous BCL6, or a functional part, derivative and/or analogue thereof.

It is a further object of the present invention to provide an isolated antibody producing cell, comprising Epstein Barr virus and exogenous STAT5, or a functional part, derivative and/or analogue thereof.

It is a further object of the present invention to provide a method for producing a B cell line comprising: obtaining a stable antibody producing cell with the method according to claim 1, and culturing the antibody producing cell ex vivo.

It is a further object of the present invention to provide a method for producing a B cell line comprising: obtaining a memory B cell and/or a naive B cell from an individual who has been exposed to an antigen of interest, producing an antibody producing cell that is stable for at least one week, using the B cell obtained from the individual in the method according to claim 1, and culturing the antibody producing cell ex vivo.

It is a further object of the present invention to provide a method for producing a B cell line, further comprising harvesting antibodies produced by the antibody producing cell.

It is a further object of the present invention to provide a method for producing antibodies capable of specifically binding an antigen of interest, the method comprising: obtaining a memory B cell and/or a naive B cell capable of differentiating into a B cell which B cell produces antibodies capable of specifically binding the antigen of interest, producing an antibody producing cell that is stable for at least one week using the B cell in the method according to claim 1, and obtaining antibodies produced by the antibody producing cell.

It is a further object of the present invention to provide a method for producing antibodies, further comprising culturing the antibody producing cell ex vivo.

It is a further object of the present invention to provide a method for producing an antibody producing cell that is stable for at least one week, further comprising expressing a gene of the B cell encoding the Ig heavy chain and/or Ig light chain in a second cell.

It is a further object of the present invention to provide an antibody, wherein the antibody is produced by the methods disclosed herein.

DESCRIPTION

Ex vivo cell cultures are important tools in current biological and medical applications. One important application is culturing antibody producing cells in order to harvest antibodies, preferably, monoclonal antibodies. Monoclonal antibodies (mAbs) represent multiple identical copies of a single antibody molecule which copies bind to antigens with the same affinity and promote the same effector functions. Amongst the benefits of mAbs is their specificity for the same epitope on an antigen. This specificity confers certain clinical advantages on mAbs over more conventional treatments while offering patients an effective, well tolerated therapy option with generally low side effects. Moreover mAbs are useful for biological and medical research The proliferative capacity of most primary cells in culture is limited by the induction of senescence. This state of irreversible growth-arrest is characterized by expression of a number of senescence-associated markers, such as senescence-associated beta-galactosidase, plasminogen-activator inhibitor 1 (PAI-1), p19.sup.ARF, p53, p21.sup.CIP1, and p16.sup.INK4A. In order to provide a proliferating cell line, cells are often fused to cancer cells in order to produce hybridoma cells. The resulting hybridoma cells are capable of dividing indefinitely and grow well in cell culture. Individual hybridomas with a desired characteristic can then be selected for a given purpose.

In order to directly obtain human monoclonal antibodies with a desired specificity it would be convenient to isolate a B cell capable of producing such antibody and to culture the B cell ex vivo. However, hybridoma technology with human B cells has not been very successful because the resulting hybridomas are unstable. Many attempts for ex vivo culturing of B cells have been undertaken. It is well documented that human naive and memory B cells can be cultured for a limited period following engagement of CD40 in the presence of cytokines, including IL-2, IL-4 and IL-10 (Banchereau et al., 1991) and it is believed that this system mimics the in vivo response of B cells towards cognate antigen primed CD40L-expressing helper T cells. In the absence of CD40 ligation, IL-10 alone or in combination with IL-2 induces differentiation into antibody-producing cells (Malisan et al., 1996). The mechanisms of regulation of survival and proliferation of mature B cells cultured under these conditions are only partly known.

Engagement of CD40 on B cells has multiple effects including protection againsfapoptosis, (partial) inhibition of differentiation and induction of cytokine responsiveness by B cells. Expression of a large number of cell cycle inhibitors was decreased by CD40 engagement including Rb-1 and Rb-2 (Dadgostar et al., 2002) and it is likely that downregulation of such genes release resting B cells from quiescence. Although CD40 triggering leads to a brief proliferative response, cytokines are instrumental in sustaining cell cycle progression of the triggered B cells. IL-2 and IL-4 are the most efficient cytokines that promote continued cell cycle progression of CD40 or surface Ig-stimulated B cells. Yet, B cell cultures described in the above mentioned papers are only stable during a limited period.

Another approach for immortalizing B cells is Epstein-Barr virus (EBV) transformation. However the frequency of B cells that are transformed by EBV is low and therefore attempts to generate EBV transformed B cells that produce desired antibodies have met with little success. Recently, Traggiai et al have reported a method for more efficient Epstein-Barr virus transformation of human B cells that increased the frequency of B cells that were transformed. With this method B cells obtained from a patient who recovered from severe acute respiratory syndrome coronavirus (SARS-CoV) infection were transformed with EBV and transformed B cell clones that produce monoclonal antibodies specific for SARS and other viral proteins were isolated (Traggiai et al, 2004).

Yet another approach for immortalizing B cells is described in patent application WO 03/052083. This application describes a method of stabilizing B cells wherein human B cells are transduced with constitutively active signal transducer of activation and transcription (CA-STAT). A prolonged life span of B cells was observed. Replicating B cells were however not capable of producing antibody at the same time. Antibodies could be obtained by halting the replication of the cells, thereby bringing about terminal differentiation. The terminally differentiated cells produced antibody during a restricted time, after which the differentiated cells died. However, the replicating B cells of WO 03/052083 lose their capability of developing into antibody producing cells after culturing of 1.5-2 months or longer, rendering these B cell cultures unsuitable for antibody production.

Although various approaches for culturing antibody producing cells have been described, there is still a need for means and methods for influencing the stability of antibody producing cells. It is an object of the present invention to provide such means and methods.

Accordingly the invention provides a method for influencing the stability of an antibody producing cell, comprising directly or indirectly influencing the amount of BCL6 and/or Blimp-1 expression product within said antibody producing cell. Preferably the amounts of both BCL6 and Blimp-1 expression products within said antibody producing cell are regulated, since both expression products are involved in the stability of an antibody producing cell. The stability of an antibody producing cell is defined as the capability of said antibody producing cell to remain in a certain developmental stage (optionally after said cell has been brought into said stage). Different developmental stages of a cell involve at least one different characteristic of said cell. For instance, a memory B cell is known to differentiate upon stimulation into an antibody-secreting plasma cell via a stage which some researchers call a plasmablast. A memory B cell, a plasmablast and a plasma cell are different developmental stages of a B cell, wherein the B cell has different characteristics. A memory B cell exhibits low proliferation and antibody secretion. A plasmablast exhibits both higher proliferation and higher antibody secretion levels as compared to a memory B cell, whereas a plasma cell secretes high antibody levels but is not capable of proliferating. These three developmental stages are also characterised by differences in cell surface markers, as shown in Table 1.

With a method of the invention it has become possible to regulate the replicative life span of an antibody producing cell. A replicative life span of an antibody producing cell is defined herein as the time span wherein a B cell and its progeny cells are capable of replicating while maintaining their capability of producing antibody and/or developing into a cell that produces antibody. The replicative life span of an antibody producing cell is for instance shortened by forcing an antibody-producing cell to enter another developmental stage. In one embodiment the replicative life span of an antibody producing cell is shortened by forcing said cell into terminal differentiation. This is characterised by increased antibody production and cell cycle arrest. During terminal differentiation cells stop proliferating and eventually die. Preferably however the replicative life span of an antibody producing cell is prolonged, meaning that said antibody producing cell will not terminally differentiate—or only after a longer period as compared to the same kind of antibody producing cells that are currently used—and continue to proliferate in vitro. According to the invention it is possible to regulate the amount of BCL6 and/or Blimp-1 expression product in an antibody producing cell to such extent that the antibody producing cell is brought into, and/or kept in, a predetermined developmental state in which the cells continue to proliferate. With a method of the invention it has therefore become possible to increase the replicative life span of an antibody producing cell since it is possible to maintain a B cell in a certain developmental stage wherein replication occurs. In current ex vivo B cell cultures the replicative life span is only a few weeks to two months. After this time the cultured cell lose their capability of replicating, their capability of producing antibody and/or their capability of developing into a cell that produces antibody. With a method according to the current invention however it has become possible to prolong the replicative life span of antibody producing cells, so that ex vivo cultures are generated comprising cells that are capable of replicating and producing antibody (or developing into cells that produce antibody).

An antibody producing cell is defined as a cell which cell is capable of producing and/or secreting antibody or a functional part, derivative and/or analogue thereof, and/or which cell is capable of developing into a cell which is capable of producing and/or secreting antibody or a functional part, derivative and/or analogue thereof. Preferably, said antibody producing cell comprises a B cell and/or a B cell-derived plasma cell. A B cell is called herein an antibody producing cell, even when the B cell is in a stage wherein antibody production is low or not present at all, such as a naive B cell or a memory B cell, being activated or not, because such cells are capable of developing into cells that produce antibody, such as a plasmablast and/or plasma cell. Said antibody producing cell preferably comprises a mammalian cell. Non-limiting examples include antibody producing cells derived from a human individual, rodent, rabbit, llama, pig, cow, goat, horse, ape, gorilla. Preferably, said antibody producing cell comprises a human cell, a murine cell, a rabbit cell and/or a llama cell.

A functional part of an antibody is defined as a part which has at least one same property as said antibody in kind, not necessarily in amount. Said functional part is preferably capable of binding a same antigen as said antibody, albeit not necessarily to the same extent. A functional part of an antibody preferably comprises a single domain antibody, a single chain antibody and/or a Fab fragment. A functional derivative or analogue of an antibody is defined as an antibody which has been altered such that at least one property—preferably an antigen-binding property—of the resulting compound is essentially the same in kind, not necessarily in amount.

BCL6 encodes a transcriptional repressor which is required for normal B cell and T cell development and maturation and which is required for the formation of germinal centers. (Ye, 1997). BCL6 is highly expressed in germinal center B cells whereas it is hardly expressed in plasma cells. BCL6 inhibits differentiation of activated B cells into plasma cells. The transcriptional repressor B lymphocyte induced maturation protein-1 (Blimp-1) is required for development of a B cell into a plasma cell. The human variant of Blimp-1 is named Prdm1. As used herein, any reference to Blimp-1 includes a reference to Prdm1. Blimp-1 drives plasma cell differentiation. BCL6 and Blimp-1 repress expression of the other; thus in a natural situation when one reaches an higher expression level than the other, the stage of differentiation is enforced. In the human body, differentiation of plasma cells from activated naive or memory B cells involves downregulation of BCL6 and upregulation of Blimp-1. In germinal center cells BCL6 expression is high and Blimp-1 expression is low. In resting memory cells expression of BCL6 and Blimp-1 are low. Signals that trigger differentiation cause an upregulation of Blimp-1, and this Blimp-1 counteracts the expression of BCL6. The stage where both BCL6 and Blimp-1 are expressed is short-lived and is called a plasmablast. With progressively increasing Blimp-1 levels, BCL6 expression is extinguished, resulting in a plasma cell.

One embodiment provides a method according to the invention wherein BCL6 and Blimp-1 are co-expressed in an antibody producing cell (meaning that both BCL6 and Blimp-1 are expressed in an antibody producing cell) resulting in an antibody producing cell that is capable of proliferating when an appropriate signal is provided. It has been found that co-expression of BCL6 and Blimp-1 results in an antibody producing cell which is capable of both proliferating and producing antibody. BCL6 and Blimp-1 are preferably co-expressed in a B cell, preferably a human B cell. Co-expression of BCL6 and Blimp-1 in a B cell results in stabilization of said B cell in a plasmablast-like stage. Plasmablasts, like plasma cells, are capable of secreting antibody. However, plasmablasts are still capable of proliferating, whereas plasma cells have lost their capability of proliferating. Plasma cells are therefore unsuitable for culturing antibody-producing cell lines. Although plasmablasts exert highly favourable proliferating and antibody-producing characteristics, they have not yet been used for long term antibody production since it has not been possible to stabilize plasmablasts until the present invention.

With a method of the invention it has amongst other things become possible to convert a naive B cell or a memory B cell into a plasmablast-like cell and to stabilize said cell, so that rapid differentiation into a plasma cell does not occur. This is contrary to natural development of plasma cells, wherein expression of Blimp-1 in a memory B cell results in rapid development into a plasma cell, thereby inhibiting BCL6 expression so that the resulting plasma cell hardly expresses BCL6. One embodiment of the present invention thus involves co-expression of both BCL6 and Blimp-1 in a B cell, resulting in a cell that is capable of both proliferating and producing antibody. Preferably a stable culture of B cells is generated. Stable long term ex vivo cultures of antibody producing cells have now become possible. These antibody-producing B cells that co-express BCL6 and Blimp-1 can further be stabilized through the addition of the anti-apoptotic gene Bcl-xL. With the introduction of Bcl-xL it is now possible to grow plasmablasts under conditions of low cell density. Hence, the invention also provides a method to culture plasmablasten under conditions of low cell density comprising providing an antibody producing cell with expression levels of BCL6, Blimp-1 and Bcl-xL with any of the herein described methods.

The amount of BCL6 expression product (preferably a BCL6 protein) in an antibody producing cell is regulated in a variety of ways. In one embodiment an antibody producing cell is provided with a compound capable of directly or indirectly influencing BCL6 expression. An antibody producing cell is preferably provided with a compound capable of enhancing BCL6 expression, in order to counteract downregulation of BCL6 during expression of Blimp-1. Such compound preferably comprises a Signal Transducer of Activation and Transcription 5 (STAT5) protein or a functional part, derivative and/or analogue thereof, and/or a nucleic acid sequence coding therefore. STAT5 is a signal transducer capable of enhancing BCL6 expression. There are two known forms of STAT5, STAT5a and STAT5b, which are encoded by two different, tandemly linked genes. Administration and/or activation of STAT5 results in enhanced BCL6 levels. Hence, downregulation of BCL6 by Blimp-1 is at least in part compensated by upregulation expression of BCL6 by STAT5 or a functional part, derivative and/or analogue thereof. Hence, STAT5 or a functional part, derivative and/or analogue thereof is capable of directly influencing BCL6 expression. It is also possible to indirectly influence BCL6 expression. This is for instance done by regulating the amount of a compound which in turn is capable of directly or indirectly activating STAT5 and/or regulating STAT5 expression. Hence, in one embodiment the expression and/or activity of endogenous and/or exogenous STAT5 is increased. It is for instance possible to indirectly enhance BCL6 expression by culturing an antibody producing cell in the presence of interleukin (IL) 2 and/or IL 4 which are capable of activating STAT5.

Preferably, an antibody producing cell is provided with a nucleic acid sequence encoding STAT5 or a functional part, derivative and/or analogue thereof, wherein said nucleic acid sequence is constitutively active, meaning that STAT5 is continuously expressed, independent of the presence of (endogenous) regulators. In case that endogenous STAT5 expression is low, or absent, an exogenous constitutively active nucleic acid sequence encoding STAT5 or a functional part, derivative and/or analogue thereof is preferably applied resulting in a concentration of STAT5 or a functional part, derivative and/or analogue thereof which is sufficient to enhance BCL6 expression. Most preferably, an antibody producing cell is provided with a nucleic acid sequence encoding a compound comprising STAT5 or a functional part, derivative and/or analogue thereof, preferably a fusion protein, whose activity is regulated by an exogenous inducer of repressor, so that the extent of activation of BCL6 expression is regulated at will. Another system that allows for induction of BCL-6 is provided by a Tet-on system in which addition of tetracycline and/or derivatives of tetracycline induce activity of a transactivator that induced BCL6 gene transcription followed by BCL protein synthesis. In one preferred embodiment, an antibody producing cell is provided with a nucleic acid sequence encoding an estrogen receptor (ER) and STAT5 as a fusion protein ER-STAT5. This fusion protein is inactive because it forms a complex with heat shock proteins in the cytosol. This way, STAT5 is unable to reach the nucleus and BCL6 expression is not enhanced. Upon administration of the exogenous inducer 4 hydroxy-tamoxifen (4HT), the fusion protein ER-STAT5 dissociates from the heat shock proteins, so that STAT5 is capable of entering the nucleus and activating BCL6 expression.

Additionally, or alternatively, BCL6 expression in an antibody producing cell is enhanced by culturing said antibody producing cell in the presence of a compound capable of directly or indirectly enhancing BCL6 expression.

One embodiment therefore provides a method according to the invention comprising: providing said antibody producing cell with a compound capable of directly or indirectly enhancing BCL6 expression; and/or culturing said antibody producing cell in the presence of a compound capable of directly or indirectly enhancing BCL6 expression. Said compound capable of directly or indirectly enhancing BCL6 expression preferably comprises STAT5 or a functional part, derivative and/or analogue thereof. Provided is therefore a method according to the invention comprising providing said antibody producing cell with STAT5 or a functional part, derivative and/or analogue thereof, or with a nucleic acid sequence encoding STAT5 or a functional part, derivative and/or analogue thereof. In one embodiment said antibody producing cell is cultured after introduction of a nucleic acid sequence encoding STAT5 or a functional part, derivative and/or analogue thereof into said cell. Said nucleic acid sequence is for instance introduced into said cell by transfection and/or virus-mediated gene transfer. Many alternative methods for introducing a nucleic acid sequence into a cell are available in the art which need no further explanation here.

With a compound capable of directly or indirectly enhancing BCL6 expression it is possible to enhance expression of endogenous BCL6. In one preferred embodiment however an antibody producing cell is provided with a nucleic acid sequence encoding BCL6 or a functional part, derivative and/or analogue thereof. This way, it is possible to regulate a BCL6 concentration in an antibody producing cell independently from expression of endogenous BCL6. Hence, even if expression of endogenous BCL6 is low or absent, for instance caused by Blimp-1, an exogenous nucleic acid sequence encoding BCL6 or a functional part, derivative and/or analogue thereof is still capable of producing a concentration of BCL6 which is sufficient for influencing the stability of an antibody producing cell. Also provided is therefore a method according to the invention comprising providing said antibody producing cell with a nucleic acid sequence encoding BCL6 or a functional part, derivative and/or analogue thereof. Preferably, said antibody producing cell is provided with a constitutively active nucleic acid sequence encoding BCL6 or a functional part, derivative and/or analogue thereof, so that BCL6 expression is maintained even when endogenous BCL6 expression of said cell is inhibited by an endogenous repressor such as Blimp-1. Most preferably, expression of said nucleic acid sequence encoding BCL6 or a functional part, derivative and/or analogue thereof is regulated by an exogenous inducer of repressor, so that the extent of BCL6 expression is regulated at will. For instance, an inducible promoter system is used such as a Tet-on or Tet-off system.

In another preferred embodiment, the invention provides a method wherein the amount of BCL6 is indirectly regulated by providing an antibody producing cell with a nucleic acid sequence encoding E47 or a functional part, derivative and/or analogue thereof. E47 encodes a transcription factor that belongs to a family of helix-loop-helix proteins, named E-proteins. There are four E-proteins, E12, E47, E2-2 and HEB, which are involved in lymphocyte development. E12 and E47 are encoded by one gene, named E2A, which is spliced differently. E-proteins can be inhibited by the E protein inhibitor Id2, and Id3, and by ABF-1 (Mathas S., 2006). E proteins have been described as tumor suppressors and overexpression has been shown to induce apoptosis. One of the specific targets of E47 are the Socs1 and Socs3 genes. Those Socs genes are known as negative regulators of STAT5b and thus indirectly of BCL6. In other words, expression of E47 within a B cell enhances Blimp-1 expression which results in B-cell differentiation towards an antibody producing phenotype (plasmacell).

The amount of Blimp-1 expression in an antibody producing cell is also regulated in a variety of ways. In one embodiment an antibody producing cell is provided with a compound capable of directly or indirectly influencing Blimp-1 expression. Additionally, or alternatively, an antibody producing cell is cultured in the presence of a compound capable of directly or indirectly influencing Blimp-1 expression. Further provided is therefore a method according to the invention comprising providing said antibody producing cell with a compound capable of directly or indirectly influencing Blimp-1 expression. Further provided is a method according to the invention comprising culturing said antibody producing cell in the presence of a compound capable of directly or indirectly influencing Blimp-1 expression. Preferably, a compound is used that is capable of enhancing Blimp-1 expression in order to counteract downregulation of Blimp-1 during expression of BCL6. Said compound most preferably comprises IL21.

In one preferred embodiment said compound capable of directly or indirectly influencing Blimp-1 expression comprises a Signal Transducer of Activation and Transcription 3 (STAT3) protein or a functional part, derivative and/or analogue thereof, and/or a nucleic acid sequence coding therefore. STAT3 is a signal transducer which is involved in B cell development and differentiation. STAT3 is capable of upregulating Blimp-1 expression. Further provided is therefore a method according to the invention wherein said compound capable of directly or indirectly influencing Blimp-1 expression comprises STAT3 or a functional part, derivative and/or analogue thereof, or a nucleic acid sequence encoding STAT3 or a functional part, derivative and/or analogue thereof. Most preferably, expression of said nucleic acid sequence encoding STAT3 or a functional part, derivative and/or analogue thereof is regulated by an exogenous inducer of repressor, so that the extent of STAT3 expression is regulated at will. For instance, an inducible promoter system is used such as for instance a Tet-on or Tet-off system. In one embodiment a fusion product comprising of STAT3, a derivative or analogue, and ER is introduced in said cell allowing regulation of STAT3 expression by hydroxytamoxifen.

Since STAT3 is capable of influencing Blimp-1 expression, it is also possible to indirectly regulate Blimp-1 expression by administering a compound capable of directly or indirectly regulating the activity and/or expression of STAT3. In one embodiment an antibody producing cell is provided with a compound that is capable of enhancing the activity of STAT3, so that Blimp-1 expression is indirectly enhanced as well. Further provided is therefore a method according to the invention, wherein an antibody producing cell is provided with a compound capable of directly or indirectly enhancing activity of STAT3.

Hence, in one embodiment an antibody producing cell is provided with a compound capable of directly or indirectly activating STAT3, in order to enhance Blimp-1 expression.

STAT3 is activated in a variety of ways. Preferably, STAT3 is activated by providing an antibody producing cell with a cytokine. Cytokines, being naturally involved in B cell differentiation, are very effective in regulating STAT proteins. Very effective activators of STAT3 are IL-21 and IL-6, but also IL-2, IL-7, IL-10, IL-15 and IL-27 are known to activate STAT3. Moreover, Toll-like receptors (TLRs) which are involved in innate immunity are also capable of activating STAT3. One embodiment therefore provides a method of the invention, wherein said compound capable of directly or indirectly influencing Blimp-1 expression comprises IL-21, IL-2, IL-6, IL-7, IL-10, IL-15 and/or IL-27. Most preferably IL-21 is used, since IL-21 is particularly suitable for influencing the stability of an antibody producing cell. IL-21 is capable of upregulating Blimp-1 expression even when Blimp-1 expression is counteracted by BCL6.

Additionally, or alternatively a mutated Janus kinase (JAK) is used in order to activate STAT3.

Naturally, a JAK is capable of phosphorylating STAT3 after it has itself been activated by at least one cytokine. A mutated Janus kinase capable of activating STAT3, independent of the presence of cytokines, is particularly suitable in a method according to the present invention.

As already explained before, a compound capable of enhancing Blimp-1 expression in one embodiment comprises a nucleic acid sequence encoding STAT3 or a functional part, derivative and/or analogue thereof. The presence of an exogenous nucleic acid sequence encoding STAT3 or a functional part, derivative and/or analogue thereof allows for a continuous presence of STAT3 or a functional part, derivative and/or analogue thereof even when expression of endogenous STAT3 is very low or absent.

It is also possible to decrease expression and/or activity of STAT5 in order to upregulate Blimp-1. If the amount and/or activity of STAT5 is decreased, activation of BCL6 expression is decreased as well resulting in a decreased amount of BCL6 expression product. Since BCL6 and Blimp-1 counteract each other's expression, a decreased amount of BCL6 expression product results in an increased amount of Blimp-1 expression product. Compounds capable of downregulating the activity of STAT5 are thus capable of indirectly upregulating Blimp-1. Such compounds for instance comprise members of the suppressor of cytokine signalling (SOCS) proteins. In one embodiment the amount of Blimp-1 expression product in an antibody producing cell is therefore upregulated by providing said cell with a SOCS protein, and/or by activating a SOCS protein within said cell.

In one preferred embodiment the expression and/or activity of STAT5 is decreased when said antibody-producing cell is provided with a nucleic acid sequence encoding E47 or a functional part, derivative and/or analogue thereof. Therefore expression of E47 within B cells expressing high levels of STAT5b intervenes with differentiation and proliferation, i.e. blocking of STAT5 via E47 and SOCS results in decreased BCL6 levels and subsequently in increased Blimp-1 levels. Upregulated levels of Blimp-1 result in a decreased proliferation and in a differentiation of the involved cell towards an antibody-producing cell. In other words, expression of E47 within a B cell enhances Blimp-1 expression which results in B-cell differentiation towards an antibody producing phenotype (plasma cell).

By at least a functional part of a STAT5 protein, a STAT3 protein and/or BCL6 is meant a proteinaceous molecule that has the same capability—in kind, not necessarily in amount—of influencing the stability of an antibody producing cell as compared to a STAT5 protein, a STAT3 protein and/or BCL6, respectively. A functional part of a STAT5 protein or a STAT3 protein is for instance devoid of amino acids that are not, or only very little, involved in said capability. A derivative of a STAT5 protein, a STAT3 protein and/or BCL6 is defined as a protein which has been altered such that the capability of said protein of influencing the stability of an antibody producing cell is essentially the same in kind, not necessarily in amount. A derivative is provided in many ways, for instance through conservative amino acid substitution wherein one amino acid is substituted by another amino acid with generally similar properties (size, hydrophobicity, etc), such that the overall functioning is likely not to be seriously affected. A derivative for instance comprises a fusion protein, such as a STAT5-ER fusion protein whose activity depends on the presence of 4 hydroxy-tamoxifen (4HT). An analogue of a STAT5 protein, a STAT3 protein and/or BCL6 is defined as a molecule having the same capability of influencing the stability of an antibody producing cell in kind, not necessarily in amount. Said analogue is not necessarily derived from said STAT5 protein, STAT3 protein and/or BCL6.

A preferred embodiment provides a method according to the invention wherein said antibody producing cell is provided with an additional immortalizing agent, preferably a transforming agent such as EBV. With an additional immortalizing agent, the stability, proliferation and/or antibody production of an antibody producing cell according to the invention is enhanced. A transforming agent is an agent capable of modifying at least part of a cell's genome. Said transforming agent preferably comprises nucleic acid capable of being incorporated into a cell's genome.

In a preferred embodiment an antibody producing cell, preferably a B cell, is provided with Epstein-Barr virus (EBV). Infection of an antibody producing cell of the invention with EBV results in increased stability, proliferation and/or antibody production of said cell. In one particularly preferred embodiment an antibody producing cell, preferably a B cell, is cultured in the presence of IL-21 and provided with EBV. This results in improved proliferation and/or antibody production, as compared to the same kind of antibody producing cells without IL-21 and/or EBV. Said antibody producing cell is preferably cultured in the presence of IL-21 before being infected with EBV. Provided is therefore a method for increasing the stability of an antibody producing cell, comprising culturing said cell in the presence of IL-21 and providing said cell with EBV.

According to the present invention, IL-21 is particularly suitable for improving the stability of an antibody cell. Preferred embodiments comprise culturing antibody producing cells, preferably B cells, in the presence of IL-21, which antibody producing cells are furthermore provided with a compound capable of directly or indirectly enhancing BCL6 expression, with a nucleic acid sequence encoding BCL6 or a functional part, derivative and/or analogue thereof, and/or with a nucleic acid sequence encoding STAT5 or a functional part, derivative and/or analogue thereof. Said antibody producing cell is preferably infected with EBV. For instance, an antibody producing cell that is naturally infected with EBV is used in a method according to the invention. Alternatively, or additionally, an antibody producing cell is provided with EBV.

In one preferred embodiment said antibody producing cell is cultured in the presence of IL-21 before said antibody producing cell is provided with a compound capable of directly or indirectly enhancing BCL6 expression, with a nucleic acid sequence encoding BCL6 or a functional part, derivative and/or analogue thereof, and/or with a nucleic acid sequence encoding STAT5 or a functional part, derivative and/or analogue thereof. Culturing antibody producing cells, preferably B cells, in the presence of IL-21 before the amount of BCL6 and/or Blimp-1 expression product within said cell is influenced is preferred, because in these embodiments stability, proliferation and/or antibody production is particularly well improved.

In a preferred embodiment, the invention further provides a method for influencing the stability of an antibody producing cell as described herein further comprising directly or indirectly increasing the amount of Bcl-xL expression product within said antibody producing cell. This is for example accomplished by providing said antibody producing cell with a nucleic acid sequence encoding Bcl-xL or a functional part, derivative and/or analogue thereof or by nucleic acid sequences encoding other anti-apoptotic genes including but not limited to Bcl-2. In yet another embodiment this is accomplished by providing said antibody producing cell with a compound capable of directly or indirectly enhancing Bcl-xL expression, preferably said compound comprises APRIL, BAFF, CD40, BCR stimulation, cytokines, growth factors or downstream effectors like JNK and AKT (PKB).

Bcl-xL is a member of the anti-apoptotic Bcl-2 family, Bcl2-proteins interact with and counteract so-called Bcl-2 homology domain 3 (BH3)-only family members such as Bax, Bak, Bim, and Bad, which induce cytochome c release following intrinsic death stimuli (Boise, L. H., 1993). Thus, protection of mitochondrial membrane integrity through proteins like Bcl-xL is critical for cell survival.

STAT5 activation has been shown to protect cells from cell death. STAT5 has been shown to regulate the expression of Bcl-xL, supporting an anti-apoptotic role for STAT5.

STAT5 positively regulates the Bcl-xL expression through STAT binding elements within the Bcl-xL promoter. In vivo, Bcl-xL expression is absent in bone marrow of STAT5A/B-doubly deficient mice. Furthermore, STAT5-mediated erythroblast survival is dependent upon upregulation of Bcl-xL. Recently, it has been shown that transgenic overexpression of Bcl-xL in mouse B cells promotes B cell survival and nonmalignant plasma cell foci.

A method according to the invention is particularly suitable for producing an antibody producing cell culture comprising antibody producing cells that are capable of proliferating and secreting antibody. In one embodiment, a memory B cell is used in order to produce an ex vivo B cell culture. Alternatively, or additionally, a naive B cell is used. Said memory B cell and/or naive B cell is preferably human so that human antibodies are produced. Preferably a memory B cell is used with a desired specificity. This means that a memory B cell is used which is capable of developing into an antibody secreting cell, which antibodies have a desired specificity against an antigen of interest. Said antigen of interest for instance comprises a pathogen-derived antigen, a tumor-derived antigen and/or an autoantigen. In one embodiment B cells are isolated from a peripheral blood sample, a cord blood sample and/or a tonsil sample, using methods known in the art. Memory B cells are for instance isolated by selection for the B cell marker CD19 and (subsequent) selection for cell surface IgG and/or CD27. In a germinal center B cell, BCL6 expression is high whereas Blimp-1 expression is low. Natural development into an antibody secreting cell involves upregulation of Blimp-1 expression. Since Blimp-1 represses BCL6 expression, upregulation of Blimp-1 results in downregulation of BCL6 in a natural situation. In a preferred embodiment of the present invention however, Blimp-1 expression is upregulated while BCL6 expression is at least in part maintained. This results in an antibody producing cell wherein BCL6 and Blimp-1 are co-expressed. Said antibody producing cell is capable of proliferating and secreting antibody and is therefore suitable for use in an ex vivo B cell culture. In a more preferred embodiment, said antibody producing cell is protected by apoptosis by Bcl-xL. Said antibody producing cell is preferably infected with EBV. In one embodiment, an antibody producing cell that is naturally infected with EBV is used. Alternatively, or additionally, an antibody producing cell is provided with EBV. An antibody producing cell according to the present invention provides the advantage that it is stable and does not undergo terminal differentiation during a prolonged period. Said antibody producing cell according to the invention is stable for at least one week, preferably for at least one month, more preferably for at least three months, most preferably for at least six months. A B cell according to the invention is preferably cultured in the presence of CD40L since replication of most B cells is favoured by CD40L.

In one embodiment BCL6 expression is maintained at essentially the same level, or at a higher level, as compared to a germinal center B cell since a significant BCL6 expression, together with Blimp-1 expression, results in an antibody producing cell with preferred proliferation and antibody production properties and/or stability. In a preferred embodiment, said BCL6 expression and/or Blimp-1 expression are accompanied by Bcl-xL expression, resulting in even more preferred proliferation and antibody production properties and/or stability.

One embodiment therefore provides a method for producing an antibody producing cell which is stable for at least one week, preferably for at least one month, more preferably for at least three months, more preferably for at least six months, the method comprising: providing a memory B cell or a naive B cell; increasing an expression level of Blimp-1 in said cell; and increasing and/or maintaining a BCL6 expression level in said cell. An ex vivo method for producing an antibody producing cell comprising increasing an expression level of Blimp-1 in a memory B cell or a naive B cell and increasing and/or maintaining a BCL6 expression level in said cell is also provided. Said BCL6 and Blimp-1 expression levels are preferably brought to, and/or maintained at, essentially the same level, or at a higher level, as compared to a plasmablast. In one embodiment said B cell is infected with EBV (naturally and/or artificially) and/or transduced with Bcl-xL. Most preferably a memory B cell is used. Said memory B cell preferably has a specificity for a pathogen-derived antigen, a tumor-derived antigen and/or an autoantigen.

Blimp-1 expression and BCL6 expression are influenced in various ways, as already described herein before. For instance, Blimp-1 expression is enhanced in a memory B cell and/or a naive B cell by providing said B cell with a compound capable of directly or indirectly enhancing Blimp-1 expression, such as a nucleic acid sequence encoding Blimp-1 or a functional part, derivative and/or analogue thereof, and/or a nucleic acid sequence encoding STAT3 or a functional part, derivative and/or analogue thereof. Preferably, expression of said nucleic acid is regulated by an exogenous inducer of repressor, so that the extent of Blimp-1 expression is regulated at will.

Alternatively, or additionally, a memory B cell and/or a naive B cell is cultured in the presence of a compound capable of directly or indirectly enhancing Blimp-1 expression, such as for instance IL-21, IL-2, IL-6, 11-7, IL-10, IL-15, IL-27, or a mutated Janus kinase. Preferably, IL-21 is used because this cytokine is particularly suitable for enhancing Blimp-1 expression and stabilizing an antibody producing cell with a method according to the present invention. In one embodiment a B cell is provided with a SOCS protein or a functional part, derivative and/or analogue thereof, or a nucleic acid coding therefore, since a SOCS protein or a functional part, derivative and/or analogue thereof is capable of indirectly enhancing Blimp-1 expression. In another alternative or additional embodiment, a B-cell is provided with E47 or a functional part, derivative and/or analogue thereof, or a nucleic acid coding therefore. As already outlined earlier, as a result of an increased level of E47 or a functional part, derivative and/or analogue thereof, Socs protein function is enhanced and Blimp-1 expression is indirectly increased. Expression of Blimp-1 results in downregulation of endogenous BCL6. Therefore, said memory B cell is preferably also provided with a compound capable of maintaining BCL6 expression, resulting in co-expression of both BCL6 and Blimp-1. Said compound is preferably capable of inducing and/or maintaining BCL6 expression at essentially the same level or at a higher level as compared to a plasmablast. A preferred example of such compound is a nucleic acid sequence encoding BCL6 or a functional part, derivative and/or analogue thereof.

It is possible to directly provide a B cell with a compound capable of directly or indirectly enhancing BCL6 expression, for instance by transduction with a nucleic acid sequence. In one embodiment BCL6 expression in a B cell is maintained and/or enhanced by culturing a memory B cell in the presence of a compound which is capable of directly or indirectly enhancing BCL6 expression and/or which is capable of maintaining BCL6 expression at essentially the same level, or at a higher level, as compared to a germinal center B cell.

In a preferred embodiment Blimp-1 expression is upregulated in a B cell, preferably by culturing said B cell in the presence of a compound capable of activating STAT3 and/or Blimp-1. Said compound preferably comprises IL-21. Said B cell preferably comprises a memory B cell. After this, BCL6 expression is preferably enhanced. It has been demonstrated that Blimp-1 upregulation in a first stage followed by BCL6 upregulation results in particularly stable B cells capable of replicating and producing antibody. In one embodiment of the invention Blimp-1 expression is still upregulated while BCL6 expression is enhanced. Alternatively however, Blimp-1 expression is not upregulated while BCL6 expression is enhanced. This way, the replication capacity of a B cell is particularly enhanced. Hence, an antibody producing capacity of a B cell is preferably enhanced firstly, by upregulating expression and/or activity of Blimp-1. Subsequently, a replication capacity of said B cell is preferably enhanced, by upregulating expression and/or activity of BCL6. The B cell is preferably cultured in the absence of a compound capable of enhancing Blimp-1 expression and/or activity, until replication is significantly increased. Subsequently, said B cell is preferably cultured again in the presence of an enhancer of Blimp-1 expression and/or activity, so that antibody production is maintained. As is shown in the examples, it is possible to regulate Blimp-1 and BCL6 in various ways, resulting in co-expression of both Blimp-1 and BCL6 in a B cell which B cell is capable of replicating and producing antibody. In one preferred embodiment said B cell is infected with EBV (naturally and/or artificially) and/or transduced with Bcl-xL.

In one preferred embodiment Blimp-1 expression is upregulated in a B cell, preferably a memory B cell, by culturing said B cell in the presence of a compound capable of activating STAT3. Said compound preferably comprises IL-21. According to one embodiment, said B cell is subsequently provided with a nucleic acid sequence encoding BCL6 or a functional part, derivative and/or analogue thereof. Said B cells are preferably cultured for a few days in the absence of said compound capable of activating STAT3 in order to enhance replication. Subsequently, said cells are preferably again cultured with—and/or provided with—a compound capable of activating STAT3.

In the Examples a particularly preferred embodiment is shown, wherein B cells are firstly cultured in the presence of IL-21. Subsequently the B cells are provided with a nucleic acid sequence encoding BCL6. The B cells are cultured in the absence of IL-21 and in the presence of IL-2 and IL-4 for a few days in order to allow BCL6 expression, after which IL21 is administered again to the culture in order to enhance replication and antibody production. Stable B cells are obtained wherein BCL6 and Blimp-1 are co-expressed, which B cells are capable of replicating and producing antibody in an ex vivo culture during at least 6 months. In one preferred embodiment said B cells are infected with EBV. A B cell culture according to the invention is preferred since the B cells are capable of replicating and producing antibody in an ex vivo culture during a longer period of time as compared to current B cell cultures.

In another preferred embodiment a nucleic acid sequence encoding STAT5 or a functional part, derivative and/or analogue thereof is used in order to enhance BCL6 expression.

Prior art attempts to use STAT5 in order to obtain a stable B cell culture capable of producing antibodies, such as described in WO 03/052083, failed because the B cells lose their capability of developing into antibody producing cells within 2 months. The present invention however provides the insight that STAT5 is indeed suitable for producing a stable antibody producing B cell culture if Blimp-1 expression is upregulated in the B cells as well. Preferably, Blimp-1 expression in a B cell is enhanced, after which BCL6 expression is enhanced by STAT5 or a functional part, derivative and/or analogue thereof.

In a preferred embodiment Blimp-1 expression is upregulated in a B cell, preferably by culturing said B cell in the presence of a compound capable of activating STAT5. Said compound preferably comprises IL-21. Said. B cell preferably comprises a memory B cell. Subsequently, said B cell is provided with a nucleic acid sequence encoding STAT5 or a functional part, derivative and/or analogue thereof. Said nucleic acid sequence preferably encodes a compound comprising STAT5 or a functional part, derivative and/or analogue thereof, whose activity depends on the presence or absence of an exogenous regulator. Most preferably said B cell is provided with a nucleic acid sequence encoding a STAT5-ER fusion protein whose activity depends on the presence of 4 hydroxy-tamoxifen (4HT). In the resulting B cells, which are capable of both replicating and producing antibody, Blimp-1 and BCL6 are co-expressed. Once a culture comprising B cells according to the invention has been produced, it is possible to further regulate the replication and antibody production capacity of the B cells by regulating BCL6 and Blimp-1 expression. The amount of BCL6 and Blimp-1 expression product is regulated at will during further culturing. For instance, when antibody production of the cells diminishes, the activity of STAT5 is preferably diminished (preferably by depriving the cell culture of 4 hydroxy-tamoxifen) while said B cells are cultured in the presence of a compound capable of activating (expression of) STAT3 and/or Blimp-1. Preferably, the cells are cultured for a while (typically about a few days) in the presence of IL-21 and in the absence of 4 hydroxy-tamoxifen. When antibody production has been enhanced, culturing is preferably continued in the presence of hydroxy-tamoxifen and in the absence of said compound capable of activating STAT3 in order to enhance replication and to make sure that Blimp-1 expression does not completely abolish BCL6 expression.

In one embodiment, replication and antibody production are enhanced by EBV infection. Hence, after said B cell has been provided with STAT5, it is preferably infected by EBV. Stable B cells are obtained which secrete high antibody levels.

In the Examples a particularly preferred embodiment is shown wherein B cells are firstly cultured in the presence of IL-21 during a few days. Blimp-1 expression is induced and the B cells differentiate into antibody producing cells. Subsequently the B cells are provided with a nucleic acid sequence encoding STAT5-ER. The B cells are cultured in the presence of IL-21 for about 1-50 days, preferably about 1-30 days, more preferably about 1.5-21 days, most preferably about 1-5 days, where after the B cells are cultured in the absence of IL-21 and in the presence of 4-HT, IL-2 and IL-4 in order to activate STAT5. During this period, BCL6 expression is enhanced in order to maintain an equilibrium wherein BCL6 and Blimp-1 are co-expressed. Finally, after immortalization and expansion, IL-21 is administered again to the culture and 4HT is withdrawn in order to increase Blimp-1 expression. Said equilibrium wherein BCL6 and Blimp-1 are co-expressed is maintained by varying the amount of IL-21 and 4-HT in the culture medium so that both BCL6 expression and Blimp-1 expression are maintained. Stable B cells are obtained which are capable of replicating and producing antibody in an ex vivo culture during at least 6 months.

Hence, a method of the invention allows for subtle regulation of the replication capacity and antibody producing capacity of B cells cultured ex vivo. When upregulation of antibody production is desired, Blimp-1 expression is favored over BCL6 expression. When upregulation of replication is desired, BCL6 expression is favored over Blimp-1 expression. A method of the invention allows maintenance of an equilibrium wherein BCL6 and Blimp-1 are co-expressed, resulting in antibody producing cells which are capable of replicating and producing antibody ex vivo. In one embodiment said B cells are infected with EBV after said equilibrium has been established, in order to further increase and stabilize antibody production.

Moreover, the invention further discloses that regulation of the mentioned equilibrium is also obtained by an E protein (for example E47). Expression of E47 within B cells expressing high levels of STAT5b intervenes with differentiation and proliferation, i.e. blocking of STAT5 via E47 and SOCS results in decreased BCL6 levels and subsequently in increased Blimp-1 levels. Upregulated levels of Blimp-1 result in a decreased proliferation and in a differentiation of the involved cell towards an antibody-producing cell. In other words, expression of E47 within a B cell enhances Blimp-1 expression which results in B-cell differentiation towards an antibody producing phenotype (plasmacell).

The invention further describes the stabilization of the growth of antibody producing cells with Bcl-xL.

The invention therefore provides a method for producing an antibody producing cell which is stable for at least one week, preferably at least one month, more preferably at least three months, more preferably at least six months, the method comprising: providing a B cell with a compound capable of directly or indirectly enhancing Blimp-1 expression and/or culturing a B cell in the presence of a compound capable of directly or indirectly enhancing Blimp-1 expression; and providing said B cell with a compound capable of directly or indirectly enhancing BCL6 expression or with a compound capable of maintaining BCL6 expression at essentially at a higher level, as compared to a germinal center B cell.

Alternatively, or additionally, said B cell is cultured in the presence of a compound capable of directly or indirectly enhancing Blimp-1 expression, in the presence of a compound capable of directly or indirectly enhancing BCL6 expression, and/or in the presence of a compound capable of maintaining BCL6 expression at essentially the same level, or at a higher level, as compared to a natural memory B cell.

Said compound which is capable of directly or indirectly enhancing BCL6 expression and/or maintaining BCL6 expression at a higher level, as compared to a natural memory B cell, preferably comprises: a nucleic acid sequence encoding BCL6 or a functional part, derivative and/or analogue thereof, and/or a nucleic acid sequence encoding STAT5 or a functional part, derivative and/or analogue thereof, and/or a compound capable of directly or indirectly activating STAT5, and/or a compound capable of directly or indirectly enhancing expression of STAT5.

A B cell is preferably firstly provided with a compound capable of directly or indirectly enhancing Blimp-1 expression, and/or cultured in the presence of a compound capable of directly or indirectly enhancing Blimp-1 expression, before BCL6 expression and/or BCL6 activity of said B cell is increased.

As already explained herein before, said compound capable of directly or indirectly enhancing Blimp-1 expression preferably comprises IL-21, IL-2, IL-6, 11-7, IL-10, IL-15, IL-27, a SOCS protein, E-protein E47, E12, E2-2 or HEB, a mutated Janus kinase and/or a nucleic acid sequence encoding STAT3 or a functional part, derivative and/or analogue thereof. Most preferably, IL-21 is used. If use is made of a nucleic acid sequence encoding BCL6, STAT5 and/or STAT3 and/or Bcl-xL, or a functional part, derivative and/or analogue of BCL6, STAT5 and/or STAT3 and/or Bcl-xL, expression of said nucleic acid sequence is preferably regulated by an activator and/or repressor that is inducible by an exogenous compound. This way, expression of said nucleic acid sequence is regulated by determining the amount of exogenous compound that is administered.

In a further preferred embodiment, an antibody producing cell is provided with an immortalizing agent in order to increase the stability, proliferation an/or antibody production of said cell. As already explained before, said immortalizing agent preferably comprises a transforming agent. In a particularly preferred embodiment a B cell is infected with EBV. Said B cell is preferably cultured in the presence of IL-21. As shown in the Examples, B cells infected with EBV and cultured in the presence of IL-21 show strong proliferation and enhanced antibody production. Said B cells are preferably cultured in the presence of IL-21 before being infected with EBV. However, it is also possible to isolate EBV infected B cells, preferably B cells that are naturally infected with EBV, and to culture them in the presence of IL-21. Further provided is therefore a method for influencing the stability of a B cell, comprising culturing said B cell in the presence of IL-21 and infecting said B cell with EBV. A method for influencing the stability of an EBV-infected B cell, comprising culturing said EBV-infected B cell in the presence of IL-21 is also herewith provided. In one embodiment a B cell is cultured in the presence of IL-21, infected with EBV, and subsequently cultured in the absence of IL-21.

One embodiment comprises influencing the amount of BCL6 expression product and/or Blimp-1 expression product in addition to EBV infection. Preferably, an antibody producing cell, preferably a B cell, is infected with EBV while BCL6 and Blimp-1 are co-expressed in said antibody producing cell. In one preferred embodiment, a B cell is provided with BCL6, and/or a compound capable of directly or indirectly enhancing BCL6 expression, and with EBV. Said compound capable of directly or indirectly enhancing BCL6 expression preferably comprises STAT5. In another preferred embodiment, a B cell which is already (naturally) infected by EBV is provided with BCL6 and/or a compound capable of directly or indirectly enhancing BCL6 expression, preferably STAT5. Said B cells are preferably cultured in the presence of IL-21.

Further provided is therefore a method according to the invention, comprising providing a B cell; preferably culturing said B cell in the presence of IL-21; providing said B cell with BCL6 and/or STAT5, or a functional part, derivative and/or analogue thereof; providing said B cell with Epstein Barr Virus; and culturing said B cell ex vivo. A method comprising providing an EBV-infected B cell; preferably culturing said B cell in the presence of Il-21; providing said B cell with BCL6 and/or STAT5, or a functional part, derivative and/or analogue thereof; and culturing said B cell ex vivo is also herewith provided. B cells are produced which show strong proliferation and antibody production.

In one embodiment a plurality of B cells is tested for a specificity for a given antigen. This is done using any method known in the art, for instance an ELISA. Subsequently, at least one B cell with a specificity for a given antigen is selected. This is for instance performed by incubating B cells with a labelled antigen and isolating said B cells using methods known in the art. Selected B cells are preferably cultured in the presence of IL-21. According to this embodiment, selected cells are provided with exogenous BCL6 and/or STAT5, or a functional part, derivative and/or analogue thereof, in order to induce, maintain and/or improve the presence and/or amount of BCL6 expression product. At least one B cell comprising exogenous BCL6 and/or STAT5, or a functional part, derivative and/or analogue thereof, is subsequently selected. Said selected B cell is infected with Epstein Barr Virus. This embodiment is particularly suitable for selecting and culturing B cells with a given specificity which are derived from a B cell pool. For instance, human B cells are collected by selection for CD19, which is a B cell marker, and incubated with an antigen of interest. This way, human B cells with a desired specificity are selected and further cultured ex vivo. Said B cells are preferably cultured in the presence of Il-21 in at least one stage of the culturing period. In one preferred embodiment said B cell is cultured in the presence of IL-21 before BCL6 and/or STAT5, or a functional part, derivative and/or analogue thereof, is introduced into said B cell. In yet another preferred embodiment, said B cell is further provided with Bcl-xL or a functional part, derivative and/or analogue thereof.

Even though EBV promotes proliferation and antibody production, EBV infection of an antibody producing cell is not always preferred. For instance, if strict control of the properties and genetic characteristics of an antibody producing cell are desired, one may choose not to use EBV infection because EBV infection involves incorporation of unknown nucleic acid sequences into a cell's genome. Moreover a B cell infected by EBV loses its B cell receptor (BCR) surface expression. This may be undesired, for instance when B cells are intended to be isolated and/or screened for a desired specificity after a long period of culture. Such isolation and/or screening method usually involves binding of B cells with a desired specificity to an antigen of interest with their BCR. EBV infected B cells, with significantly reduced BCR expression, are therefore less suitable for such isolation/screening methods. Hence, in cases where the presence of a B cell receptor on B cells is desired, such as for instance in screening assays, the B cells are preferably not, or at a later stage, infected with EBV.

One embodiment provides a method according to the invention further comprising selecting and/or isolating an antibody or a functional part, derivative and/or analogue of interest. In one embodiment IgM producing cells and IgG producing cells are selected and/or isolated. Preferably an IgG producing cell is selected and/or isolated.

Antibody producing cells generated with a method according to the invention are suitable for producing antibodies against an antigen of interest. In one preferred embodiment however, the genes encoding the Ig heavy and/or light chains are isolated from said cell and expressed in a second cell, such as for instance cells of a Chinese hamster ovary (CHO) cell line. Said second cell, also called herein a producer cell, is preferably adapted to commercial antibody production. Proliferation of said producer cell results in a producer cell line capable of producing antibody. Preferably, said producer cell line is suitable for producing compounds for use in humans. Hence, said producer cell line is preferably free of pathogenic agents such as pathogenic micro-organisms.

A method according to the invention is preferably used for generating an antibody producing cell that is stable for at least one week, preferably at least one month, more preferably at least three months, more preferably at least six months so that commercial antibody production has become possible. One preferred embodiment provides a method according to the invention, wherein an antibody producing cell is produced that is capable of producing antibodies against an antigen of interest. Said antigen of interest preferably comprises a pathogen-derived antigen, a tumor-derived antigen and/or an autoantigen. Most preferably a stable cell line capable of producing monoclonal antibodies is produced. This is preferably performed by using memory B cells that have for instance been isolated from a sample by selection for CD19 (B cell marker) and cell surface IgG and/or CD27 (to mark memory cells). Furthermore, an antibody producing cell capable of specifically binding an antigen of interest is for instance selected in a binding assay using said antigen of interest. Subsequently, according to this preferred embodiment Blimp-1 and BCL6 are co-expressed in said antibody producing cell, resulting in a culture of cells capable of specifically binding said antigen of interest. Preferably said antibody producing cell is infected with EBV. In yet another preferred embodiment, said B cell is further provided with Bcl-xL or a functional part, derivative and/or analogue thereof.

If only one memory cell is used, a cell line according to the invention producing monoclonal antibodies is obtained. It is also possible to generate a monoclonal antibody producing cell line starting with various B cells capable of producing antibody against different antigens. After a stable B cell culture has been produced with a method according to the invention, a B cell capable of producing antibodies against a specific antigen of interest is isolated and at least a functional part of a gene encoding the Ig heavy chain and/or light chain from said B cell is expressed in a second cell line. Preferably at least a functional part of the gene encoding the Ig heavy chain and at least a functional part of the gene encoding the Ig light chain from said B cell are expressed in a second cell line.

In one embodiment an antibody producing cell, preferably but not necessarily a memory B cell, that has been obtained from an individual which had been previously exposed to an antigen of interest, is used in a method, according to the invention. This way, it has become possible to produce human antibodies of interest ex vivo.

The invention furthermore provides an antibody producing cell which is stable for at least one week, preferably for at least one month, more preferably for at least three months, more preferably for at least six months, meaning that an antibody producing cell according to the present invention is capable of both replicating and producing antibody, or capable of replicating and developing into a cell that produces antibody, during said time periods. Antibody producing cells according to the invention comprise, amongst other things, cells producing IgM and cells producing other immunoglobulin isotypes like IgG, IgA, IgE. An antibody producing cell according to the invention is particularly suitable for use in an antibody producing cell line. Antibody producing cells according to the invention are preferably cultured ex vivo and antibodies produced by said cells are preferably collected for further use. Alternatively, or additionally, the antibody encoding genes of said cells are isolated for further use. Antibodies or functional parts, derivatives and/or analogues thereof produced with a method according to the invention are useful for a wide variety of applications, such as for instance therapeutic, prophylactic and diagnostic applications, as well as research purposes and ex vivo experiments. For instance, a screening assay is performed wherein antibodies or functional parts, derivatives and/or analogues according to the invention are incubated with a sample in order to determine whether an antigen of interest is present.

An antibody producing cell according to the invention preferably comprises a mammalian cell, more preferably a human cell, a murine cell, a rabbit cell and/or a llama cell. In a particularly preferred embodiment said antibody producing cell comprises a human cell, producing human antibody, because human antibodies are particularly suitable for therapeutic and/or prophylactic applications in human individuals.

An antibody producing cell according to the invention preferably comprises an exogenous compound which is capable of directly or indirectly influencing BCL6 expression and/or an exogenous compound which is capable of directly or indirectly influencing Blimp-1 expression. An antibody producing cell according to the invention preferably comprises an exogenous compound which is capable of directly or indirectly enhancing BCL6 expression and an exogenous compound which is capable of directly or indirectly enhancing Blimp-1 expression, because co-expression of BCL6 and Blimp-1 results in a preferred antibody producing cell according to the invention which is capable of proliferating and producing antibody.

As explained herein before, BCL6 expression is enhanced in a variety of ways. BCL6 expression is preferably upregulated using a nucleic acid sequence encoding BCL6 and/or STAT5, or a functional part, derivative and/or analogue of BCL6 and/or STAT5. Further provided is therefore an antibody producing cell according to the invention, comprising an exogenous nucleic acid sequence encoding BCL6 or a functional part, derivative and/or analogue thereof, and/or an exogenous nucleic acid sequence encoding STAT5 or a functional part, derivative and/or analogue thereof.

Moreover, Blimp-1 expression is enhanced in a variety of ways. Preferably a nucleic acid sequence encoding STAT3 or a functional part, derivative and/or analogue thereof is used. The invention therefore further provides an antibody producing cell according to the invention comprising an exogenous nucleic acid sequence encoding STAT3 or a functional part, derivative and/or analogue thereof.

In one embodiment said nucleic acid sequence encoding BCL6, STAT5, STAT3 and/or Bcl-xL and/or a functional part, derivative and/or analogue of BCL6, STAT5 and/or STAT3 and/or Bcl-xL is constitutively active, so that BCL6, STAT5, STAT3 and/or a functional part, derivative and/or analogue thereof remains present in an antibody producing cell according to the invention even when endogenous BCL6, STAT5 and/or STAT3 and/or Bcl-xL genes are downregulated by endogenous compounds. Most preferably, expression of said nucleic acid sequence encoding BCL6, STAT5, STAT3 and/or Bcl-xL or a functional part, derivative and/or analogue of BCL6, STAT5 and/or STAT3 and/or Bcl-xL is regulated by an activator and/or repressor that is inducible by an exogenous compound, so that the amount of BCL6, STAT5, STAT3 and/or Bcl-xL or a functional part, derivative and/or analogue thereof is regulated at will by regulating the amount of exogenous compound that is administered. One embodiment therefore provides an antibody producing cell according to the invention, wherein expression of said nucleic acid sequence encoding BCL6, STAT5, STAT3 and/or Bcl-xL or a functional part, derivative and/or analogue of BCL6, STAT5 and/or STAT3 and/or Bcl-xL, is regulated by an activator and/or repressor that is inducible by an exogenous compound.

As explained before, in various embodiments antibody producing cells according to the present invention are infected with EBV. The invention therefore further provides an antibody producing cell comprising: 1) an immortalizing agent, preferably a transforming agent, more preferably Epstein Barr virus; and 2) a compound which is capable of directly or indirectly influencing the amount of BCL6 expression product in said cell and/or a compound which is capable of directly or indirectly influencing the amount of Blimp-1 expression product in said cell. In one embodiment an antibody producing cell is provided with BCL6 and/or STAT5 and subsequently infected with EBV. Further provided is therefore an antibody producing cell comprising Epstein Barr virus and exogenous BCL6, or a functional part, derivative and/or analogue thereof. An antibody producing cell comprising Epstein Barr virus and exogenous STAT5, or a functional part, derivative and/or analogue thereof is also provided. Said antibody producing cell preferably is a B cell. As demonstrated in the examples, B cells provided with BCL6/STAT5 and EBV show particularly strong proliferation and antibody production.

An antibody producing cell according to the present invention with an increased stability is particularly suitable for the production of an ex vivo cell line. The invention therefore further provides a method for producing an antibody producing cell line comprising: obtaining a stable antibody producing cell with a method according to the invention, and culturing said antibody producing cell ex vivo.

Preferably a B cell line is generated. Most preferably a stable cell line comprising B cells capable of producing antibodies specifically directed against an antigen of interest is generated. This is preferably done by obtaining a B cell which is capable of developing into a cell which produces antibodies against an antigen of interest, such as for instance a pathogen-derived antigen, a tumor-derived antigen and/or an autoantigen. The amount of BCL6 and/or Blimp-1 expression in said cell is subsequently regulated. In one embodiment said B cell is infected with EBV. Said B cell is preferably obtained from an individual who has been exposed to an antigen of interest. Said individual preferably comprises a mammal, more preferably a human individual, a rabbit, a rodent and/or a llama. In a particularly preferred embodiment said individual is a human individual.

The invention therefore provides a method according to the invention, comprising: obtaining a B cell from an individual, preferably a human individual, who has been exposed to an antigen of interest, producing an antibody producing cell that is stable for at least one week, preferably at least one month, more preferably at least three months, more preferably at least six months using said B cell obtained from said individual in a method according to the invention, and culturing said antibody producing cell ex vivo.

One important application is the production of antibodies that are capable of specifically binding an antigen of interest. One embodiment of the invention therefore provides a method for producing antibodies capable of specifically binding an antigen of interest, the method comprising: obtaining a B cell capable of differentiating into a B cell which B cell produces antibodies capable of specifically binding said antigen of interest, producing an antibody producing cell that is stable for at least one week, preferably at least one month, more preferably at least three months, more preferably at least six months using said B cell in a method according to the invention, and obtaining antibodies produced by said antibody producing cell.

Said antibody producing cell is preferably further cultured ex vivo in order to provide a stable cell line capable of producing antibodies which are specifically directed towards an antigen of interest. More preferably at least a functional part of a gene encoding the Ig heavy chain and/or light chain from said B cell is expressed in a second cell. Said second cell is preferably used in order to produce a commercially suitable cell line.

The invention is further explained in the following examples. These examples do not limit the scope of the invention, but merely serve to clarify the invention.

EXAMPLES

Example 1

Methods

Human memory B cells are purified from peripheral blood or tonsil by first by positive selection for B cells with CD19 MACS® beads (Miltenyi Biotech). Memory B cells are then selected by surface staining and cell sorting for IgG. IgG$^+$ B cells are then cultured with mouse fibroblast L cells expressing CD40L in the presence of mouse or human IL-21 for 36 to 48 hours. Cells are then transferred to Retronectin® (Takara, Shiga, Japan)-coated tissue culture plates where they are transduced with a retrovirus encoding human BCL6-IRES-GFP for 16 h at 37.degree. C. Transduced cells are then cultured on CD40L-L cells in the presence of human IL-2 and human IL-4. After approximately 3-4 weeks the GFP$^+$ cells (that is, BCL6$^+$ cells) reach 100% of the culture after which BCL6$^+$ cells are cultured with IL-2 and IL-4 or with human or mouse IL-21. Using flow cytometry we monitor the expression of GFP, CD19, CD38, CD20, MHC class II, CD27 (BD Biosciences), and other markers using labeled antibodies. We monitor growth by cell counting, and Ig production is monitored by enzyme ELISA detection of Ig in the culture supernatant (Dako, Glostrup, Denmark). Gene expression is monitored by reverse transcriptase polymerase chain reaction (RT-PCR, Invitrogen, Breda, Netherlands).

Results

Introduction of BCL6 into memory B cells results in a greatly extended lifespan over normal B cells in culture (months vs. .about. 3 weeks). These cells maintain CD19, surface Ig, MHC class II, and express intermediate levels of CD38 and CD20, suggesting a memory cell phenotype (not shown). Culture of these cells on CD40L-L cells in the presence of IL-21 results in a significant growth advantage (FIG. 1) and acquisition of a plasmablast-like cell surface phenotype (CD38$^{hi}$CD20$^+$, FIG. 2). Importantly, IL-21 cultured cells secrete 300% more IgG compared with cells cultured IL-2 and IL-4. Together these data show that IL-21 culture promotes plasmablast development in an immortalized B cell population, exhibiting enhanced growth and antibody production.

Example 2

A non-limiting model of one embodiment of the present invention is depicted in FIG. 4.

In the human body, differentiation of plasma cells from memory B cells involves downregulation of BCL6 and upregulation of Blimp-1. In memory cells BCL6 is high and Blimp-1 expression is low. Signals that trigger differentiation cause an upregulation of Blimp-1, and this Blimp-1 counteracts the expression of BCL6. This stage is short-lived and is called the plasmablast. With progressively increasing Blimp-1 levels, BCL6 expression is extinguished, resulting in a plasma cell.

In one embodiment of the invention BCL6 expression is "locked", for instance because of stable expression mediated by a retroviral expression cassette integrated into the DNA of the B cells. Then, with BCL6 levels maintained, we "switch on" Blimp-1 expression, for instance by use of a cytokine that activates STAT5, such as IL-21 (FIG. 3). This combination, through modulation of key transcription, results in stable growth of cells that secrete antibody and have phenotype characteristics of a plasmablast.

TABLE 1

Cell surface markers of memory B cells, plasmablasts and plasma cells

|  | Memory | Plasmablast | Plasma Cell |
|---|---|---|---|
| CD38 | + | ++ | ++ |
| CD20 | + | + | − |
| CD27 | + | + | − |
| CD19 | ++ | + | − |
| CD138 | − | − | + |
| proliferation | low | high | none |
| Ig secretion | low | intermediate | high |

TABLE 2

|  | Memory | Plasmablast | Plasma Cell |
|---|---|---|---|
| BCL6 | ++ | + | − |
| Blimp-1 | − | + | ++ |

Example 3

Materials and Methods

Maintenance and Isolation of Human B Cells

Using standard procedures, CD19 positive human B cells were isolated from bloodbank derived buffy coat (other sources can be fresh heparin. or ACD blood, or a lymphoid organ for example tonsil or spleen). In brief, total peripheral blood mononuclear cells (PBMC) were isolated using ficoll density separation (Amersham, Buckinghamshire, UK). CD19 labeled beads were used to positively selected B cells by MACS cell sorting technique (Miltenyi, Auburn, Calif., USA). Cells were subsequently stained with appropriate combinations of monoclonal antibodies (mAbs) to CD19, CD27, IgG, IgM, CD3 (Becton Dickinson (BD), Franklin Lakes, N.J., USA) and phycoerythrin (PE) labeled Tetanus Toxoid (provided by A. Radbruch, Berlin, Germany) or any other labeled antigen. Cells were then sorted using the FACSAria (BD). Sorted cells were washed and cultured (1.5 to 2.times.10.sup.5 cells/ml) on irradiated CD40L-expressing L-cells (5.times.10.sup.4 cells/ml; provided by DR. J. Banchereau, Schering Plough France, Dardilly France), in Iscove's Modified D Minimal Essential Medium (IMDM) containing 8% fetal calf serum (FCS) and Penicillin/Streptomycin. Unless mentioned otherwise, these CD40L-expressing L-cells are always present in the cultures.

Transduction and Regulation of Mouse Constitutive Active STAT5b in B Cells

Purified B cells were primed to become transduced with the caSTAT5b gene. Two priming protocols were used: (1) purified B cells were cultured for 3 days with interleukin (IL) 2 (20 U/ml, Chiron, Emeryville, Calif., USA) followed by a 24 hour culture with IL-2 and IL-4 (10 ng/ml, R&D, Minneapolis, Minn., USA) or (2) purified B cells were cultured for 36 hours with recombinant mouse IL-21 (50 ng/ml, R&D). Subsequently, cells were plated on recombinant human fibronectin fragments CH-296 (Hanenberg H., Nat., Med. 1996; RetroNectin, Takara, Japan) and human serum albumin treated plates (Corning Life Sciences, Corning, N.Y., USA) in the absence of L-cells, with the cytokines IL-2/4 or IL-21. At last, cells were transduced with the caSTAT5b gene (described by Ariyoshi K., JBC, 2000 and obtained from T. Kitamura, IMSUT, Tokyo, Japan) fused to the estrogen receptor (ER, provided by H. Kurata, DNAX Institute, Palo Alto, Calif., USA). The activity of the caSTAT5b-ER fusion product can be controlled by the hormone hydroxytamoxifen (4HT, Sigma-Aldrich, St. Louis, Mo., USA). The transduction was performed using a retrovirus as described previously (Heemskerk M. H., JEM, 1997; Heemskerk M. H., Cell Immunol. 1999; Scheeren F. A., Nat Immunol, 2005). Transduction efficiency was determined by antibody staining of a truncated, signaling incompetent mutant of Nerve Growth Factor Receptor (.DELTA.NGFR, provided by C. Bonini, St. Raphael Hospital, Milan, Italy). Thus, outgrowth of B cells that contain the caSTAT5b gene depends on the presence of 4HT and these cells can be detected by antibody staining for NGFR (Chromaprobe, Maryland Heights, Mo., USA).

Development of 100% caSTAT5b Positive B Cell Lines that Secrete Antibodies

We have developed a B cell line that produces monoclonal antibodies and is 100% caSTAT5b (=NGFR) positive. This was achieved by differentiating B cells from a memory into an antibody producing phenotype, and transducing with the caSTA5b-ER-IRES-NGFR construct. The action of caSTAT5b makes the differentiated B cells insensitive to cell death. Differentiation of B cells is induced in the first 2 to 3 weeks after isolation (FIG. 5), using a cytokine mixture (IL-2, 4, 21 or combinations of these cytokines and CD40L). The time point that caSTAT5b is activated by adding 4HT affects the overall phenotype of the cultures. This because caSTAT5b blocks the cell to change its phenotype e.g. blocks further differentiation. Thus, the longer 4HT is withheld the more B cells will differentiate into antibody producing cells or into a type of cell that preferentially grows out under these culture conditions (suggestions for cell types are: naive, follicular, memory, antibody producing, plasma blast, plasma cell, marginal zone, perisinusoidal or transitional B cells—many of those B cell subsets have only been determined in mice). When 4HT is present in the culture medium, caSTA5b-ER-IRES-NGFR positive B cells can survive for long periods (Table 2).

TABLE 2

Overview of caSTATS5b-ER-IRES-NGFR transduced human B cell cultures

| Donor | Isolation | | Transduction | | Culture Time |
|---|---|---|---|---|---|
| | Date | Subtype | Protocol | Time on IL-21 | |
| B12 | 28 Apr. 2005 | CD19+TT+ | IL-2 IL-4 | 4 wks | 18 Oct. 2005 |
| B15 | 17 May 2005 | CD19+TT+ | IL-21 | 36 h | 5 Dec. 2005 |
| B16 | 31 May. 2005 | CD19+TT+ | IL-21 | 20 d | 5 Dec. 2005 |
| B18 | 22 Jun. 2005 | CD19+CD27+ and TT+ | IL-2 IL-4 and IL-21 | time series (36 h to 20 d) | 5 Dec. 2005 |
| B19 | 22 Jun. 2005 | CD19+CD27+ and TT+ | IL-2 IL-4 and IL-21 | time series (36 h to 20 d) | 5 Dec. 2005 |
| B20 | 6 Jul. 2005 | CD19+TT+ | IL-21 | 36 h | 5 Dec. 2005 |
| B21 | 6 Jul. 2005 | CD19+TT+ | IL-21 | 36 h | 6 Sept. 2005 |
| B22/B23/B24 | 6 Sep. 2005 | CD19+CD27+ IgM− and TT+ | IL-21 | 5 d | 5 Dec. 2005 |
| B25/B26 | 20 Oct. 2005 | CD19+CD27+ IgM− | IL-21 | 7 d | 5 Dec. 2005 |
| B27/B28 | 10 Nov. 2005 | CD19+CD27+ | IL-21 | 7 d | 5 Dec. 2005 |
| B29/B30 | 22 Nov. 2005 | CD19+CD27+ | IL-21 | 42 h | 5 Dec. 2005 |

PBMC were obtained after Ficoll gradient isolation of bloodbank derived buffy coats and subsequently sorted by CD19 MACS and CD27 or by FACS Aria cell sorting. Purified B cells were then cultured in the presence of L-cells with indicated cytokines before being transduced with a retrovirus containing the caSTAT5b-ER-IRES-NGFR gene construct.

Development of Single-Cell Derived, Clonal B Cell Cultures

Outgrowth of caSTA5b-ER-IRES-NGFR positive B cells generally takes about 4 weeks, after which clonal cultures can be obtained by performing limiting dilution (LD) cultures or single cell sorting using flow cytometry (the FACSAria). These cultures consist of 2500 to 5000 L-cells, normal concentrations of IL-2 and IL-4 and either 1, 5 or 10 B cell/96-well when the LD is performed with 100% NGFR+ cells and 10, 100 and 1000 cell/96-well when NGFR+ cells are sorted into 96 well using the FACSAria.

Restimulation of Antibody Production of caSTAT5b-ER Positive B Cell Cultures

Poly-, oligo- or monoclonal caSTAT5b-ER-IRES-NGFR positive B cell cultures that were negative or low on antibody production were washed extensively before cultures were (1) deprived of 4HT, IL-2 and IL-4 before being cultured with IL-21, then after 4-10 days of supernatants were tested for IgM and IgG production or (2) deprived of 4HT for 10 days meanwhile cultured with IL-2 and IL-4, and then at day 10 IL-2 and IL-4 are replaced by IL-21. Then at different time points supernatants are tested for IgM and IgG production.

Results

B Cell Differentiation and Proliferation; the IL-2 and IL-4 vs. IL-21 Protocol

IL-21 treated B cell cultures showed enhanced proliferative responses within the first 2-3 weeks compared to IL-2 and IL-4 (FIG. 6a). However, unlike the IL-2 and IL-4 cultures, continuous IL-21 stimulation resulted in decreased proliferation and cell death, even in the presence of active STAT5b (FIG. 6b). Suggesting that IL-21 eventually had to be replaced by IL-2 and IL-4. To study this in more detail, time series experiment were performed with CD19+CD27+ memory B cells, in which IL-21 was replaced by IL-2 and IL-4 after 36 hours or 5, 10, 15 and 20 days. As shown in FIG. 7, most cultures could be maintained after IL-21 withdrawal, even cultures that received IL-21 for 20 days.

Antibody Production by IL-21 Boosted Total Human Memory B Cell Cultures

Interestingly, in contrast to the IL-2 and IL-4 cultures, the IL-21 boosted cultures were able to produce antibodies for a relatively long period (IgG and IgM as measured by ELISA, Dako, Glostrup, Denmark) (FIGS. 8a and 8b, respectively). Importantly, of the polyclonal memory B cell cultures of donors B18 and B19, single-cell clones were obtained by LD culture (table 3).

TABLE 3

Frequency of clones that were isolated from CD19+CD27+NGFR+ sorted B cells

| | B18 | | B19 | |
|---|---|---|---|---|
| donor | positive well | total # wells | positive well | total # well |
| 1000 c/w | 8 | 9 | 8 | 10 |
| 100 c/w | 21 | 48 | 19 | 48 |
| 10 c/w | 6 | 48 | 2 | 48 |
| 1 c/w | 1 | 96 | 6 | 96 |

The majority of the clonal cultures produced IgM while only some produced IgG (FIG. 9). In addition, two clonal cultures produced both IgM and IgG clone 7 and clone 8). Whether these clones are indeed clonal or that class switching occurred remains to be determined. In the later case one BCR VDJ region should be found in the IgG or IgM gene fragments in this culture.

Antibody Production of IL-21 Boosted Tetanus Toxoid Specific B Cell Cultures

Next, we tested whether we could isolate B cells producing Tetanus Toxoid (TT) specific antibodies. In brief, the following protocol was carried out:

Part 1
(1) CD27+TT+ B cells were sorted (recovery was donor dependent and ranged from 10000-1000 cells),
(2) cultured with IL-21 for 36 h,
(3) transduced with caSTA5b-ER-IRES-NGFR,
(4) and cultured for variable times with IL-21 (36 h to 3 wks) after which IL-21 was replaced by IL-2, IL-4 and 4HT Part 2
(5) when cultures were 100% NGFR+ they were cloned by limiting dilution (LD)

After 2 to 3 months of culture, 100% NGFR+, .alpha.-TT-specific polyclonal B cell cultures were obtained from at least 7 different donors (PART 1). All donors were tested positive in a .alpha.-TT-IgG specific antibody ELISA (r-biopharm, Darmstadt, Germany). As shown in FIG. 10a, .alpha.-TT IgG levels were relatively low. Since immortalization of memory B cells resulted in high numbers of IgM producing cultures (FIG. 9), that indicates that the majority of the TT cultures are IgM positive. As shown in FIG. 10b, five out of seven donors were producing IgM, suggesting that the anti-TT antibodies are from IgM origin and thus not detected by our .alpha.-TT IgG ELISA.

This let us to develop an .alpha.-TT IgM ELISA based on the r-biopharm TT IgG ELISA. The only difference is in the final step, now a .alpha.-human IgM-HRP antibody instead of a anti-human IgG-HRP is added.

Next, from the polyclonal TT cultures, .alpha.-TT-specific B cell clones were derived by LD cultures (PART 2). These LD cultures were started with 100% NGFR+ polyclonal .alpha.-TT-specific B cells from four donors (table 4). Clones from donor B16 mainly produced IgG, while B18 and B19 produced IgM and B15 produced both IgG and IgM (not shown). Subsequently, supernatants of these clones were tested in the IgG TT or IgM TT ELISA (FIG. 11). Besides donor 15 all donors showed TT binding, although only 5 clones produced relatively high anti-TT antibody titers.

TABLE 4

Limiting dilution culture of 100% NGFR+TT-specific B cells

| | | Number of positive clones from 96 well | | |
|---|---|---|---|---|
| donor | Total # | from 1 c/w | from 5 c/w | from 10 c/w |
| B15 | 12 | 2 | 10 | — |
| B16 | 14 | — | 7 | 7 |
| B18 | 10 | 10 | — | — |
| B19 | 11 | 1 | 3 | 7 |

Restimulation of Antibody Production of IL-21 Boosted Tetanus Toxoid Specific B Cell Cultures were able to generate IgM and IgG producing poly- and monoclonal B cell cultures using IL-21 as a stimulus. Nevertheless, antibody production was not stable. To our surprise, however, these IL-21 treated cultures could be restimulated to produce IgG and IgM antibodies (FIGS. 12a and 12b, respectively). This was achieved by 4HT withdrawal and simultaneously stimulation with IL-21. Using this protocol, total antibody production increased 2- to 1000-fold for IgM, and 2- to 25-fold for IgG. Several of the supernatants of restimulated monoclonal cultures were now tested positive in the IgG and IgM Tetanus ELISA. (FIG. 13).

Important to note is that caSTAT5b or caSTAT5b-ER B cell cultures that had not been treated with IL-21 prior to caSTAT5b transduction and subsequent expansion could not be restimulated to produce antibodies under any conditions (see patent application WO 03/052083; not shown here).

Example 4

Materials and Methods

The detailed methods regarding: Maintenance and isolation of human B cells; Transduction and regulation of mouse constitutive active STAT5b in B cells; Development of 100% caSTAT5b positive B cell lines that secrete antibodies; Development of single-cell derived, clonal B cell cultures; and Restimulation of antibody production of caSTA5b-ER positive B cell cultures are described in Example 3

Antibody Production in IL-21 Containing B Cell Cultures that are EBV Infected and Express BCL6-IRES-NGFR or caSTAT5-ER-IRES-NGFR Purified primary CD19+CD27+ B cells (B cells) were stimulated for 36 h with IL-21 and irradiated CD40L expressing L-cells (L-cells) before being transduced with BCL6-IRES-NGFR or caSTAT5b-ER-IRES-NGFR. After transduction, BCL6 transduced cells were cultured with IL-21, and caSTAT5b-ER transduced cells were cultured with IL-2 and IL-4. Transduced cells became NGFR positive within 2 to 3 days and were subsequently sorted on a FACSAria. NGFR sorted cells were then cultured at cell densities of 100 to 5000 cells/96 well (mini bulk cultures, MBC). The BCL6/IL-21 MBC proliferated strongly compared to caSTAT5b-ER cultures. These cultures were tested for antibody production, expanded to 24 well and frozen (viable cells, cell pellet and supernatant). The caSTAT5b-ER cultures were expanded and split in two parallel 96 wells. One well was cultured with IL-2, IL-4 and 4HT and the other well was cultured with IL-21 and without 4HT.

RT-PCR

To test if the strong proliferative response was related to the presence of EBV, an EBV RT-PCR was performed. Total RNA was isolated from thawed pellets using the RNeasy mini kit (Qiagen). RNA was reverse-transcribed in a volume of 20 .mu.l containing 5 first-strand buffer, 500 .mu.M dNTPs, 25 .mu.g/l oligo(dT) and 200 U superscript II RT (Life Technologies). A portion of the cDNA solution (1 .mu.l) was amplified by PCR in a 50 .mu.l solution containing 20 mM Tris-HCl, 50 mM KCl, 1.5 mM MgCl2, 5 mM dNTPs, 2.5 U Taq DNA polymerase (Life Technologies) and 30 pmol of each primer. PCR conditions were as follows: a 7-minute denaturing step at 94.degree. C. followed by 30 cycles of 30 s at 94.degree. C., 30 s at 62.degree. C. (HPRT1), 52.degree. C. (LMP-1) and 58.degree. C. (EBNA1/2) and 30 s at 72.degree. C., and a final 7-minute extension at 72.degree. C. The oligonucleotides used for RT-PCR were as follows: HPRT1 forward (5'-TATGGACAGGACTGAACGTCTTGC-3') and HPRT1 reverse (5'-GACACAAACATGATTCAAATCCCTGA-3'); LMP-1 forward: (5'-GCGACTCTGCTGGAAATGAT-3') and LMP-1 reverse (5'-GACATGGTAATGCCTAGAAG-3'); EBNA1/2 forward (5'-AGCAAGAAGAGGAGGTGG-TAAG-3') and EBNA1/2 reverse (5'-GGCTCAAAGTG-GTCTCTAATGC-3').

In addition to the RT-PCR we performed a PCR directly on cell pellet and supernatant DNA that was isolated using the QIAmp isolation kit (Qiagen).

EBV Vultures

To study the role of EBV in our system in more detail, we set up experiments to determine proliferation and antibody production in untransduced, BCL6-IRES-NGFR and caSTAT5b-ER-IRES-NGFR transduced cells that were obtained from cultures with or without natural occurring EBV.

First Experimental Setup

TABLE 5

| | Experimental setup BCL6 | | |
|---|---|---|---|
| 1 | BCL6 | IL-21 | |
| 2 | BCL6 | IL-21 | EBV |
| 3 | | IL-21 | EBV |

Table 5 in summary:
BCL6 MBC with IL-21 and L-cells (cultures Ce2-B9 and Ce2 G9)
BCL6 MBC with IL-21 and L-cells and EBV (cultures Be3-F3 and Be2 G9)
BBV MBC with IL-21 and L-cells (cultures B28 and B29)
Cultures with IL-2 and IL-4 were also included. At weekly intervals antibody levels and cell numbers were determined (Table 7), EBV status of the cultures is shown in FIG. 14.

Second Experimental Setup

TABLE 6

Experimental setup caSTAT5b-ER
Table 6, caSTAT5b-ER MBC were cultured on 4HT, L-cells, IL-2 and IL-4 in 96 well at 1000 c/w

| 1 | 4HT | IL-2 and IL-4 | |
| 2 | no 4HT | IL-21 | EBV |
| 3 | no 4HT | IL-21 | EBV |

When cell density was high enough parallel cultures were created. One part was maintained on 4HT, L-cells, IL-2 and IL-4 while the other part was switched to IL-21, L-cells but no 4HT. Antibody production was determined by ELISA (DAKO) EBV infection was determined by LMP1 PCR (FIG. 16)

Results

EBV Infection of BCL6 Cultures, Determined by PCR

It was found that IL-21 induced strong B cell proliferation and differentiation, which we tested in two donors in combination with the transduction of BCL6 (Table 5). Indeed we found strong B cell outgrowth in culture conditions in which we cultured B cells at 1000 and 100 c/w densities (Table 7). However in one donor almost all cultures were suspected to be EBV infected based on the phenotype by light microscopy, color of the culture supernatant and enormous cell expansion. Indeed this donor (B29) turned out to be EBV infected (FIG. 14). The massive outgrowth of EBV infected cells demonstrates that the combination of BCL6 and IL-21 gives a growth advantage for EBV infected cells especially since the frequency of EBV infected B cells in vivo is thought to be relatively low. In contrast to donor B29, donor B30 was EBV negative, except for a weak and relatively small LMP1 band in sample Ce2-F2 (FIG. 14).

Proliferation of BCL6 Cultures in the Presence or Absence of EBV, IL-2 IL-4 and IL-21

To study the role of EBV, BCL6, IL-2, IL-4 and IL-21 on cell growth, proliferation kinetics were compared (see table 5 experimental set up). Samples were selected based on LMP-1 EBV PCR reactions (FIG. 14). EBV status was confirmed by the ability of EBV infected cells to grow in the absence of L-cells. The BCL6 samples cultured with IL-2 and IL-4 displayed a low proliferative capacity and could not be maintained (Table 7). All samples cultured in medium containing IL-21 showed strong proliferation. IL-2 and IL-4 could only induce strong proliferation when cells were infected with EBV alone, not in combination with BCL6.

TABLE 7 proliferation of BCL6 B cells
Table 7, Proliferation of BCL6 transduced and non-transduced B cells with and without EBV or with and without IL-2 IL-4 or IL-21; all samples contained L cells

| Culture | cytokines added | | |
|---|---|---|---|
| condition | IL-21 | IL-2 | IL-4 |
| BCL6 | ++ | − | |
| BCL6/EBV | +++ | + | |
| EBV | +++ | +++ | |

Determine Antibody Production by BCL6 Cultures in the Absence or Presence of EBV, IL-2 IL-4 and IL-21

IgG antibody production was determined of the long term cultures as described in table 5. The indicated antibody production levels are the mean antibody production of six to ten different measurements in time of two donors (FIG. 15). It is clearly shown that the BCL6/EBV/IL-21 cultures produce significantly more IgG than the BCL6/IL-21 cultures. Hence, EBV significantly enhances antibody production of BCL6 transduced B cells.

Thus, the combination of IL-21 and EBV results in high levels of antibody production, in the absence as well as in the presence of BCL6.

Determine the B Cell Receptor (BCR) Expression Alter Long Term Culture of BCL6 Transduced and EBV Infected Cells It has been described that EBV infected cells lose their BCR expression. Therefore B cells in IL-21 containing cultures (described in table 5) were stained for NGFR, CD19, Kappa en Lambda.

The BCL6 transduced, EBV negative cells remained BCR expression positive as determined by Kappa and Lambda staining. Hence, such cells are particularly suitable for isolating and/or screening after a long period of culture for a desired specificity, for instance using labelled antigen, because such cells will bind said labelled antigen with their BCR. However, when EBV was present BCR expression was lost or diminished. Since the BCL6/IL-21 cultures produced relatively lower amounts of antibody, as compared to the EBV infected cells, but maintain BCR surface expression this demonstrates that these cells remain in a pre-plasmablast phenotype while the EBV infected cells, which produce high amounts of antibody, differentiate or have been differentiated towards a phenotype better described as plasmablast.

In conclusion, in cases where the presence of a B cell receptor on B cells is desired, such as for instance in screening assays, the B cells are preferably not, or at a later stage, infected with EBV.

EBV Infection of caSTAT5b-ER Cultures, Determined by PCR

Parallel to the BCL6 transductions, transductions using caSTAT5b-ER were performed. Strikingly, in contrast to the BCL6 cultures, which all became EBV infected, the caSTAT5b-ER cultures of the same donor (B29) seemed to keep the natural distribution (percentage) of EBV infected cells. Several cultures had clear signs of EBV infection and were checked by LMP1 PCR and indeed were found to be positive. One of the signs caSTAT5b-ER cultures were EBV positive was the ability of the MBC to survive when treated with IL-21 in the absence of 4HT. These 4HT deprived B cells lack the active form of caSTAT5b and normally die within 2 to 3 weeks.

Proliferation and Antibody Production by caSTAT5b-ER-Transduced B Cells Under Different Conditions To study the role of EBV in the caSTAT5b-ER system experiments were performed as described in table 6. In table 8 a schematic overview is presented of the response of caSTAT5b-ER transduced B cells. Active caSTAT5b-ER by the presence of 4HT blocks B cell differentiation irrespective which cytokines were present or even if B cells were EBV infected. Therefore, caSTAT5b-ER cultures that are EBV infected and maintained in IL-2 IL-4 or IL-21 but with 4HT do not produce antibody. Withdrawal of 4HT results in differentiation and subsequent antibody production. Preferably, IL-21 is added during and/or after withdrawal of 4HT. However, these cells ultimately die since caSTAT5b is inactive, and thus antibodies will only be produced for a restricted period. Hence, if no EBV is present, IL-21 is eventually replaced by at least one other growth stimulating agent, such as for instance Il-2 and IL-4, as already described in Example 3.

EBV and IL-21 together in the absence of 4HT are two strong stimuli which induce long term proliferation and high levels of antibody production (FIG. 18). This combination is therefore preferred.

TABLE 8 proliferation, survival and antibody production of caSTAT5b-ER B cells

| cytokines | EBV | 4HT | proliferation | survival | production |
|---|---|---|---|---|---|
| IL-2 IL-4 | − | + | + | pos | neg |
| IL-2 IL-4 | + | + | ++ | pos | neg |
| IL-21 | + | + | ++ | pos | neg |
| IL-21 | − | − | ++ | neg | intermediate |
| IL-21 | + | − | ++ | pos | high |

Example 5

Methods

BCL6-IRES-YFP positive cells were transduced with STAT3/ER-IRES-GFP using standard procedures and expanded on L cells with IL-2 and IL-4 as described in the Methods section of Example 1. The expression of STAT3 was regulated through the presence or absence of tamoxifen (4HT). YFP and GFP positive cell were sorted and equal numbers were cultured. BLIMP1 gene expression was monitored by RT-PCR and antibody production was determined in cultures with and without 4HT.

Results

Addition of 4HT to the cells resulted in increased cell numbers, increased Blimp-1 expression. Moreover, enhanced IgG production was measured as is shown in FIGS. 19a-c.

Example 6

CD19 positive B cells were transduced with control YFP-IRES-YFP (cYFP); BCL6-IRES-YFP (BCL6-YFP) or Bcl-xL-GFP (Bcl-xL-GFP). Cells were then maintained on CD40L and IL-4 and the percent YFP and GFP single and double positive cells was determined over time by FACS in unsorted bulk cultures.

Cell division and cumulative expansion was determined in single and double positive cell in the presence of IL-4 or IL-21.

To check for gene expression and EBV co-infection, RT-PCR analysis of Bcl-xL, BCL6, LMP1, and EBNA1 mRNA expression was performed in cultures of single BCL6-transduced and BCL6/Bcl-xL-double transduced bulk cultures.

Results

FIGS. 20-23 show that the double transduced B cells containing BCL6 and Bcl-xL had a higher cumulative expansion rate and indeed also were the dominant cells to grow out in bulk memory B cell cultures. We also show that these double transduced cells divided twice as fast compared to the single transduced cells. Not shown here are the antibody production levels (IgG and IgM), which were equal between the BCL6 and BCL6/Bcl-xL cultures when cultured with IL-4 or IL-21.

Example 7

The Hodgkin cell line L591, which is positive for tyrosine-phosphorylated STAT5, was cultured independent of L cells (CD40 stimulation) and cytokines. L591 cells were transduced by lentivirus containing E47-IRES-GFP or control virus with GFP only (methods are described in more detail in example 1). Transduced cells were sorted and cell growth was followed in time.

Results

FIG. 24 shows that L591 cells quickly stop dividing when E47 is expressed. This is suggestive for the effect of E47, which via its downstream targets (besides others Socs1, Socs3, Id2, Eto2 and Xbp1) induces B cell differentiation toward an antibody producing B cell phenotype. The induced differentiation by E47 could also indicate that the effects of STAT5 are abolished or that E47 directly or in directly affects the amount and action of functional STAT5. Thus based on the data with the Hodgkin cell line L591 we state that STAT5b/ER positive B cell cultures that are maintained on L cells with 4HT and IL-2 and IL-4 or IL-21, can be induced to differentiate towards antibody producing cells when the E47 is active.

Figure 1:
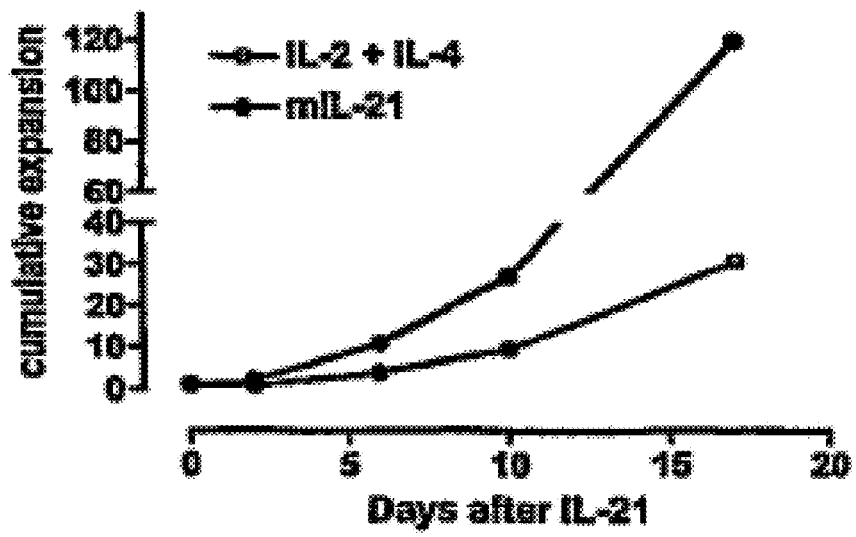
FIG. 1. Enhanced growth of BCL6+ cells cultured with IL-21. 100% pure BCL6+ memory B cells were cultured in the presence of IL-2 and IL-4 (conventional culture conditions), or with IL-21 alone. The total expansion of live cells over 17 days of culture with IL-21 is shown.
Figure 2:
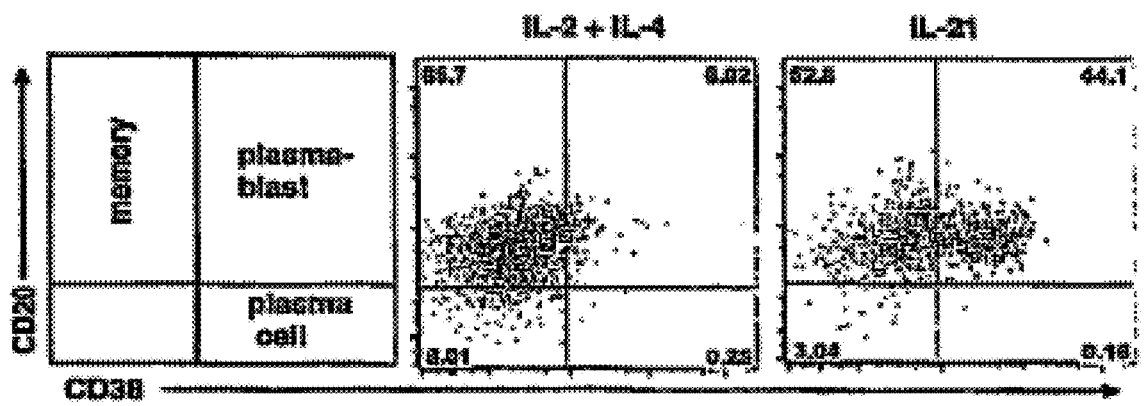
FIG. 2. Plasmablast immortalization of BCL6-positive cells with IL-21. Memory B cells were transduced With a retrovirus expressing BCL6-GFP and cultured with IL-2 and IL-4 (to prevent differentiation) or with IL-21 for 14 days. The surface staining for CD38 and CD20 of GFP+(that is, BCL6+) cells is shown. IL-21 induces an 8-fold increase in the amount of B cells with a plasmablast phenotype.
Figure 3:
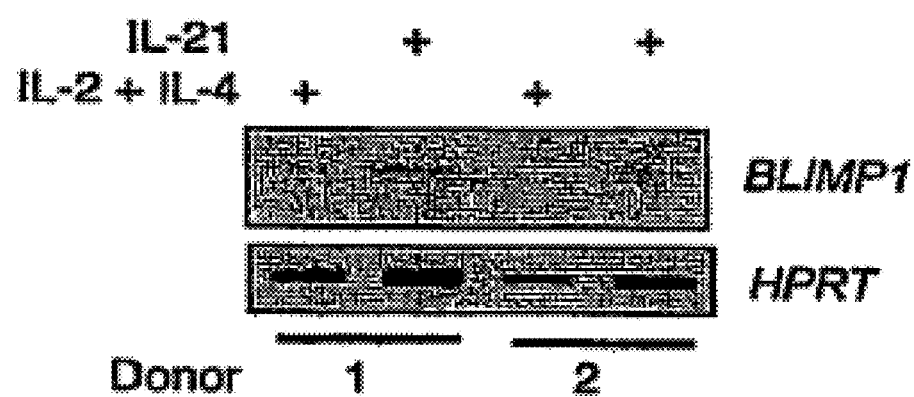
FIG. 3. IL-21 upregulates BLIMP1 in BCL6+ B cells. 100% pure BCL6-ΔNGFR+ were cultured with IL-2 and IL-4 or IL-21 for 24 days. cDNA was generated from total RNA and mRNA levels of BLIMP1 and HPRT (loading control) were determined by reverse transcriptase polymerase chain reaction.
Figure 4:
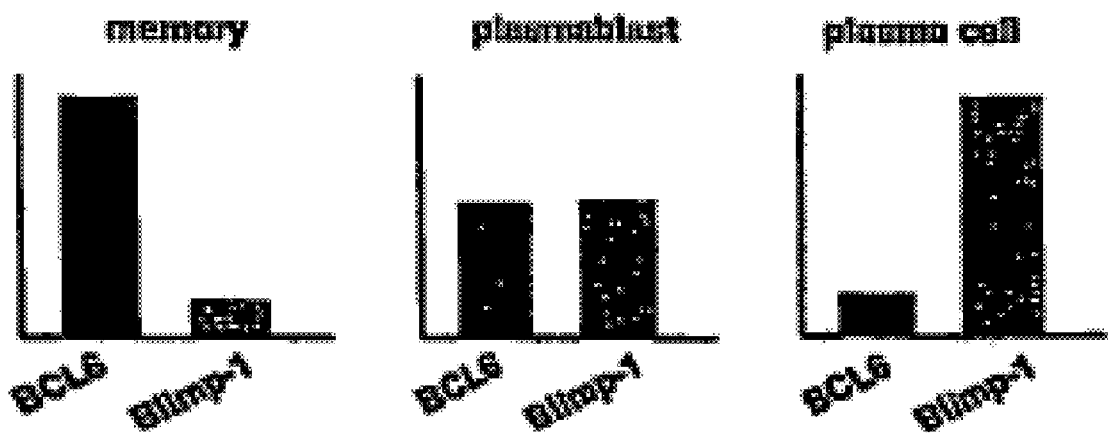
FIG. 4. Non-limiting model of one embodiment according to the present invention
Figure 4:
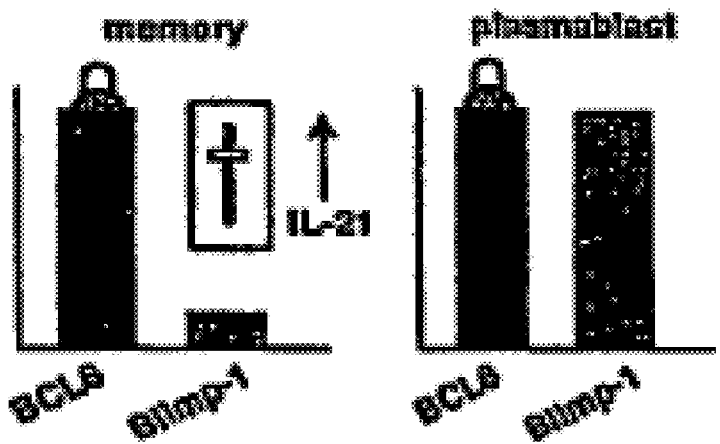
Figure 5:
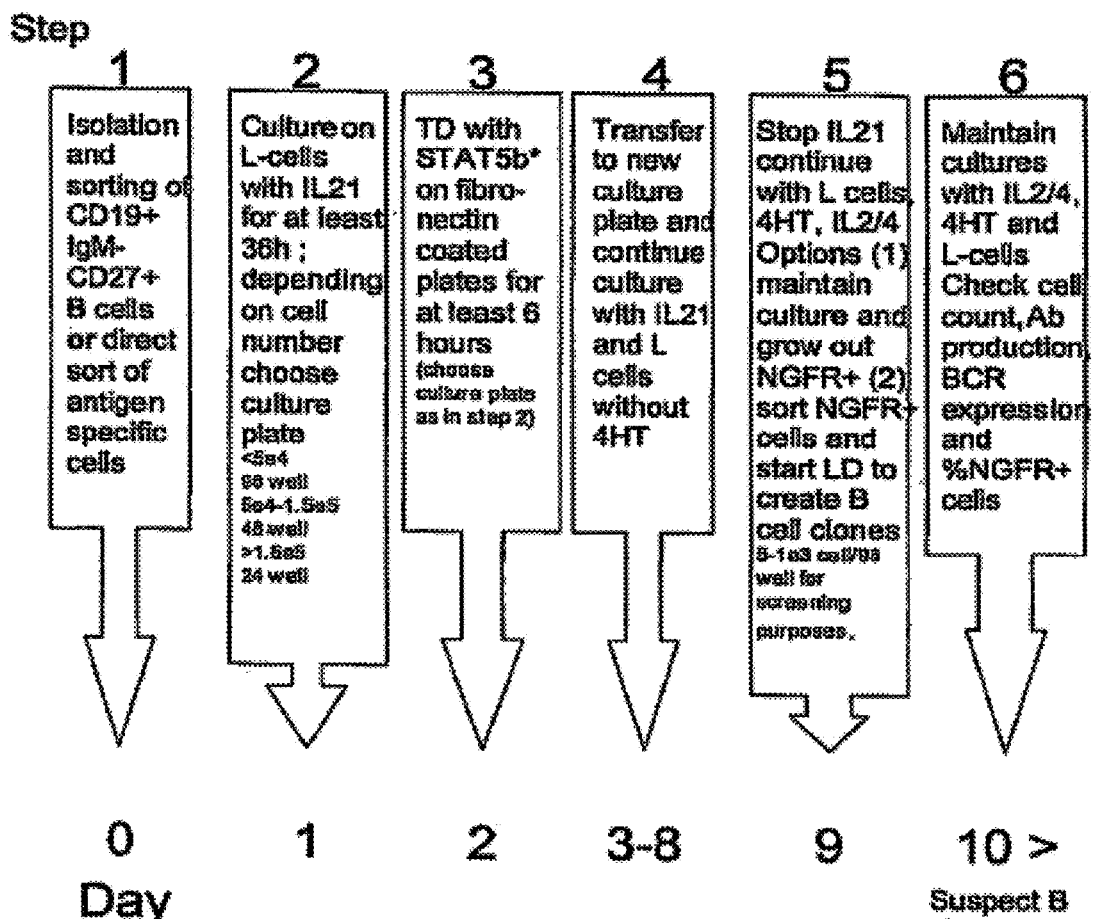
FIG. 5.
General overview of ideal culture scheme, see for more details the material and methods section of Example 3.
Figure 6A:
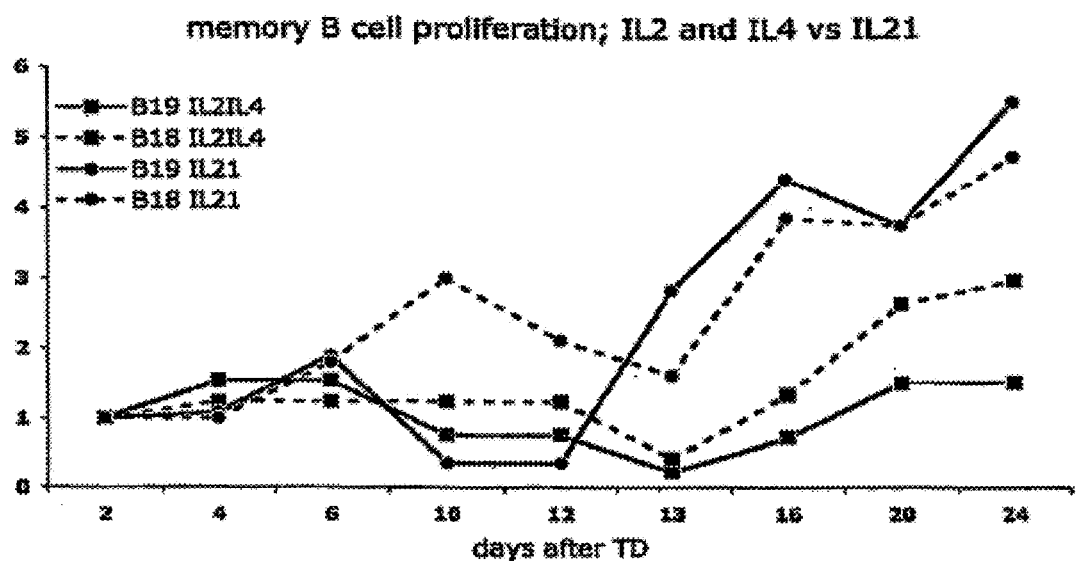
FIG. 6
Growth dynamics of IL-2 and IL-4 vs. IL-21 stimulated B cell. (a) Peripheral blood (PB) memory B cells derived from two donors (B18 and B19) were stimulated either with IL-21 or IL-2 and IL-4. Cells were transduced with caSTAT5b-ER-IRES-NGFR at day 2 for the IL-21 and at day 5 for IL-2 and IL-4 treated cultures; 4HT was added at day 13. (b) Of 4 donors Tetanus Toxoid specific B cells were sorted from PB (cell numbers ranged from 1000-10.000). Cells were cultured in 96 well with IL-21 and transduced with caSTAT5b-ER-IRES-NGFR on day 2. 4HT was added on day 4 and IL-21 was replaced with IL-2, IL-4 and 4HT after 7 days (B14 and B15) or was replaced after 20 days (B16 and B17). Cells were counted by hand and dead cells were excluded.
Figure 6B:
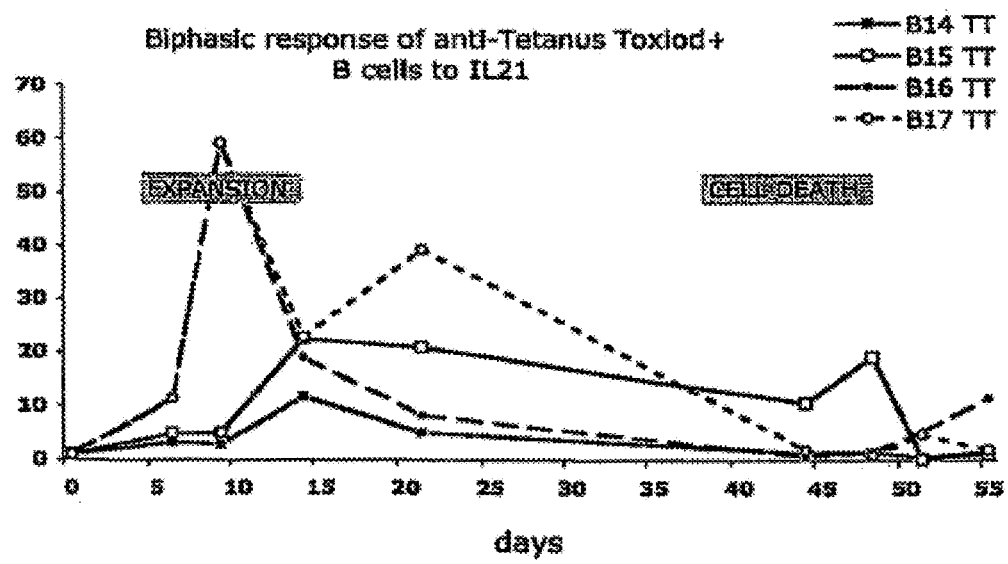
Figure 7:
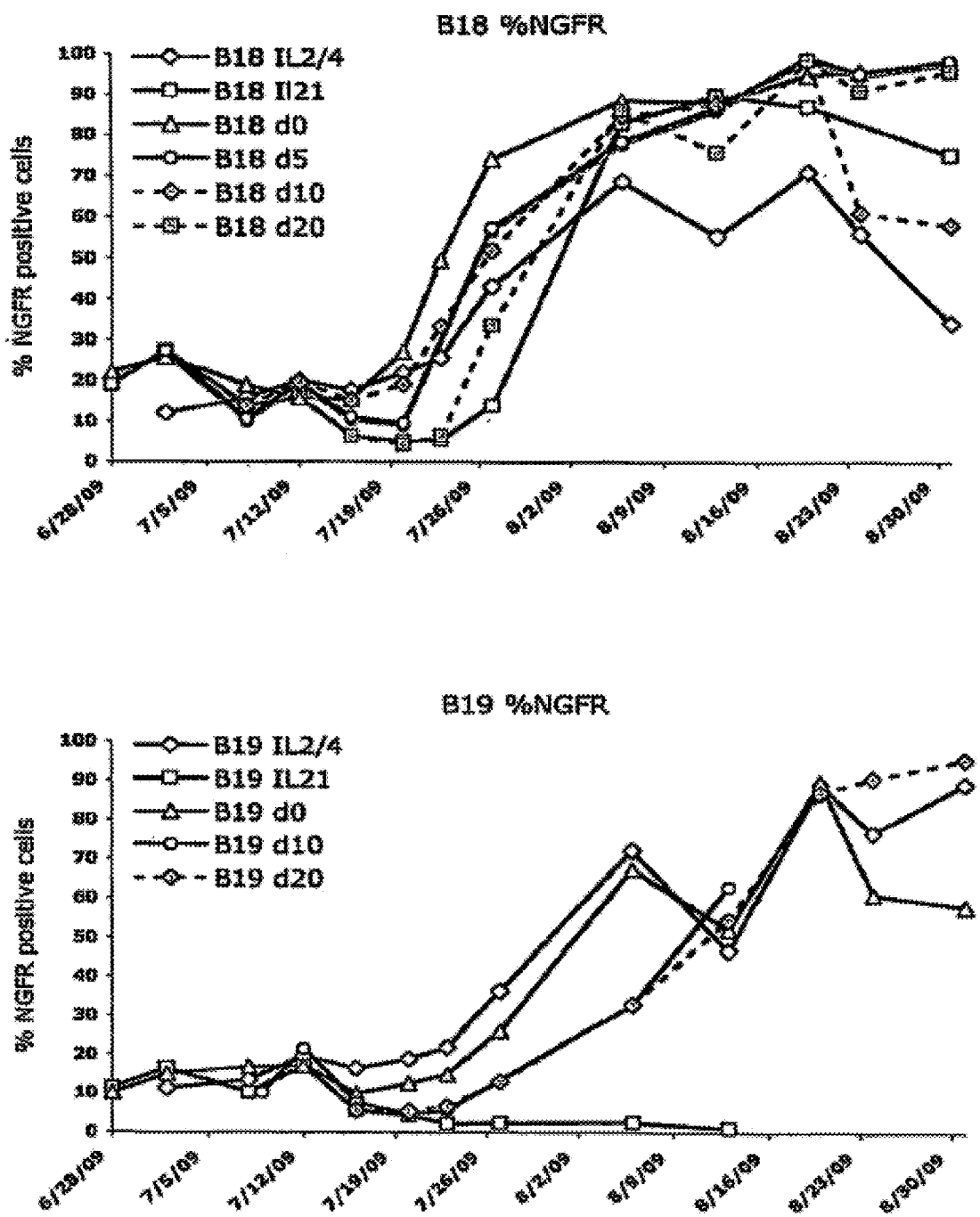
FIG. 7
Percentage caSTAT5b-ER-IRES-NGFR transduced cells was determined using the LSR II (BD). Of two donors (B18 and B19) IL-2 and IL-4 vs. IL-21 time series experiment were performed. Of each donor ¼ of the cells were transduced using the IL-2 and IL-4 protocol, the remaining ¾ was transduced using IL-21. Directly after the IL-21 transduction (36 h) one third of the IL-21 culture was switched to IL-2 and IL-4. This was repeated on day 5, 10 and 20 of the IL-21 culture.
Figure 8A:
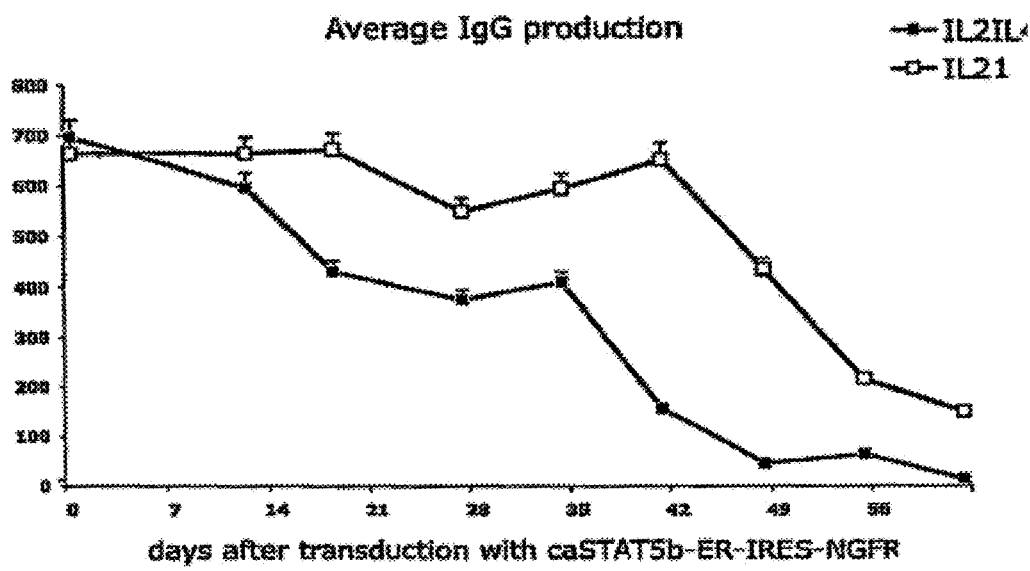
FIG. 8
Total human IgG and IgM antibody production by caSTAT5b-ER-IRES-NGFR transduced PB derived memory B cells, as described in FIGS. 6 and 7. (a) Mean IgG production of donor B18 and B19 is shown. B cells were transduced using the IL-2 and IL-4 vs. the IL-21 protocol. The IgG production indicated with the open symbols represent all cultures that had been treated with IL-21, irrespective when they were switched to IL-2 and IL-4. (b) IgM production in samples as described above, note that the time scale is different.
Figure 8B:
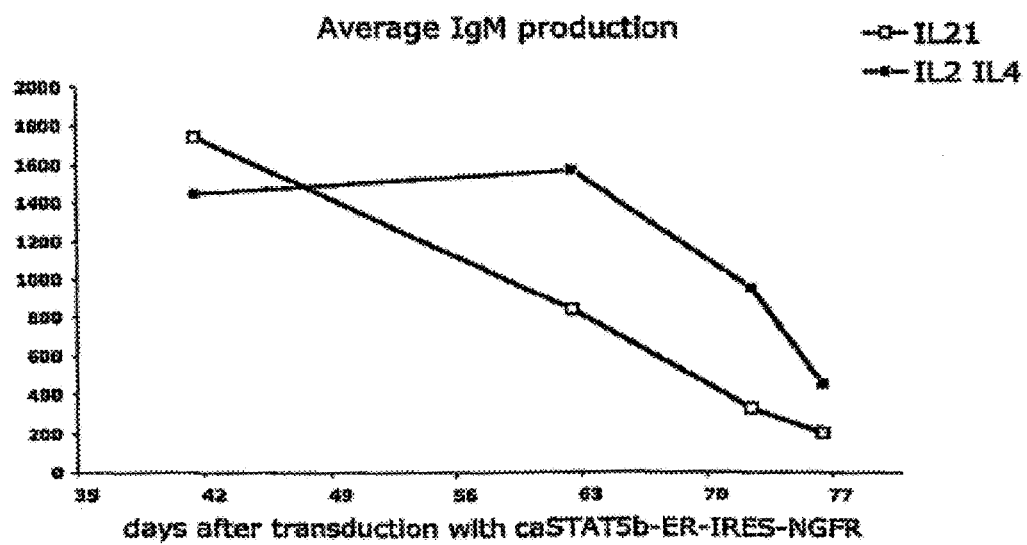
Figure 9:
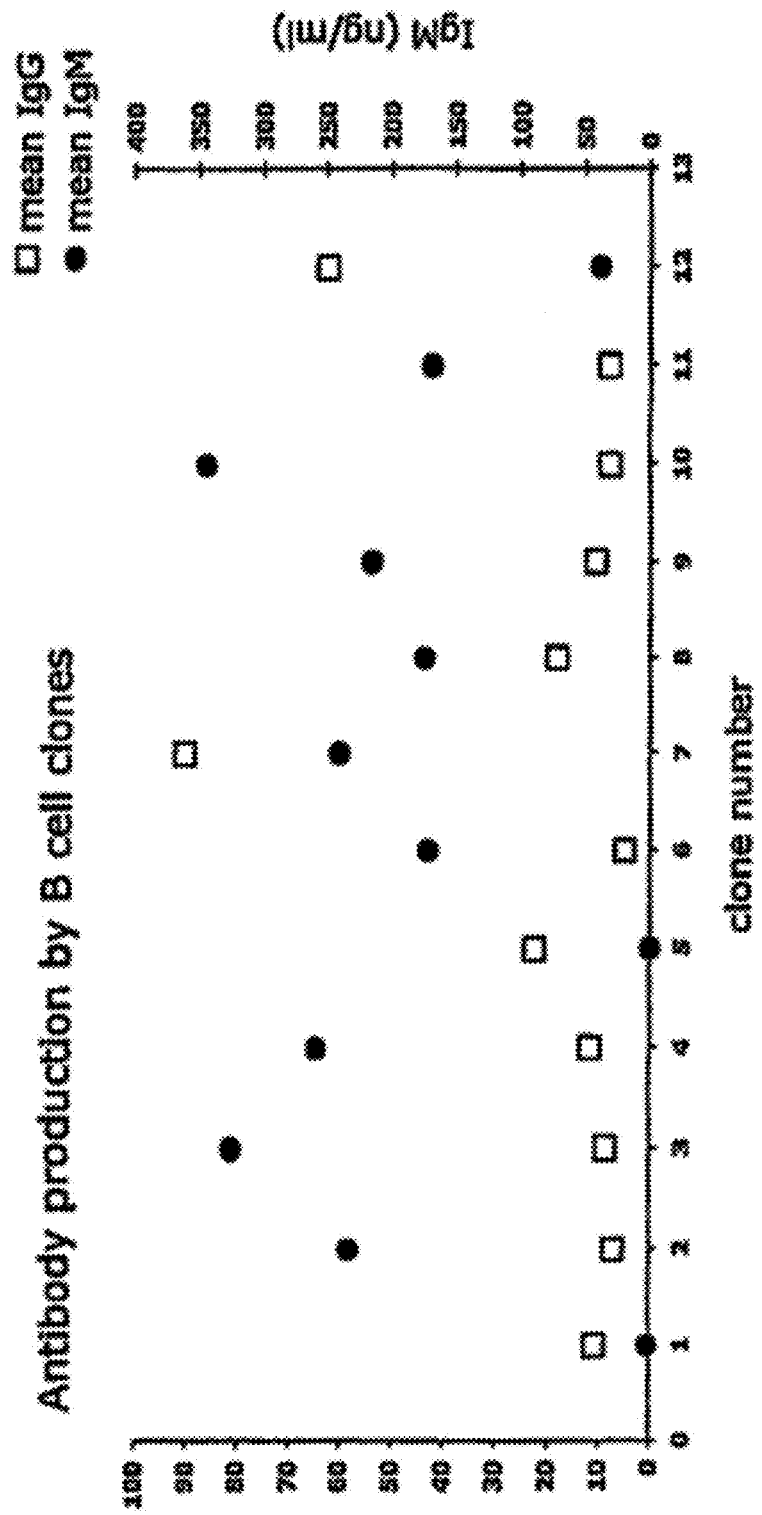
FIG. 9
Antibody production of B cell clones derived from memory B cells of donors B18 and B19 transduced with caSTAT5b-ER-IRES-NGFR. Ten-day-old cultures that were derived from IL-21 stimulated B cells (stimulated for 36 h) were used for LD culture. Twelve clones were obtained; 5 from and 7 from B19. IgG production is the mean of three time points; IgM production is the mean of two time points.
Figure 10A:
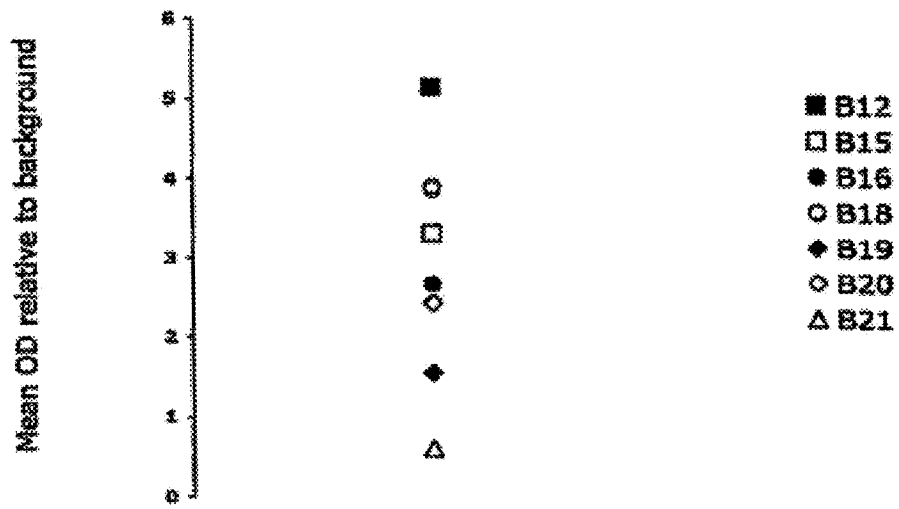
FIG. 10
IgG Tetanus Toxoid ELISA on supernatant of polyclonal, 100% caSTA5b-ER-IRES-NGFR positive, Tetanus Toxoid sorted human B cells. (a) Of 7 donors rapidly proliferating clonal cultures were derived. Shown is the average TT antibody production of at least 3 different measurements per donor. Each time the relative OD was determined (generally a relative increase of >2 to 3 times the background is assumed positive). (b) To determine if TT IgG ELISA negative cultures could be producing IgM, the same 7 donor samples were tested in a total IgM ELISA.
Figure 10B:
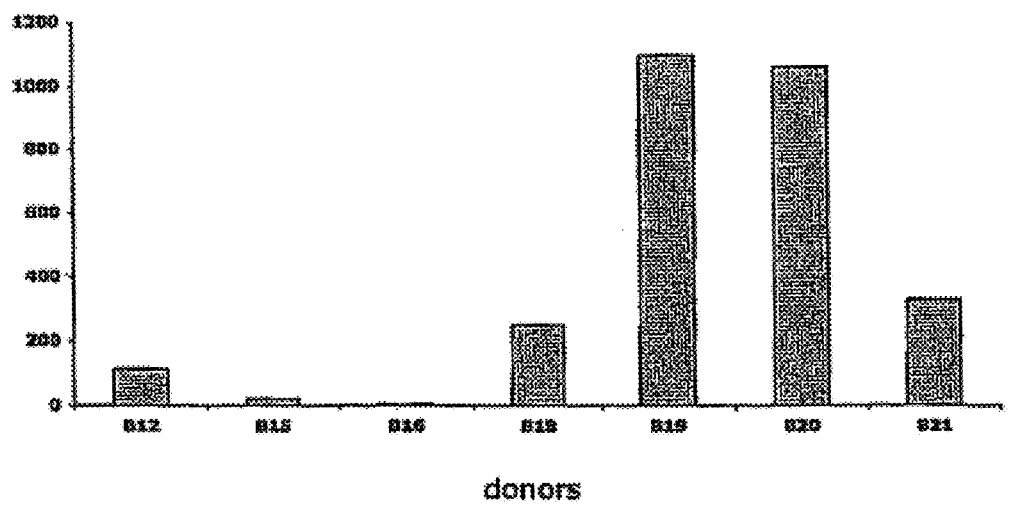
Figure 11:
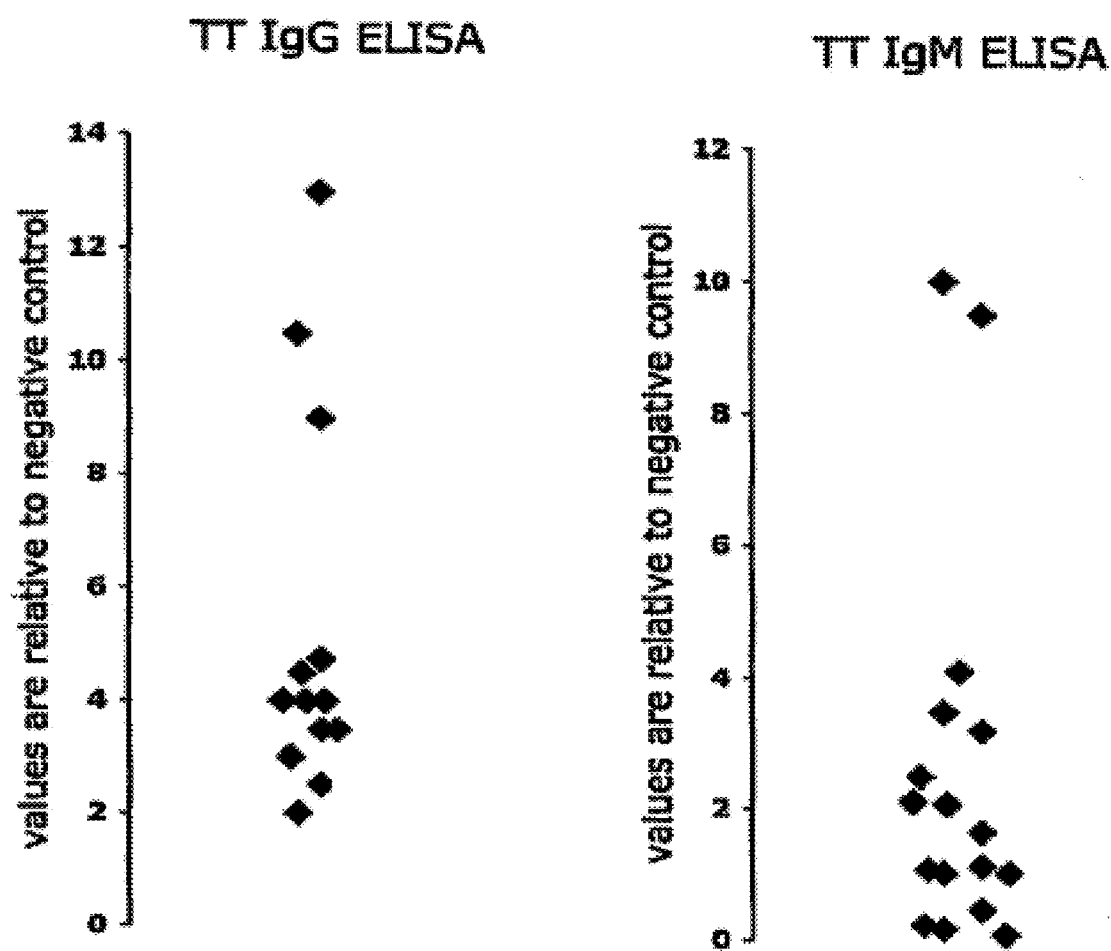
FIG. 11
Anti-Tetanus Toxoid ELISA. The binding of IgG and IgM α-TT specific antibodies by ELISA was determined. Supernatants of 100% NGFR positive clonal B cell cultures derived from donors B15, B16, B18 and B19 were tested. Two times the background was set as positive.
Figure 12A:
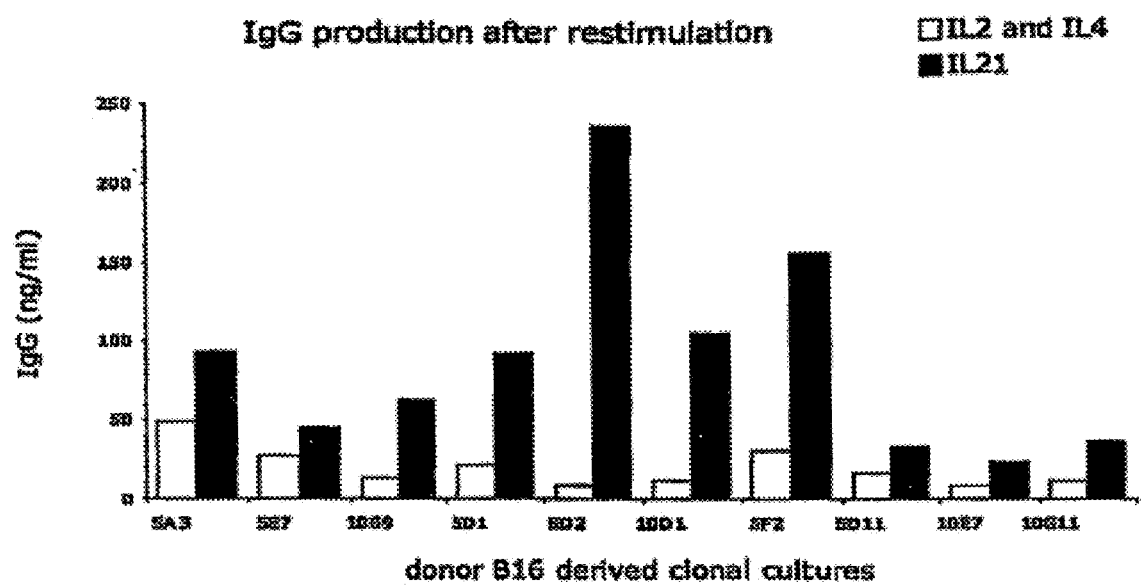
FIG. 12
Total IgG and IgM production after restimulation of clonal B cell cultures (a) donor B16 which produces IgG and (b) donor B19 which produces IgM. Production was measured in supernatant of cultures that were either cultured with IL-2, IL-4 and in the presence or absence of 4HT or with IL-21 and in the presence or absence of 4HT. Cultures containing IL-2 and IL-4 did not show an increase in antibody secretion (not shown). Only cultures that responded to the restimulation are shown (10 out of 14 IgG and 8 out of 9 IgM clones responded)
Figure 12B:
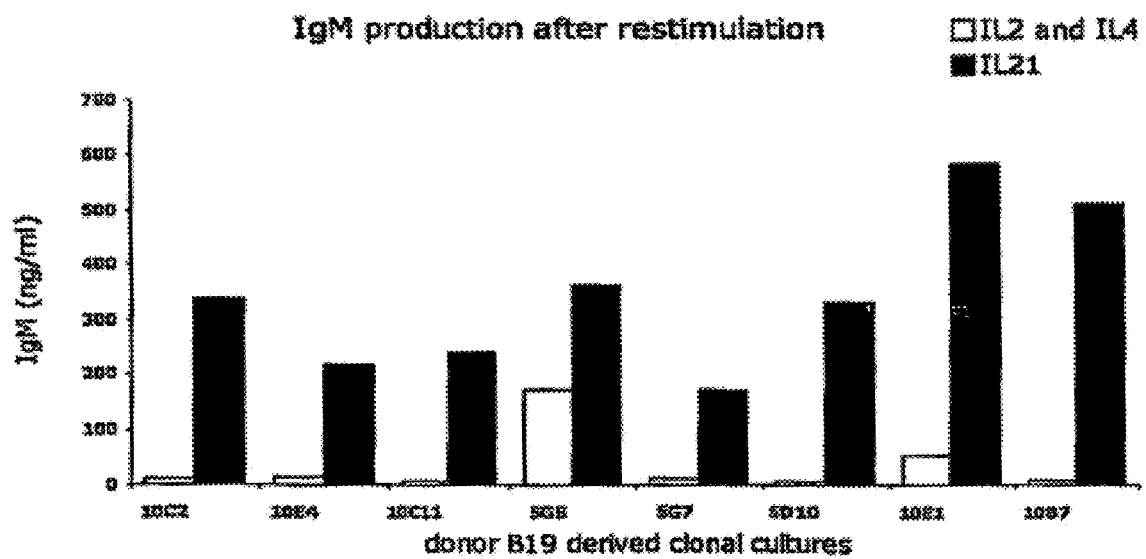
Figure 13A:
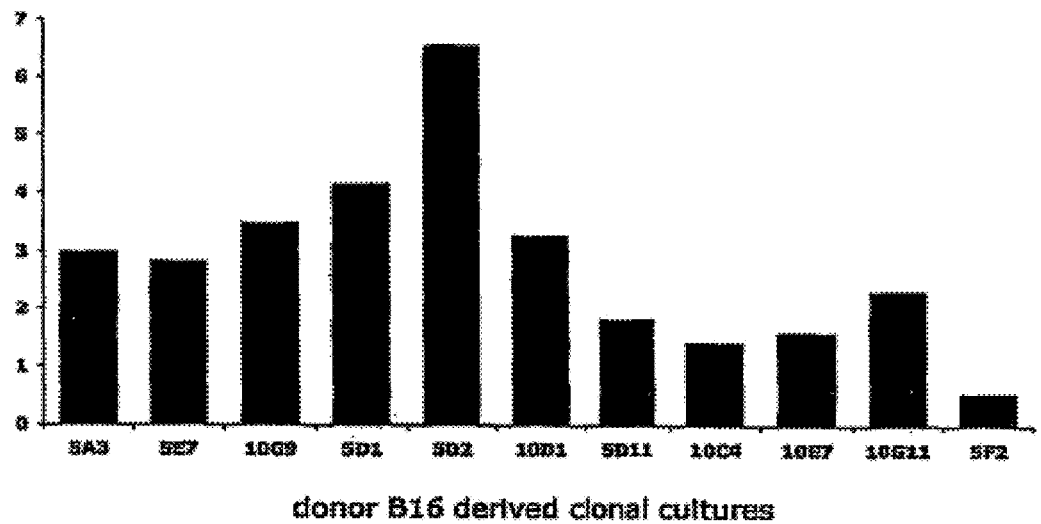
FIG. 13
Antibodies secreted by IL-21 restimulated and 4HT deprived cultures, as described in the legend of FIG. 8 were tested for their antigen specificity. The supernatants derived from restimulated donor B16 clonal TT cultures were tested in the α-TT IgG ELISA (a), the supernatants derived from donor B19 cultures were tested in the IgM ELISA (b). Shown is the relative increase in antibody binding compared to the negative control, samples B19-10B7 and 10E1 were cut off at 30 for visibility; values were 96 and 121, respectively.
Figure 13B:
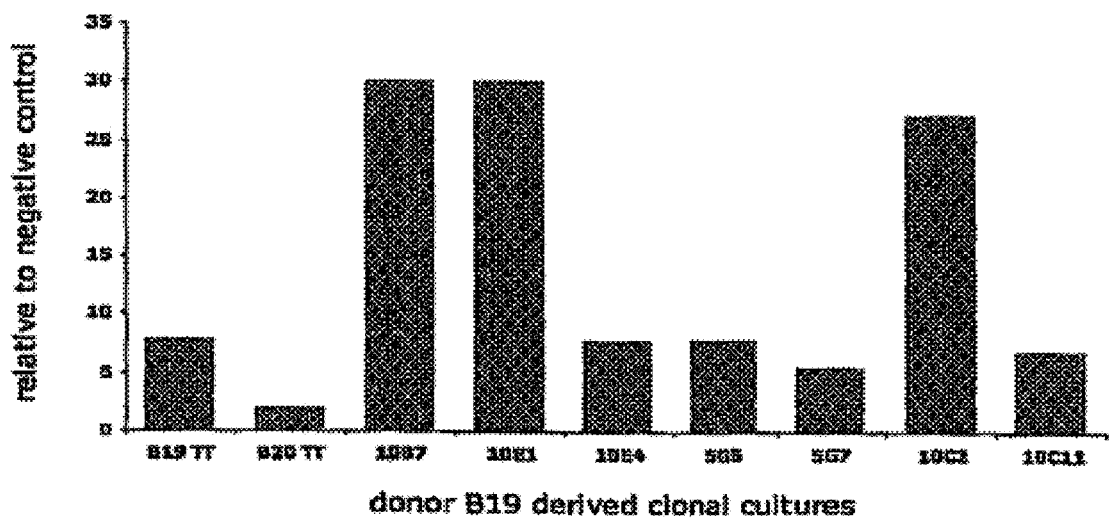
Figure 14:
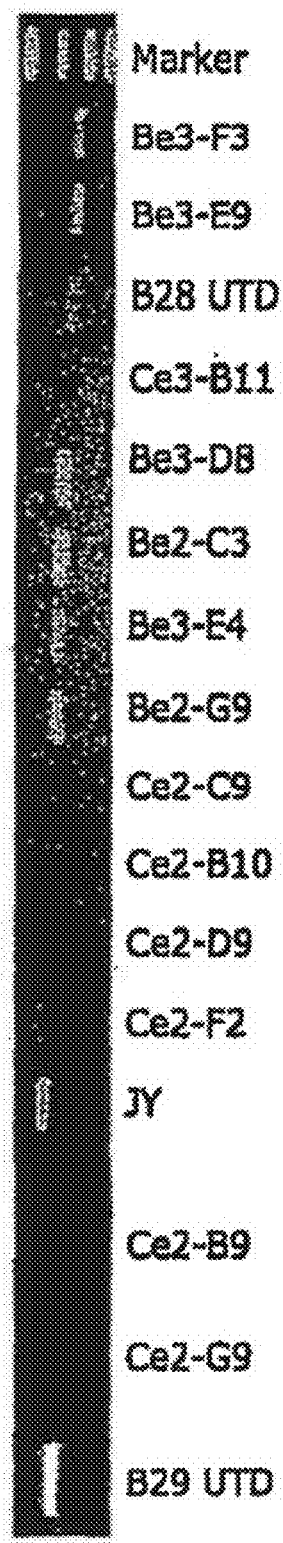
FIG. 14
LMP1 RT-PCR was performed on RNA isolated from frozen cell pellets of indicated cultures. Shown are 15 cultures which were randomly selected and tested for EBV infection. Sample coding: B indicates donor B29, C indicates donor B30 and both were cultured at 1000 c/w (e3) or 100 c/w (e2). All cultures were transduced with BCL6 except for B28 UTD (untransduced) and B29 UTD; JY cells were used as positive controls.
Figure 15:
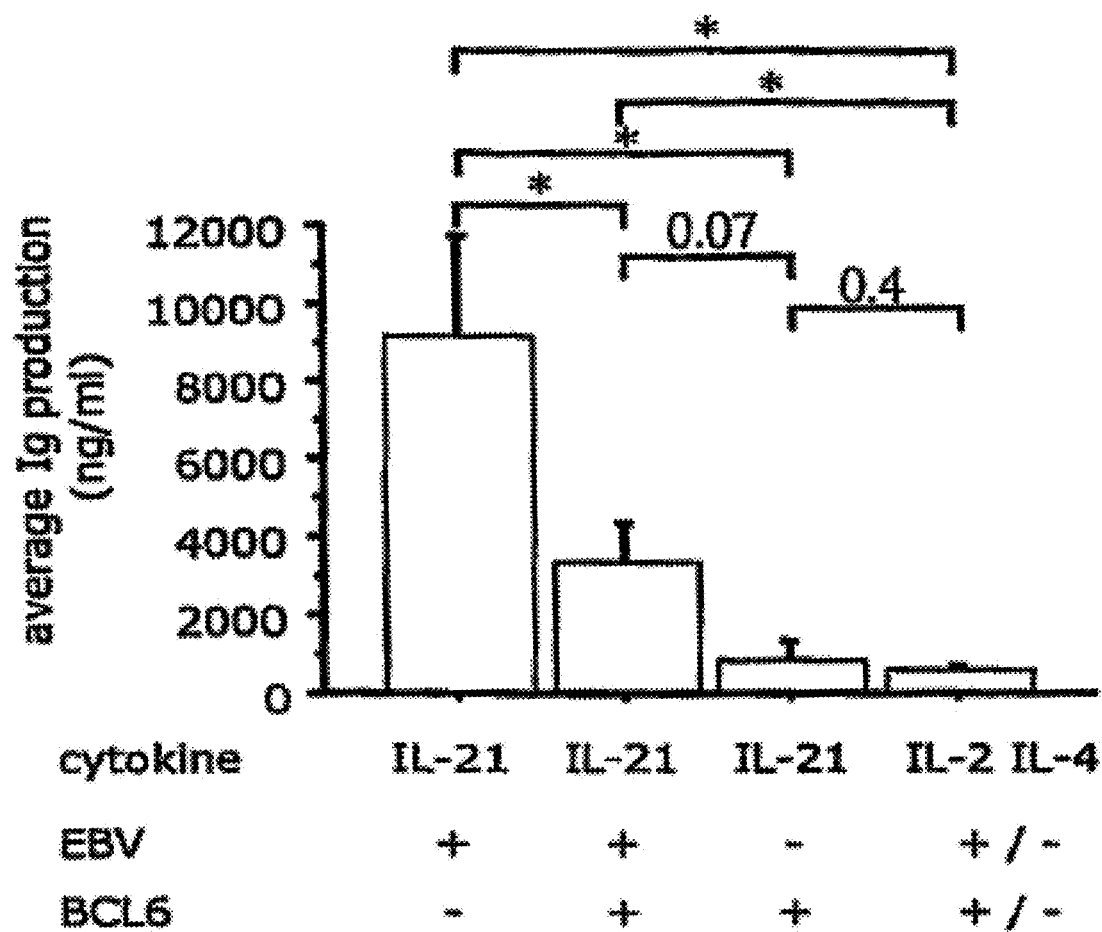
FIG. 15
IgG antibody production (ng/ml) by BCL6 and EBV cultures as described in table 5. For each condition the average of two samples is shown each of which consist of a longitudinal follow up of 6 to 10 time points. An asterisks indicates samples are significantly different (p<0.05, unpaired student t-test). The samples cultured with IL-2 and IL-4 are a combination of EBV and BCL6 positive and negative cultures longitudinal followed.
Figure 16:
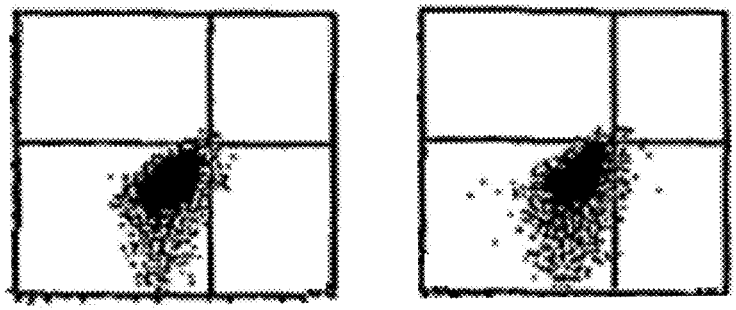
FIG. 16
Figure 16:
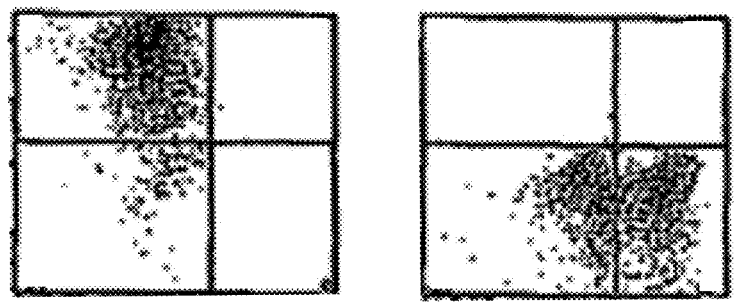
Figure 16:
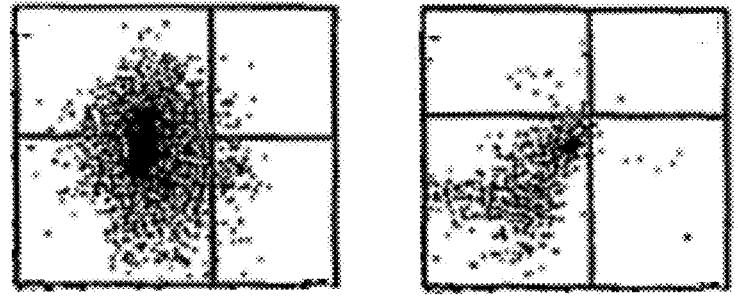
Figure 17:
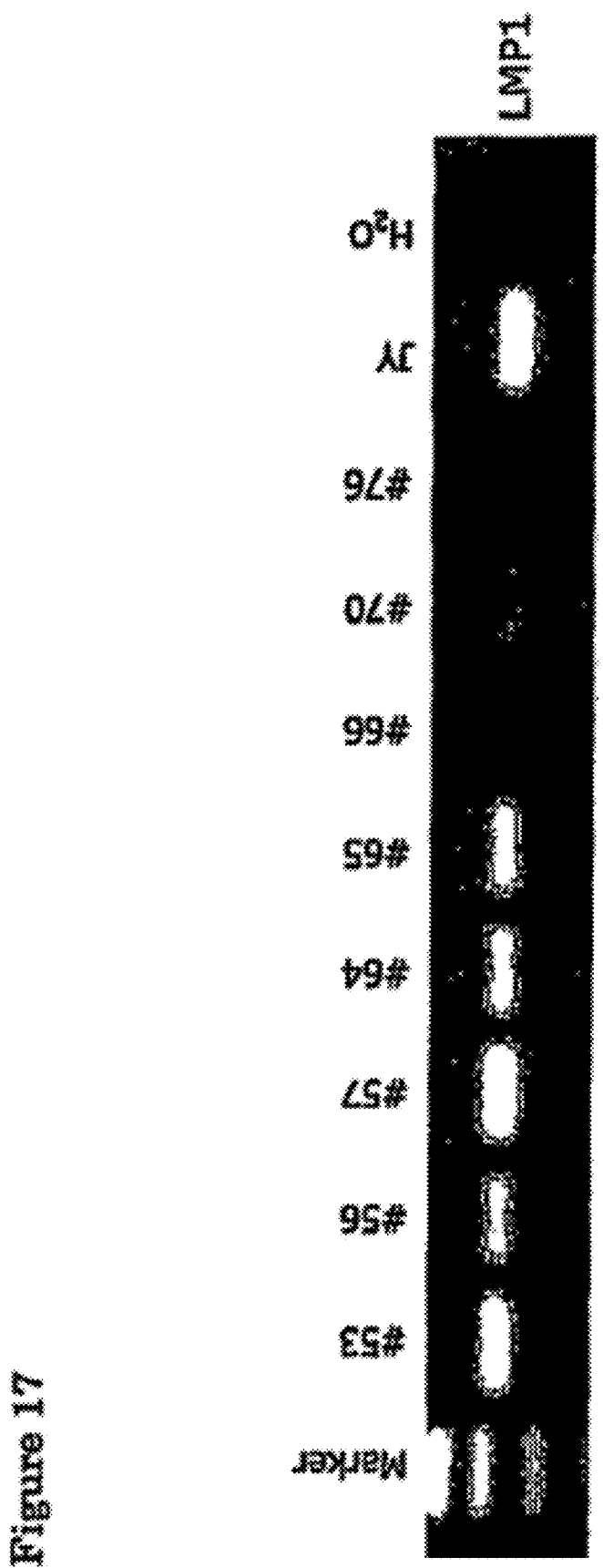
Figure 18:
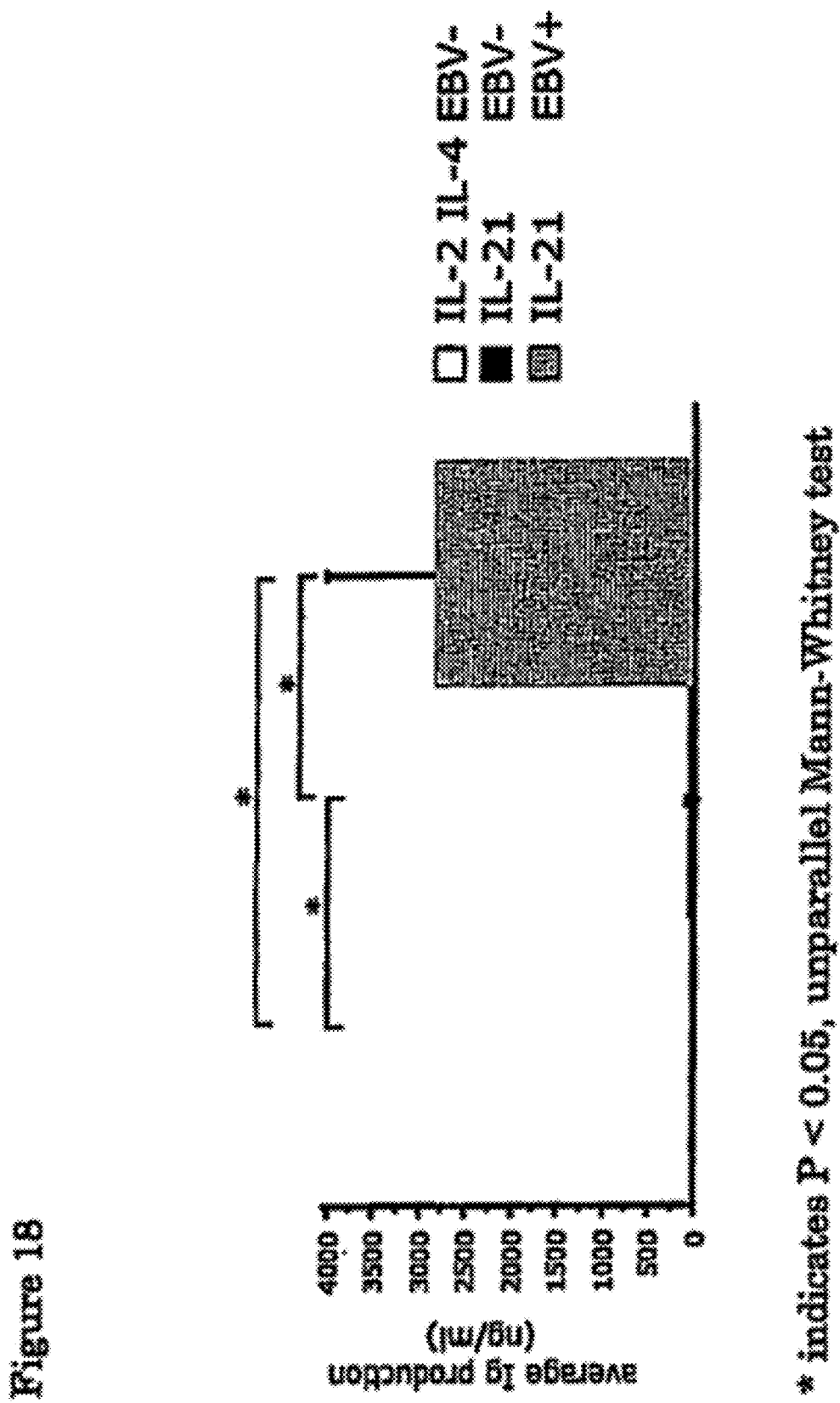
Figure 19:
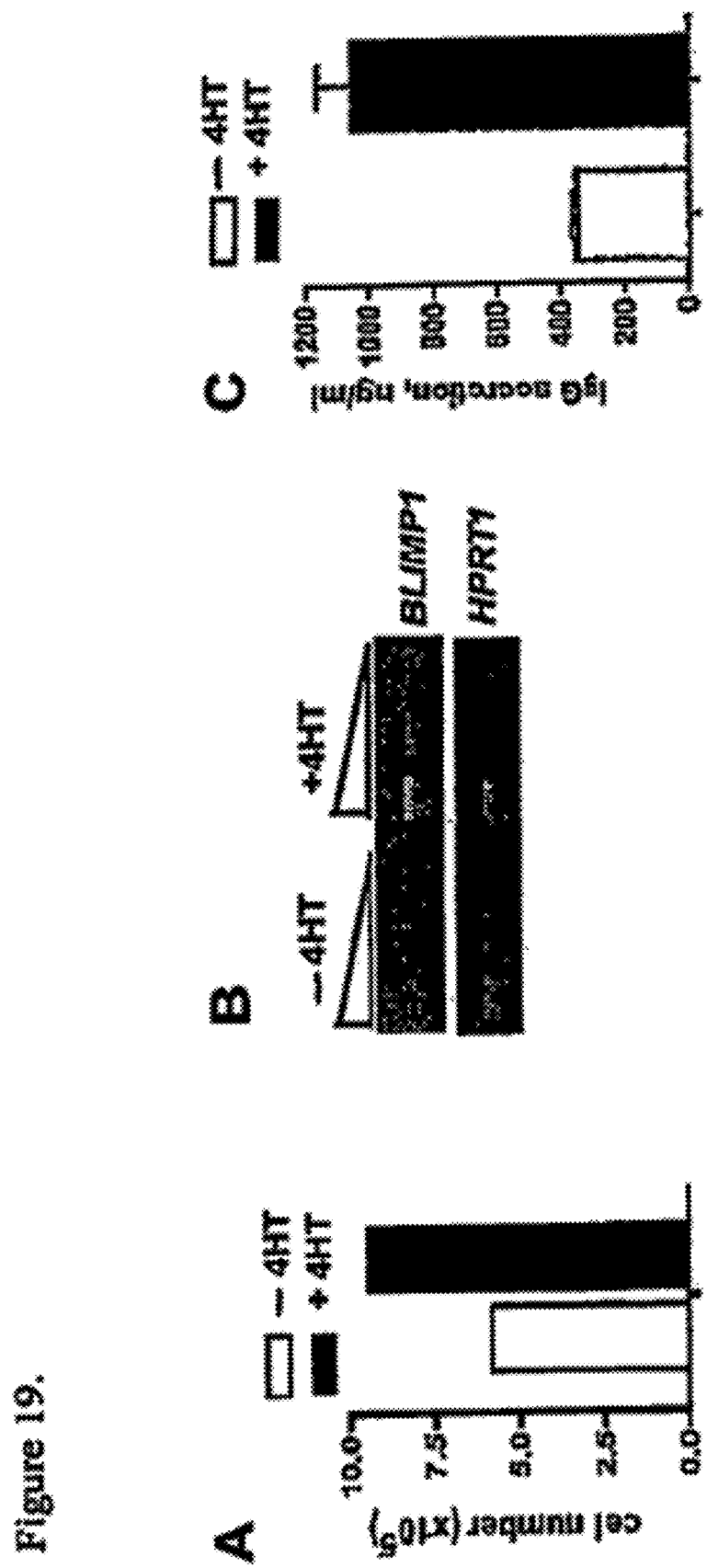
Figure 20:
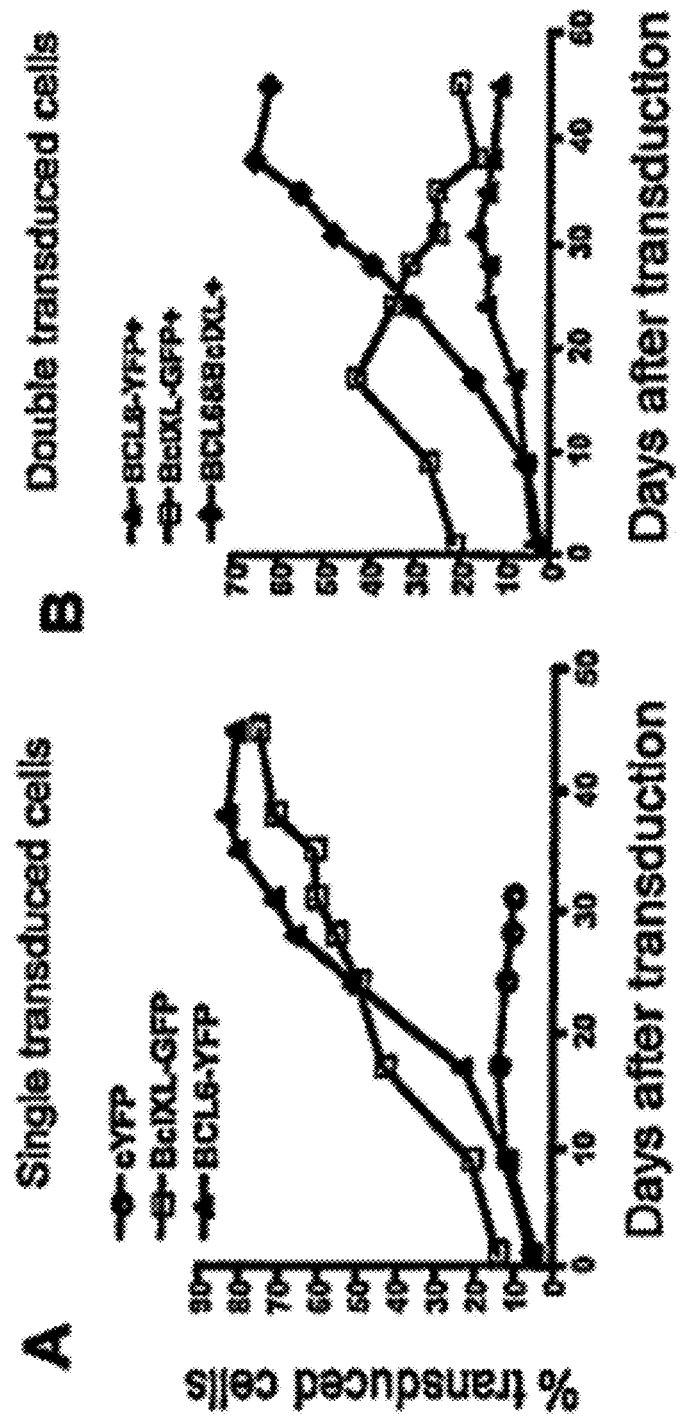
Figure 21:
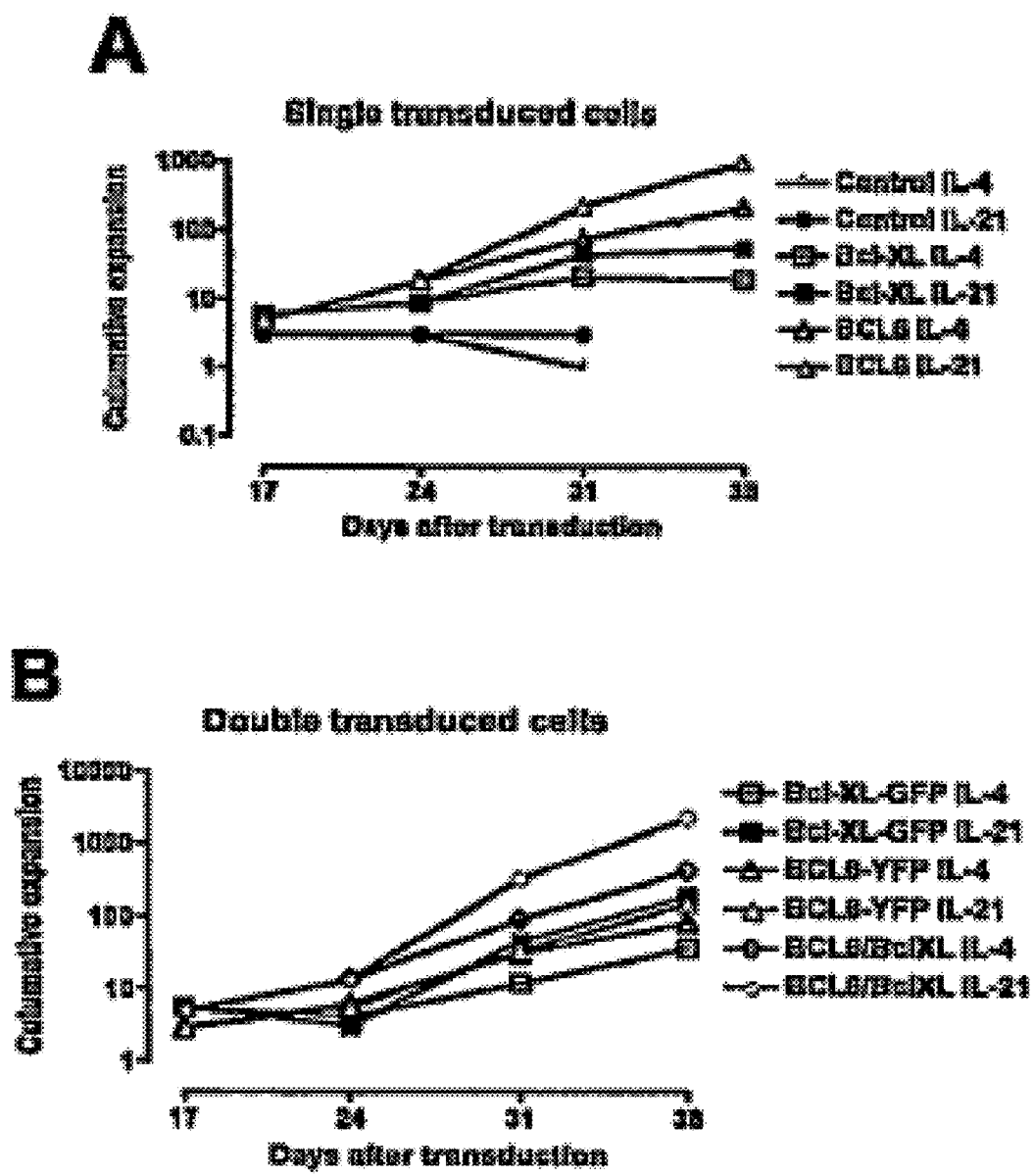
Figure 22:
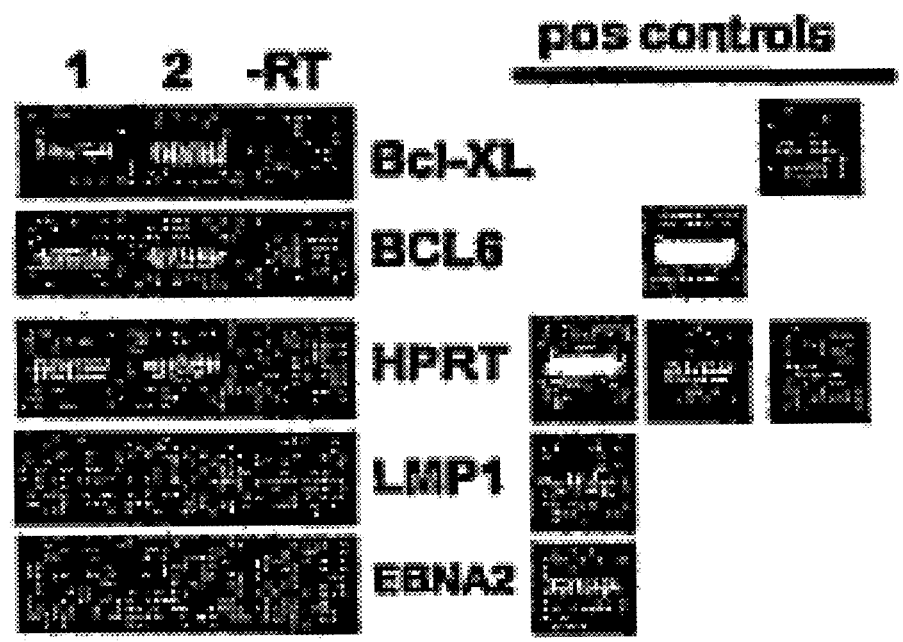
Figure 23:
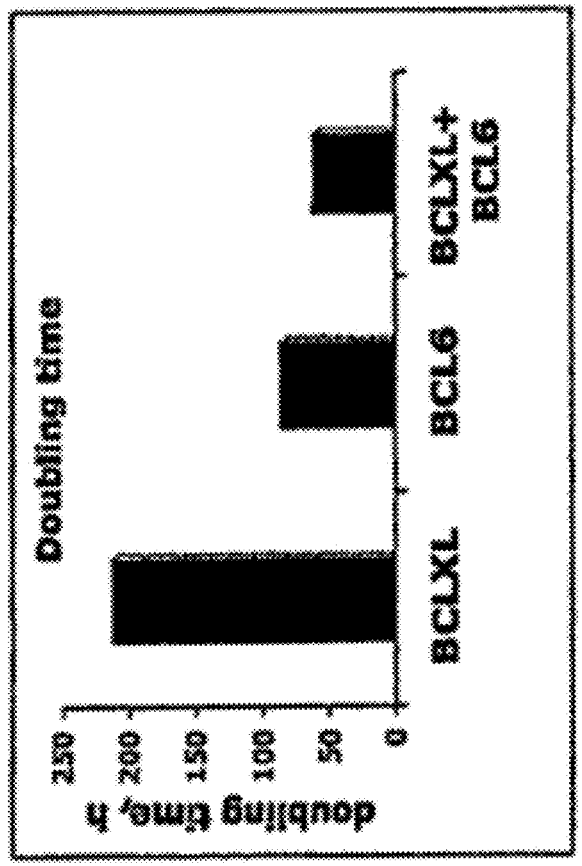
Figure 24:
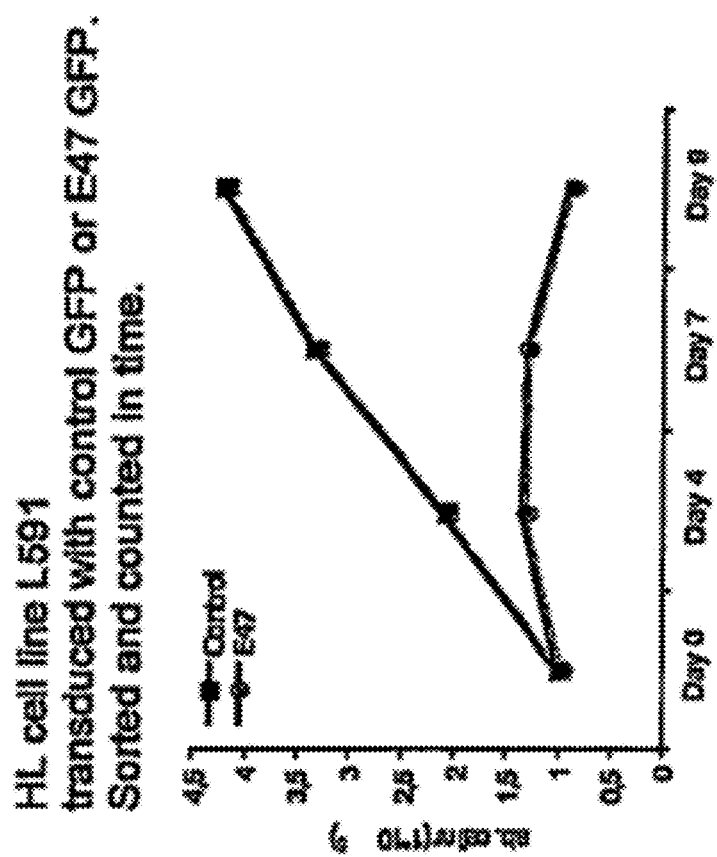

Kappa-FITC and Lambda-PE staining on CD19, and NGFR positive cells. One B cell is either positive for Kappa or Lambda. Samples were measured using a LSRII (BD) and analysed using FlowJo software.

FIG. 17

Shown is a representative LMP1 PCR performed on DNA isolated from frozen cell pellets of donor B25 1000 c/w MBC transduced with caSTAT5b and suspected to be EBV positive based on the color of the culture medium, growth kinetics and phenotype as observed by light microscopy. All other cultures were EBV negative.

FIG. 18

Average IgG production (ng/ml) in caSTAT5b-ER B cells cultured without 4HT, with IL-2 IL-4 or IL-21 and with or without EBV. The increase in antibody production in the presence of IL-21 was significant compared to cultures with IL-2 and IL-4 (p<0.05). The increase in antibody production in IL-21 containing, EBV infected cultures was significant compared to cultures without EBV (p<0.05), nonparametric Mann-Whitney)

FIG. 19

(A-C) BCL6-IRES-YFP.sup.+ cells were transduced with STAT3ER-IRES-GFP and expanded on CD40L L cells with IL-2 and IL-4. BCL6/STAT3ER positive cells were sorted by FACS and equal numbers were cultured in the absence of cytokines, but in the presence or absence of 4HT (1 .mu.M) for 4 days. (A) Live cell numbers after 4 days. (B) Semi-quantitative RT-PCR for BLIMP1 and HPRT1 expression in BCL6-YFP.sup.+/STAT3ER-GFP.sup.+ cells (C) IgG production in BCL6-YFP.sup.+ STAT3ER-GFP.sup.+ treated for 4 days .+-.4HT.

FIG. 20

A. CD19.sup.+ B cells were transduced with control YFP-IRES-YFP (cYFP); BCL6-IRES-YFP (BCL6-YFP) or BclXL-GFP (Bcl-xL-GFP). Cells were then maintained on CD40L and IL-4 and the percent YFP or GFP positive was determined over time by FACS. All data represented in A and B are derived from CD19+CD3.sup.- gating.

B. Unsorted bulk cultures of Bcl-xL-IRES-GFP and BCL6-IRES-YFP double transduced B cells on CD40L and IL-4. Individual GFP.sup.+, YFP.sup.+, and GFP/YFP double positive cells was determined by FACS

FIG. 21

IL-21 increased proliferation of B cells transduced with Bcl-xL, BCL6, or Bcl-xL+BCL6 double transduced cells.

At day 17 after transduction and maintenance on CD40L and IL-4, cultures were split and cultured on CD40L in the presence of IL-4, or IL-21. Absolute number of transduced cells was determined and the cumulative expansion was calculated in single transduced cells (A) or in double transduced cells (B).

FIG. 22.

Long-Term Cultures are EBV.sup.-

RT-PCR analysis of Bcl-xL, BCL6, LMP1, and EBNA1 mRNA expression in Day 66 cultures of BCL6-transduced cells (Lane 1) and BCL6/Bcl-xL-double transduced bulk cultures (Lane 2). 1 .mu.l of a cDNA reaction performed in the absence of reverse transcriptase (-RT) reaction was used as a negative control for genomic DNA contamination. Positive controls: Bcl-xL, STAT5-ER transduced B cells cultured with 4-HT; BCL6, LMP1, and EBNA1, human Raji B cells.

FIG. 23.

Doubling time of Bcl-xL, BCL6, and Bcl-xL-BCL6 double transduced cells. Based on the number of transduced (GFP.sup.+, YFP.sup.+) B cells the doubling time between days 51-59 of culture was calculated in Bcl-xL-, and BCL6-transduced cells in single transductions as well as in Bcl-xL+BCL6 double-transduced bulk cultures.

FIG. 24.

L591 a Hodgkin cell line, was transduced by lentivirus containing E47-IRES-GFP. GFP positive cells were sorted and cultured independent of L cells (CD40 stimulation) and cytokines. Cell numbers were determined in time.

REFERENCES

Banchereau, J., de Paoli, P., Valle, A., Garcia, E., Rousset, F., (1991). Long term human B cell lines dependent on interleukin-4 and antibody to CD40, Science 251, 70-2.

Boise, L. H., M. Gonzalez-Garcia, C. E. Postema, L. Ding, T. Lindsten, L. A. Turka, X. Mao, G. Nunez, and C. B. Thompson. (1993). Bcl-x, a bcl-2-related gene that functions as a dominant regulator of apoptotic cell death. Cell 74:597.

Dadgostar, H., Zarnegar, B., Hoffmann, A., Qin, X. F., Truong, U., Rao, G., Baltimore, D., and Cheng, G. (2002). Cooperation of multiple signaling pathways in CD40-regulated gene expression in B lymphocytes. Proc. Natl. Acad. Sci USA 99, 1497-1502.

Malisan, F., Briere, F., Bridon, J. M., Harindranath, N., Mills, F. C., Max, E. E., Banchereau, J., Martinez-Valdez, H. (1996). Interleukin-10 induces immunoglobulin G isotype switch recombination in human CD40-activated naive B lymphocytes, J. Exp. Med. 183, 937-47.

Mathas S, Janz M, Hummel F, Hummel M, Wollert-Wulf B, Lusatis S, Anagnostopoulos I, Lietz A, Sigvardsson M, Jundt F, Johrens K, Bommert K, Stein H, Dorken B (2006). Intrinsic inhibition of transcription factor E2A by HLH proteins ABF-1 and Id2 mediates reprogramming of neoplastic B cells in Hodgkin lymphoma. Nat Immunol. 7, 207-215.

Traggiai, E., Becker, S., Subbarao, K., Kolesnikova, L., Uematsu, Y., Gismondo, M. R., Murphy, B. R., Rappuoli, R., Lanzavecchia, A. (2004). An efficient method to make human monoclonal antibodies from memory B cells: potent neutralization of SARS coronavirus. Nature Medicine Volume 10, No. 8, 871-875.

Ye, B. H., Cattoretti, G., Shen, Q., Zhang, J., Hawe, N., de Waard, R., Leung, C., Nouri-Shirazi, M., Orazi, A., Chaganti, R. S., et al. (1997). The BCL-6 proto-oncogene controls germinal-centre formation and Th2-type inflammation. Nat Genet 16, 161-170.

What is claimed is:

1. An antibody producing B cell culture, comprising:
   at least one of IL-21 and/or IL-10; and
   B cells, said B cells comprising an exogenous nucleic acid sequence, said exogenous nucleic acid sequence encoding a peptide comprising Bcl6, or a functional part thereof, capable of increasing the replicative life span of an antibody producing B cell.

2. The antibody producing B cell culture according to claim 1, wherein the B cells further comprise an exogenous anti-apoptotic nucleic acid sequence.

3. The antibody producing B cell culture according to claim 2, wherein the exogenous anti-apoptotic nucleic acid sequence encodes a member of the anti-apoptotic Bcl 2 family.

4. The antibody producing B cell culture according to claim 2, wherein the exogenous anti-apoptotic nucleic acid sequence encodes a peptide comprising Bcl-xL, or a functional part thereof, capable of increasing the replicative life span of an antibody producing B cell.

5. The antibody producing B cell culture according to claim 4, wherein expression of the nucleic acid sequence encoding Bcl6 or Bcl-xL, or a functional part of Bcl6 or Bcl-xL, is regulated by at least one of an activator and/or repressor that is inducible by an exogenous compound.

6. The antibody producing B cell culture according to claim 1, wherein the B cells further comprise an exogenous compound capable of directly or indirectly enhancing Bcl xL expression.

7. The antibody producing B cell culture according to claim 6, wherein the compound comprises at least one of APRIL, BAFF, CD40, BCR stimulation, cytokines, growth factors or downstream effector(s).

8. The antibody producing B cell culture according to claim 1, wherein the B cells are capable of replicating for at least nine weeks.

9. The antibody producing B cell culture according to claim 1, wherein the B cells are capable of producing antibodies against an antigen of interest.

10. The antibody producing B cell culture according to claim 9, wherein the B cells are derived from an individual, which individual had been previously exposed to said antigen of interest.

* * * * *

UNITED STATES PATENT AND TRADEMARK OFFICE
CERTIFICATE OF CORRECTION

PATENT NO. : 9,822,339 B2  
APPLICATION NO. : 14/836335  
DATED : November 21, 2017  
INVENTOR(S) : Hergen Spits et al.

Page 1 of 1

It is certified that error appears in the above-identified patent and that said Letters Patent is hereby corrected as shown below:

On the Title Page

Item (30), the December 6, 2006 priority date for EP 06076211 should be June 12, 2006.

Signed and Sealed this  
Fifth Day of June, 2018

Andrei Iancu  
*Director of the United States Patent and Trademark Office*